(12) United States Patent
Knauf et al.

(10) Patent No.: US 8,192,964 B2
(45) Date of Patent: Jun. 5, 2012

(54) SAFFLOWER WITH ELEVATED GAMMA-LINOLENIC ACID

(75) Inventors: Vic C. Knauf, Bainbridge Island, WA (US); Christine Shewmaker, Woodland, CA (US); Frank Flider, Scottsdale, AZ (US); Donald Emlay, Davis, CA (US); Eric Rey, Berkeley, CA (US)

(73) Assignee: Arcadia Biosciences, Inc., Davis, CA (US)

( * ) Notice: Subject to any disclaimer, the term of this patent is extended or adjusted under 35 U.S.C. 154(b) by 0 days.

(21) Appl. No.: 13/025,345

(22) Filed: Feb. 11, 2011

(65) Prior Publication Data

US 2011/0129428 A1 Jun. 2, 2011

Related U.S. Application Data

(62) Division of application No. 11/438,951, filed on May 22, 2006, now Pat. No. 7,893,321.

(60) Provisional application No. 60/684,134, filed on May 23, 2005, provisional application No. 60/735,984, filed on Nov. 10, 2005.

(51) Int. Cl.
    C12P 7/64    (2006.01)
    A61K 45/00   (2006.01)
    A01N 65/00   (2009.01)
    C11C 1/00    (2006.01)
    C12N 15/82   (2006.01)

(52) U.S. Cl. ............ 435/134; 424/283.1; 424/725; 424/776; 435/271; 800/281

(58) Field of Classification Search ............ None
     See application file for complete search history.

(56) References Cited

U.S. PATENT DOCUMENTS

| 5,614,393 | A * | 3/1997 | Thomas et al. ............ 435/134 |
| 6,459,018 | B1 | 10/2002 | Knutzon |
| 6,653,530 | B1 | 11/2003 | Shewmaker |
| 6,815,579 | B1 | 11/2004 | Kunst |
| 6,825,398 | B2 | 11/2004 | Wang |

FOREIGN PATENT DOCUMENTS

| CN | 1253588 A | 5/2000 |
| WO | 96/21022 A2 | 7/1996 |
| WO | 98/46763 A1 | 10/1998 |
| WO | 98/46764 A1 | 10/1998 |
| WO | 99/64614 A2 | 12/1999 |
| WO | 02/081668 A2 | 10/2002 |

OTHER PUBLICATIONS

Reddy et al 1996 Nature Biotechnology 14:639-642, provided in Applicants' IDS.*
International Search Report for PCT Application No. PCT/US06/20047, dated Sep. 4, 2007.
Office Action received for Argentine Patent Application No. P060102090, mailed on Jul. 7, 2010, 4 pages of English Translation.
Office Action received for Australian Patent Application No. 2006249983, mailed on Jun. 1, 2010, 2 pages.
Office Action received for Chinese Patent Application No. 200680024359.6, mailed on Aug. 17, 2010, 9 pages of Office Action and 11 pages of English Translation.
Supplementary European Search Report and Search Opinion mailed Jan. 23, 2009, for EP Application No. 06771043.4 filed May 22, 2006, 19 pages.
Cook, Modification of fatty acid composition in tomato (*Lycopersicon esculentum*) by expression of a borage Δ6-desaturase. Molecular Biotechnology 21:123-128, 2002.
Damude, Enhancing plant seed oils for human nutrition. Plant Physiology 147:962-968, 2008.
Hong, High-level production of γ-linolenic acid in *Brassica juncea* using a Δ6-desaturase from *Pythium irregular*. Plant Physiology 129:354-362, 2002.
Huang, Cloning of Δ12- and Δ6-desaturases from *Mortierella alpina* and recombinant production of γ-linolenic acid in *Saccharomyces cerevisiae*. Lipids 34(7):649-659, 1999.
Huang, Enzymes for transgenic biosynthesis of long-chain polyunsaturated fatty acids. Biochimie 86:793-798, 2004.
Huang, Transgenic production of long-chain polyunsaturated fatty acids. World Review of Nutrition and Dietetics 88:243-248, 2001.
Hubbard, Evening Primrose Oil (EPO) Therapy to Restart a Child's Mental and Physical Growth, presented at the Annual Meeting of the Federation of American Societies for Experimental Biology on Experimental Biology, Orlando, Florida, Mar. 31-Apr. 4, 2001, The FASEB Journal 15:A641, 2001 (Abstract only).
Ishakawa, Effects of gammalinolenic acid on plasma lipoproteins and apolipoproteins. Atherosclerosis 75:95-104, 1989.
Li, Expression of *Mortierella isabellina* Δ6-fatty acid desaturase gene in γ-linolenic acid production in transgenic tobacco. Chinese Journal of Biotechnology 19(2):178-184, 2003 (English abstract on pp. 183-184).
Li, Heterologous expression of *Mortierella isabellina* Δ6-fatty acid desaturase gene in soybean. Acta Genetica Sinica 31(8):858-863, 2004 (English abstract on p. 858).
Liu, Characterization of oil exhibiting high γ-linolenic acid from a genetically transformed canola strain. Journal of the American Oil Chemists' Society 78(5):489-493, 2001.
Qiu, Expression of borage Δ6-desaturase in *Saccharomyces cerevisiae* and oilseed crops. Canadian Journal of Botany 80:42-49, 2002.
Reddy, Expression of a cyanobacterial Δ6-desaturase gene results in γ-linolenic acid production in transgenic plants. Nature Biotechnology 14:639-642, 1996.
Sato, Production of γ-linolenic acid and stearidonic acid in seeds of marker-free transgenic soybean. Crop Science 44:646-652, 2004.
Srinivas, Safflower petals: A source of gamma linolenic acid. Plant Foods for Human Nutrition 54:89-92, 1999.

* cited by examiner

Primary Examiner — Brent T Page

(57) ABSTRACT

The present invention relates to compositions and methods for preparing gamma-linoleic acid (GLA) in safflower plants, particularly from seeds of safflower. Nucleic acid sequences and constructs encoding one or more fatty acid desaturase sequences are used to generate transgenic safflower plants that contain and express one or more of these sequences and produce high levels of GLA in safflower seeds. Provided are transgenic safflower plants and seeds that produce high levels of GLA. Additionally provided are oils produced from seeds of this invention. The invention also relates to methods of treating a variety of diseases including nervous system disorders, inflammatory conditions, cancer and cardiovascular disorders using the oils of this invention.

10 Claims, 10 Drawing Sheets

Amino Acid Alignment of Plant Delta-6 Desaturases

```
                                   1                                                                    70
AAC49700 Borago officinalis D6   (1) -----MAAQIKKYITSDLLKNHDKPGDLWISIQGKAYDVSDWVKDHPGGSFPLKSLAGQEVTDAFYAEHP
AAP23034 Primula farinosa D6     (1) MANKSPPNPKTGYITSSDLKSHNKAGDLWISIHGQVYDVSSWAALHPGSTAPLMALAGHDVTDAFLAYHP
AAP23036 Primula vialli D6       (1) MANKSPPNPKTGYITSSDLKGHKKAGDLWISIHGEVYDVSSWAGLHPGSAPLMALAGHDVTDAFLAYHP
                     Consensus   (1) MANKSPPNPKTGYITSSDLK HNKAGDLWISIHG VYDVSSWAALHPGGSAPLMALAGHDVTDAFLAYHP
                                  71                                                                   140
AAC49700 Borago officinalis D6  (66) ASTWKNLDKFFTGYYLKDYSVSEVSKDYRKLYFEFSKWGLYDKKGHIMEATLCFVAMLFAMSVYGYIFCE
AAP23034 Primula farinosa D6    (71) PSTARLLPPLSTNLLLQNHSVSFTSSDYRKLLDNTHKHGLFRARGHTAYAIFVFMIAMFLMSVTGVLCSE
AAP23036 Primula vialli D6      (71) PSTARLLPPLSTNLLLQNHSVSFTSSDYRKLLHNHHKIGHFRARGHTAYAIFVYMIMMFLTSVTGVLCSE
                     Consensus  (71) PSTARLLPPLSTNLLLQNHSVSFTSSDYRKLL NFHKIGLFRARGHTAYATFVFMIMMFLMSVIGVLCSD
                                 141                                                                   210
AAC49700 Borago officinalis D6 (136) GVLVHLFSGCLMGFLWIQSGWIGHDAGHYMVVSDSRLNKFMGIFAANCLSSISIGWWKWNENAHHIACNS
AAP23034 Primula farinosa D6   (141) SAWVHLASGAAMGFAWIQCCWIGHDSGHYRIMSDRKWNWFAQILSTNCLQGISIGWWKWNENAHHIACNS
AAP23036 Primula vialli D6     (141) SAWVHLASGAAMGFAWIQCCWIGHDSGHYRIMSDRKWNWFAQWLSTNCLQGISIGWWKWNENAHHIACNS
                     Consensus (141) SAWVHLASGAAMGFAWIQCCWIGHDSGHYRIMSDRKWNWFAQILSTNCLQGISIGWWKWNHNAHHIACNS
                                 211                                                                   280
AAC49700 Borago officinalis D6 (206) LEYDPDLQYIPFLVVSSKFEGSLTSHFYEKKLTFDSLSRFFVSYQHWTFYPLMCAAARLNMYVQSLIMLS
AAP23034 Primula farinosa D6   (211) LDYDPDLQYIPLLVVSEKEFNSLTSREYLKKLNFDGVSRFLVCYQHWIKYPVMCYAARLNMLAQSFILFS
AAP23036 Primula vialli D6     (211) LDYDPDLQYIPLLVVSPKFFNSLTSREYDKKLNFDGVSRFLVGYQHWTFYPVMCVARLNMKAQSFITLFS
                     Consensus (211) LDYDPDLQYIPLLVVSPKFFNSITSRFYDKKLNFDGVSRFLVCYQHWTFYPVMCVARLNMIAQSFITLFS
                                 281                                                                   350
AAC49700 Borago officinalis D6 (276) KRNVSYRAHELLGCLVFSLAYPILLSCLPNWGERIMFVTASLSVTGMQQVQFSLNHFSSSVYVGKPKGNN
AAP23034 Primula farinosa D6   (281) SREVCHRAQEVFSLAVFWVAFPLLLSCLPNWGERIMFLLASYSVTGIQHVQFSLNHFSSDVYVGPPVGNE
AAP23036 Primula vialli D6     (281) SREVGHRAQEIFGLAVFWVAFPLLLSCLPNWSERIMFLLASYSVTGIDHVQFSLNHFSSDVYVGPPVANE
                     Consensus (281) SREV HRAQEIFGLAVFWVWFPLLLSCLPNWGERIMFLLASYSVTGIQHVQFSLNHFSSDVYVGPPVGND
                                 351                                                                   420
AAC49700 Borago officinalis D6 (346) WFEKQTDGTLDISCPPWMDWFHCGLCFQLEHHLFPKMPRCNLRKISPYVIELCKKHNLPYKYASEKANE
AAP23034 Primula farinosa D6   (351) WFKKQTAGTLNISCPAWMDKFHGGLCFQVEHHLFPRMPRGQFRKISPFVRDLCKKHNLPYKIASFTKANV
AAP23036 Primula vialli D6     (351) WFKKQTAGTLNISCPAWMDKFHGGLCFQVEHHLLFPRMPRGQFRKISPFVRDLCKKHNLPYKIASFTKANV
                     Consensus (351) WFKKQTAGTLNISCPAWMDWFHGGLCFQVEHHLFPRMPRGQFRKISPFVRDLCKKHNLPYN IASFTKANV
                                 421              453
AAC49700 Borago officinalis D6 (416) MTLRTLRNTALQARDLDKPLPKNVWEALHTHG (SEQ ID NO: 4)
AAP23034 Primula farinosa D6   (421) FTLKTLRNTAIEARDLSNPLPKNMVWEALKTLG (SEQ ID NO: 5)
AAP23036 Primula vialli D6     (421) LTLKTLRNTAIEARDLSNPTPKNMVWEAVHTHG (SEQ ID NO: 6)
                     Consensus (421) LTLKTLRNTAIEARDLSNPLPKNMVWEALHTHG
```

Similarity: 99.1%; Identity: 62.7%
AAC49700—Borago officinalis (448)
AAP23034—Primula farinosa (453)
AAP23036—Primula vialli (453)

Figure 2

Amino Acid Alignment of Fungal Delta-6 Desaturases

```
                                      1                                                                      70
AAF08685 Mortierella alpina D6   (1)  ----MAAAPSVRTFTRAEVLNAEALNEGKK-DAEAPFKMIIDNKVYDVREPVPDHPGGS-VTLDHV--GK
BAB6905 Mucor circinelloides D6  (1)  -MSSDVGATVPHFYTPAESADIHQDVLDK--KPEARKLIVVENKVYDTTDPVFDHPGGERVLLTQE--GR
BAC57562 Mucor circinelloides D6 (1)  MPPNTAADRLLSSTSTRSSNIVTEEKFQEL-IKQGDSVPIYRQKVYRVNNFMAKHPGGEAALRSAL--GR
Thraustochytrium aureum D6       (1)  ---------MGRGGERSEVDQVPQKTEQLQKAKWEDVVRINGVEYDVTDYLRKHPGGSVLKYGLANTGA
Saprolegnia diclina D6           (1)  ------------MVQGGQKAEKISWATIREH-NRQDNAWIVIHHKVYDISAE-EDHPGGV-VMFIQA--GE
Consensus                        (1)       A    L    TRAEV  I              A     LIIIENKVYDVTDFV  DHPGG   VL  T        GR 71                                                                    140
AAF08685 Mortierella alpina D6  (63)  DGTDVFDTEHPEAAWETLANFYVGDID-----------------------------------------
BAB6905 Mucor circinelloides D6 (66)  DATDVFHEMHDPSAYELLANCYVGDCEP---KLEI----------------------------------
BAC57562 Mucor circinelloides D6(68)  DVTDEIRTMHPPQVVLKMINLVCIGDYMPDVIREASMKQQHTFTKPKEDKPVLTATWEGGFTVQAYDDAI
Thraustochytrium aureum D6      (62)  DATSLFEAFHMRSKKAQMVLKSLPKRAPVLEIQEN----------------------------------
Saprolegnia diclina D6          (54)  DATDAFAVTHESSALKLLDGYLVGDVDQSTAAVDT----------------------------------
Consensus                       (71)  DATDVF  FHP SAYE L N YVGD D         P 141                                                                   210
AAF08685 Mortierella alpina D6  (90)  --------------ESDRDIKNDDFAASVEKLRTLFQSLGYKDSSKAYYAPKVSFNLCIWGLSTVIVAK
BAB6905 Mucor circinelloides D6 (98)  --------------DSTDKMALNSAAFAQEIRDERDKLEKQGYEDASTGFYIYKVSTTLLVCIVGLALLKA
BAC57562 Mucor circinelloides D6(138) QDLHKHHSHDLIKDAVLQKDLNGDQIRNAYRKLEAELYAKGLLKCNYWKYAREGCKRYTLLIFLSLWFTLK
Thraustochytrium aureum D6     (153) --------------QLPEEQTKEABMLRDEKKFEDEIRRDGLMEPSFWHRAYRLSELVGMFTLGLYLFSL
Saprolegnia diclina D6         (89)  --------------SISDEVKKSQSDFIASYRKLRLEVKRLGLYDSSKLYYLYKCASTLSLALVSAAICLH
Consensus                     (141)               EK L  ADF  EYRKLR EL R GLFDSS  YYAYKVS    L I  LSL I 211                                                                   280
AAF08685 Mortierella alpina D6 (145) WGQTSTLANVLSAALIGLFWQQCGWLAHDFLHMCVFQDRFWGDLFGAFLGGVCQGRSSSWWKDKHNTHHA
BAB6905 Mucor circinelloides D6(155) WGRESTLAVFLAASAVGLFWQQCGWLAHDYAHYGVIKDPNVNNLFLVTFGNLVQGFSLSWWKNKHNTHHA
BAC57562 Mucor circinelloides D6(208) GT--ETWHYMAGAAFMAMFWHQLVFTAHDAGHNEITGKSEIDHVLGVFFANFIGGLSLGWWKDNHNVHHI
Thraustochytrium aureum D6    (220) NT---PLSIAACVLVHGLFGAFCGWCQHEAGHCSFFYSLWWGKRVQAMLICFGLGTSCDMWNMMHNKHHA
Saprolegnia diclina D6        (146) KD--STAMYMVAAVIIGLFYQQCGWLAHDFLHQVFENHLFGDLVGVMVGNLWQGFSVQWWKNKHNTHHA
Consensus                    (211) W     STLA  MIAAALLGLFWQQCGWLAHDFGHHQVF      WG LVGVMLGNL QGFSL WWK KHNTHHA 281                                                                   350
AAF08685 Mortierella alpina D6 (215) APNVHG-------EDPDIDTHPELTWSEHALEMFSDVPDEELT---RMWSREMVLNQTWFYFPILSFARL
BAB6905 Mucor circinelloides D6(225) STNVSG-------EDPDIDTAPILLWDEFAVANFYGELKDNASGFDRFIAEHILPVQTRYYRFILGFART
BAC57562 Mucor circinelloides D6(276) VTNHPEH------DPDIQHVPFMAITTKFFNNIYSIYYKRVLP-FDAASRFFVRFQHYLYLILSFGRF
Thraustochytrium aureum D6    (267) ATQKVHH------DLDIDTTPFVAFFNTAFE---------------KNRWKGFSKAWVRFQAFTFIPM
Saprolegnia diclina D6        (214) IPNLHATPEIAFGHGDPDIDTMPILAWSLKMAQCHAVDSPVGLFF-----MR-----XQAYLYFPILLFARI
Consensus                    (281) ATNV G        DPDIDT  PILAWS  A          S               SRF V  YQ WLYF  ILSFARI 351                                                                   420
AAF08685 Mortierella alpina D6 (275) SWCLOSELFVLPNGQAHKPSGARVPISLVEQESLAMHWTWVLATMFLFIKDPVNMLVYFFVSQAVCGNLL
BAB6905 Mucor circinelloides D6(288) SWALQSIIYSFPKNETLNKSK----LLSWCIRLELIVEWVHTYCTIAWISSIRNIAMRVVGQITTGYLL
BAC57562 Mucor circinelloides D6(338) NLHRLSFAYLLTCKNVRTRT------E-ELVGITFFRVWEG--SLLSTLPTWNIRIAYFMVSYMLTFPL
Thraustochytrium aureum D6    (337) ISGMIVMLFWLFFLHPREVVQKNFEEGFWMLSSHIVRTLFLHLVTGWESLAACYLVSIVACMWVSGMYL
Saprolegnia diclina D6        (274) SWVIQSAMYAFYNVGPGGTFD--KVQYPLLERAGLLLYYGWNLGLVYAANMSLLQAAAELFVSQASCGLFL
Consensus                    (351) SW  IQSILY L N     K     K    L ELL  IHW WF    V AW       NI VFFIVSQ V G  L 421                                                                   490
AAF08685 Mortierella alpina D6 (345) AIVESINHNGMPVISKEEAVDMDFFTKQITTGEVHPG-IFANWFTGGLNYQIEHHLFPSMPRHNFSKIQ
BAB6905 Mucor circinelloides D6(354) AIVFAMNHNGMPVYSPEEANHTEFYELQCITGRDVNCI-VFGDWLMGGLNYQIEHHLPEMPREHLSKVK
BAC57562 Mucor circinelloides D6(398) HKQITLSHFGMSTEDRG--PDEPFPAKMIRTTMEVDCP-EWLDWFHGGLQVQAVHHLFPRLPRHNLRQCV
Thraustochytrium aureum D6    (337) FGHFSLSHTHMDIVEAD--VHKNWVRYAVDHIVEISPSNPLVCWVMGYLNMQTIHHLWPAMPQYHQVEVS
Saprolegnia diclina D6        (343) AMVFSMCHNGMEVFDKD--SKPDFWKLQVESTRNVTSS-LWIDWFMCGLNYQIDHHLFPMVPRHNLPALN
Consensus                    (421) AIVFSL  HNGM V DKD     DFF  QVITTRDV    S LFIDWFMGGLNYQIEHHLFP MPRHNL  V 491                                       549
AAF08685 Mortierella alpina D6 (414) PAVETECKKYNVRYHTTGMIEGTAEVFSRLNEVGKAASKMGKAQ---------------(SEQ ID NO: 7)
BAB6905 Mucor circinelloides D6(423) SMVKPIAQKYNIPYHDTTVIGGTIEVLQTLDFVQKISQKFSKKML--------------(SEQ ID NO: 11)
BAC57562 Mucor circinelloides D6(465) PLVKKFCDEVGLHYYMYNESTGNGVVLGTLKSVADQVGFMNEVAKSNAEIWANDKEHAH (SEQ ID NO: 8)
Thraustochytrium aureum D6    (405) RRFAIFAKKHGLNYRVVSYFEAWRLMLQNLADVGSHYHENGVKRAPKKAKAQ-------(SEQ ID NO: 9)
Saprolegnia diclina D6        (410) VIVKSLCKQYDIPYHETGEIAGMAEVVVHLERISIEFFKEFFPAM--------------(SEQ ID NO: 10)
Consensus                    (491)     LVK  LCKKY  I YH T FI G AEVL L   VS  K
```

Similarity: 53.7%; Identity: 7.1%
AAF08685 Mortierella alpina D6 (457)
BAB6905 Mucor circinelloides D6 (467)
BAC57562 Mucor circinelloides D6 (523)
Thraustochytrium aureum D6 (456) (SEQ ID NO: 33 from WO02081668)
Saprolegnia diclina D6 (453) (SEQ ID NO: 14 from US 6,635,451)

Figure 3

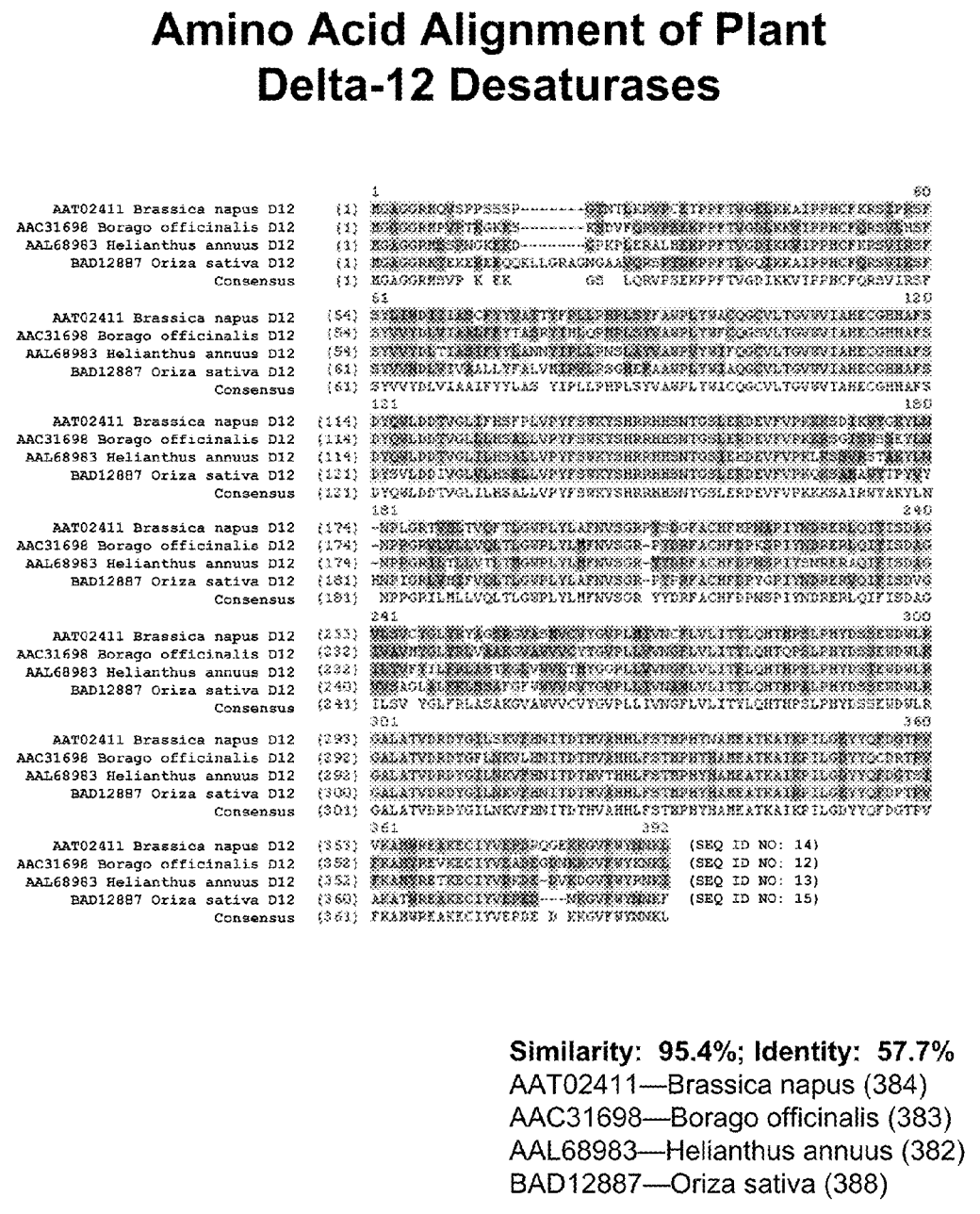

Amino Acid Alignment of Plant Delta-12 Desaturases

Similarity: 95.4%; Identity: 57.7%
AAT02411—Brassica napus (384)
AAC31698—Borago officinalis (383)
AAL68983—Helianthus annuus (382)
BAD12887—Oriza sativa (388)

Figure 5

Comparison of Fungal Delta-12 Desaturases

```
                                    1                                                          60
CAE47978 Aspergillus furnigatus D12  (1)  ------------------------------MASD=EK GSK-----  --ID GNEF
EAK94955 Candida albicans D12        (1)  M VVEA S VVEDS---------  ASNV  QR D    TAS  ASS----  NL T IT  NGKV
EAL03493 Candida albicans D12        (1)  M AATT F S GFNKKNNADQSTD    T SK  N ASFK  T T STYQTNLTAID  GNEF
AAF08684 Mortierella alpina D12      (1)  ---------------------MAPP T D  GLTORHI   APN------  A KPA  RN
                                   Consensus  (1)  MA    S SS                SAANII AGNIASFASTSASS      NLTAID YGNEF
                                    61                                                         120
CAE47978 Aspergillus furnigatus D12  (21)   PDYTIKQ IRDAIPAHCYQRS AATS LYY V R D  A  AS F YVF NY Y TPET      S
EAK94955 Candida albicans D12        (49)  KV DY  IK  ILOA I KHCYERS L RSLGYVVR DITMMY   GYVG T  LPM V     YPS  A
EAL03493 Candida albicans D12        (61)  KV PD   IK ILSAI F   CY RRL Q  LSYVFR D   CMVVLG  AN  Y  L IPN-------
AAF08684 Mortierella alpina D12      (33)  Q    T IK   I     ID HC F RS      G C   VAID  TWAS  FLAAT  I CKF  ND-------
                                   Consensus (61)  KVPDYTIKCIRDAIPAHCYERSLLRSL YVFRDITIMV LGYVAHNYI LENIP    A
                                    121                                                        180
CAE47978 Aspergillus furnigatus D12  (76)  MF RVV     V VV   D VGTGV VLAHEC H QAFS  S KVL   T VGW  CH SLL VFY  SWK
EAK94955 Candida albicans D12        (109) YG LRGA V  MVQ        L FGF G L  VLAHECGH GA FSDY QN   NDF  GW  L HSYL  VFY SWK
EAL03493 Candida albicans D12        (114) QF LR   AW  TG V         LFGTG L  VLAHECGH CA FSDY G    NDF VGW    HS  LLVFY FSWK
AAF08684 Mortierella alpina D12      (86)  -L     LAW  Y W IM   G   V CFGV V LAHECGH Q F S   L N  VGW  H SM L VFY  SW 
                                   Consensus (121)  IRFALWTVYSWCQGLVGTGVVVLAHECGHQAFSTYKSLNDTVGWILHSYLLVPYFSWK
                                    181                                                        240
CAE47978 Aspergillus furnigatus D12  (136)  SHGKEHHATGN  A DMVFVPK   EEYATR-------IGR AHEL  L MFFT PTL  ATN
EAK94955 Candida albicans D12        (169) F SHA KE HHKATG HLT  MVE  PY  KEEY  E---------KNK V   KY   L MEES P   L V
EAL03493 Candida albicans D12        (174) FSHG KE HHKATG  HLT KDMVFVFK  KEEE  Q--------- NR   VK   D T  CGS PM  G    TL
AAF08684 Mortierella alpina D12      (145)  SHSKEHHATGH  MT   DOVFVPK   SQVGLPFPKENAAAAV Q E D MSVH  D  E A  TV   FW
                                   Consensus (181)  ISHGKEHHKATGHLTKDMVFVPKIKEEYL         RAVDDLADLMEESPIYSLL L
                                    241                                                        300
CAE47978 Aspergillus furnigatus D12  (189)  LQQ   F WP MYL   TN V  CHNNEEROPEGR CK   RNGYFCCVNH FN PS  P Y  A RDAKLI
EAK94955 Candida albicans D12        (220)  FQQ  GGLQL YLA TN  GQ-----V PGY  K IA S--------H T F S  PV D KH Q YY I
EAL03493 Candida albicans D12        (225)  KQQT   Y   L Y  AN M GQ-----K  QGVS L KLN-------H FNFNSL I  DRK  WY I
AAF08684 Mortierella alpina D12      (205)  I QF S E WPAYL M NA G-----------DY RWTS------HE HTYS FL T F N E D T
                                   Consensus (241)  VFQQLFGWPMYLITNVSGQ      YPG SKGXKN    HFNPSSPIFDKKDYWYIV
                                    301                                                        360
CAE47978 Aspergillus furnigatus D12  (249)  LSDG FL VG  LLYY  IGS   YGW  NLL  VWY G  FYLWVN  WLVA  ITEL QH  DP   LPHYQPEA
EAK94955 Candida albicans D12        (268)  LSDG  L LA FTT Y YQKYKNF GLF NMN NMWF VP NLWVN EWLV F VT FL QH TD  TM  HYT KE
EAL03493 Candida albicans D12        (273)  LSDLGIL L QFNL Y VW YQ SFGGF NLLVNYIV LF FLVNNEWLV F ITKLQH CD PO  MPHY  A SQ
AAF08684 Mortierella alpina D12      (249)  LSD G W LAALGA LI  ASMQLSL  W TKYY   V FY L F VNF WLVL ITELCH  DPK  L PHY REG A
                                   Consensus (301)  LSDLGILLAFS LYYWY SFGLLNLLVNYIVFYLWVNHWLVFITFLCHTDPTLPHY A A
                                    361                                                        420
CAE47978 Aspergillus furnigatus D12  (309)  WD TRGA A A TIDR  F GF VG H  HIFHG I  IETHVL  HYVS T PFYHADEA  EA I QKVMGPHY
EAK94955 Candida albicans D12        (328)  WT ARGAAATI DRN F GF VGQ HI F HDI I ETHVL HHY V S R PFY NA RE A  A I RKV MGE HY
EAL03493 Candida albicans D12        (333)  WT ARGAAATIDRW F GFVG K H FHDT I ETHVL HHY VS R PFY NAR EA S A ITKKV MGT HY Q
AAF08684 Mortierella alpina D12      (309)  WN F ORG AL CT V DRS F GKF LD H  H G I VHTHVA HHLF S Q  PFYHAREE A  Y H  K LL GS  Y V
                                   Consensus (361)  WTFARGAAATIDRDFGFVGKHIFHGLIETHVLHHYVSREIPFYNAREASEAIKKVMGEHYR
                                    421                                                476
CAE47978 Aspergillus furnigatus D12  (369)  S  AH G  T GFLK A W  SARTC O V  PTEC AKG  S QYV F   NINGI  V P A  KIPAK    (SEQ ID NO: 17)
EAK94955 Candida albicans D12        (388)    G  RN  Y----S LWKCMRMCO F V D DKED---  A KGVMM  N VNG  GPVK  D---         (SEQ ID NO: 18)
EAL03493 Candida albicans D12        (393)  HSDFNM  V----S LWKSARWCQF V DG S ------N- G VLM  A NTNGF S  D F KK QTH-      (SEQ ID NO: 19)
AAF08684 Mortierella alpina D12      (369)     PSP V Y-  -   K  F R EC    V LD G------DV   F K---------                  (SEQ ID NO: 16)
                                   Consensus (421)  YEAESMWV    ALWKSAR CQFVDDN    A GVLMFRNINGFCV P K
```

Similarity: 83.2%; Identity: 23.9%
CAE47978—Aspergillus furnigatus (424)
EAK94955—Candida albicans (436)
EAL03493—Candida albicans (433)
AAF08684—Mortierella alpina (399)

Figure 6

**Plasmid pSBS4119 for the Expression of Delta-6 Desaturase from *S. diclina***

**Plasmid pSBS4763 for the Expression of Delta-6 Desaturase from *M. alpina***

```
                        SEQUENCE LISTING

<160> NUMBER OF SEQ ID NOS: 19

<210> SEQ ID NO 1
<211> LENGTH: 7803
<212> TYPE: DNA
<213> ORGANISM: Artificial Sequence
<220> FEATURE:
<223> OTHER INFORMATION: Plasmid pSBS4766

<400> SEQUENCE: 1
ctgcaggaat tcgatctcta ttgattcaaa ttacgatctg atactgataa cgtctagatt      60
tttagggtta aagcaatcaa tcacctgacg attcaaggtg gttggatcat gacgattcca     120
gaaaacatca agcaagctct caaagctaca ctctttggga tcatactgaa ctctaacaac     180
ctcgttatgt cccgtagtgc cagtacagac atccctgtaa ctcggattgt gcacgatgcc     240
atgactatac ccaacctcgg tcttggtcac accaggaact ctctggtaag ctagctccac     300
tccccagaaa caaccggcgc caaattgcgc gaattgctga cctgaagacg gaacatcatc     360
```

```
                                                         -continued
gtcgggtcct tgggcgattg cggcggaaga tgggtcagct tgggcttgag gacgagaccc      420
gaatccgagt ctgttgaaaa ggttgttcat tggggatttg tatacggaga ttggtcgtcg      480
agaggtttga gggaaaggac aaatgggttt ggctctggag aaagagagtg cggctttaga      540
gagagaattg agaggtttag agagagatgc ggcggcgatg agcggaggag agacgacgag      600
gacctgcatt atcaaagcag tgacgtggtg aaatttggaa cttttaagag gcagatagat      660
ttattatttg tatccatttt cttcattgtt ctagaatgtc gcggaacaaa ttttaaaact      720
aaatcctaaa tttttctaat tttgttgcca atagtggata tgtgggccgt atagaaggaa      780
tctattgaag gcccaaaccc atactgacga gcccaaaggt tcgttttgcg ttttatgttt      840
cggttcgatg ccaacgccac attctgagct aggcaaaaaa caaacgtgtc tttgaataga      900
ctcctctcgt taacacatgc agcggctgca tggtgacgcc attaacacgt ggcctacaat      960
tgcatgatgt ctccattgac acgtgacttc tcgtctcctt tcttaatata tctaacaaac     1020
actcctacct cttccaaaat atatacacat cttttttgatc aatctctcat tcaaaatctc    1080
attctctcta gtaaacaaga acaaaaaacc atggctgctg ctcccagtgt gaggacgttt     1140
actcgggccg aggttttgaa tgccgaggct ctgaatgagg gcaagaagga tgccgaggca     1200
cccttcttga tgatcatcga caacaaggtg tacgatgtcc gcgagttcgt ccctgatcat     1260
cccggtggaa gtgtgattct cacgcacgtt ggcaaggacg gcactgacgt cttttgacact    1320 tttcaccccg aggctgcttg ggagactctt gccaactttt acgttggtga tattgacgag     1380
agcgaccgcg atatcaagaa tgatgacttt gcggccgagg tccgcaagct gcgtaccttg     1440
ttccagtctc ttggttacta cgattcttcc aaggcatact acgccttcaa ggtctcgttc     1500
aacctctgca tctgggggttt gtcgacggtc attgtggcca agtggggcca gacctcgacc    1560
ctcgccaacg tgctctcggc tgcgcttttg ggtctgttct ggcagcagtg cggatggttg     1620
gctcacgact ttttgcatca ccaggtcttc caggaccgtt tctggggtga tcttttcggc    1680
gccttcttgg gaggtgtctg ccagggcttc tcgtcctcgt ggtggaagga caagcacaac    1740
actcaccacg ccgcccccaa cgtccacggc gaggatcccg acattgacac ccaccctctg    1800
ttgacctgga gtgagcatgc gttggagatg ttctcggatg tcccagatga ggagctgacc    1860
cgcatgtggt cgcgtttcat ggtcctgaac cagacctggt tttacttccc cattctctcg    1920
tttgcccgtc tctcctggtg cctccagtcc attctctttg tgctgcctaa cggtcaggcc     1980
cacaagccct cgggcgcgcg tgtgcccatc tcgttggtcg agcagctgtc gcttgcgatg    2040
cactggacct ggtacctcgc caccatgttc ctgttcatca aggatcccgt caacatgctg    2100 gtgtacttttt tggtgtcgca ggcggtgtgc ggaaacttgt tggcgatcgt gttctcgctc    2160
aaccacaacg gtatgcctgt gatctcgaag gaggaggcgg tcgatatgga tttcttcacg    2220
aagcagatca tcacgggtcg tgatgtccac ccgggtctat ttgccaactg gttcacgggt    2280
ggattgaact atcagatcga gcaccacttg ttcccttcga tgcctcgcca caacttttca    2340
aagatccagc ctgctgtcga gaccctgtgc aaaaagtaca atgtccgata ccacaccacc    2400
ggtatgatcg agggaactgc agaggtcttt agccgtctga cgaggtctc caaggctgcc     2460 tccaagatgg gtaaggcgca gtaagcttgt taccccactg atgtcatcgt catagtccaa    2520
taactccaat gtcggggagt tagttttatga ggaataaagt gtttagaatt tgatcagggg   2580
gagataataa aagccgagtt tgaatctttt tgttataagt aatgtttatg tgtgtttcta    2640
tatgttgtca aatggtccca tgttttttctt cctctctttt tgtaacttgc aagtgttgtg  2700
ttgtacttta tttggcttct ttgtaagttg gtaacggtgg tctatatatg gaaaaggtct    2760
```

```
tgttttgtta aacttatgtt agttaactgg attcgtcttt aaccacaaaa agttttcaat     2820
aagctacaaa tttagacacg caagccgatg cagtcattag tacatatatt tattgcaagt     2880
gattacatgg caacccaaac ttcaaaaaca gtaggttgct ccatttagta acctgaattg     2940
cctcctgatt ctagttgatc ccggtaccga attccaggaa ttcgatctct attgattcaa     3000
attacgatct gatactgata acgtctagat ttttagggtt aaagcaatca atcacctgac     3060
gattcaaggt ggttggatca tgacgattcc agaaaacatc aagcaagctc tcaaagctac     3120
actctttggg atcatactga actctaacaa cctcgttatg tcccgtagtg ccagtacaga     3180
catcctcgta actcggattg tgcacgatgc catgactata cccaacctcg gtcttggtca     3240
caccaggaac tctctggtaa gctagctcca ctccccagaa acaaccggcg ccaaattgcg     3300
cgaattgctg acctgaagac ggaacatcat cgtcgggtcc ttgggcgatt gcggcggaag     3360
atgggtcagc ttgggcttga ggacgagacc cgaatccgag tctgttgaaa aggttgttca     3420
ttggggattt gtatacggag attggtcgtc gagaggtttg agggaaagga caaatggggtt    3480
tggctctgga gaaagagagt gcggctttag agagagaatt gagaggttta gagagagatg     3540
cggcggcgat gagcggagga gagacgacga ggacctgcat tatcaaagca gtgacgtggt     3600
gaaatttgga acttttaaga ggcagataga tttattattt gtatccattt tcttcattgt     3660
tctagaatgt cgcggaacaa attttaaaac taaatcctaa attttttaa ttttgttgcc      3720
aatagtggat atgtgggccg tatagaagga atctattgaa ggcccaaacc catactgacg     3780
agcccaaagg ttcgttttgc gttttatgtt tcggttcgat gccaacgcca cattctgagc     3840
taggcaaaaa acaaacgtgt cttttgaatag actcctctcg ttaacacatg cagcggctgc    3900
atggtgacgc cattaacacg tggcctacaa ttgcatgatg tctccattga cacgtgactt     3960
ctcgtctcct ttcttaatat atctaacaaa cactcctacc tcttccaaaa tatatacaca     4020
tcttttgat caatctctca ttcaaaatct cattctctct agtaaacaag aacaaaaaac       4080
catggcacct cccaacacta tcgatgccgg tttgacccag cgtcatatca gcacctcggc     4140
cccaaactcg gccaagcctg ccttcgagcg caactaccag ctccccgagt tcaccatcaa     4200
ggagatccga gagtgcatcc ctgcccactg cttttgagcgc tccggtctcc gtggtctctg    4260
ccacgttgcc atcgatctga cttgggcgtc gctcttgttc ctggctgcga cccagatcga     4320
caagtttgag aatcccttga tccgctattt ggcctggcct gtttactgga tcatgcaggg     4380
tattgtctgc accggtgtct gggtgctggc tcacgagtgt ggtcatcagt ccttctcgac     4440
ctccaagacc ctcaacaaca cagttggttg gatcttgcac tcgatgctct tggtccccta     4500
ccactcctgg agaatctcgc actcgaagca ccacaaggcc actggccata tgaccaagga     4560
ccaggtcttt gtgcccaaga cccgctccca ggttggcttg cctccaagg agaacgctgc      4620
tgctgccgtt caggaggagg acatgtccgt gcacctggat gaggaggctc ccattgtgac     4680
tttgttctgg atggtgatcc agttcttgtt cggatggccc gcgtacctga ttatgaacgc     4740
ctctggccaa gactacggcc gctggacctc gcacttccac acgtactcgc ccatctttga     4800
gccccgcaac ttttttcgaca ttattatctc ggacctcggt gtgttggctg ccctcggtgc    4860
cctgatctat gcctccatgc agttgtcgct cttgaccgtc accaagtact atattgtccc     4920
ctacctcttt gtcaacttttt ggttggtcct gatcaccttc ttgcagcaca ccgatcccaa    4980
gctgccccat taccgcgagg gtgcctggaa tttccagcgt ggagctcttt gcaccgttga     5040
ccgctcgttt ggcaagttct tggaccatat gttccacggc attgtccaca cccatgtggc     5100
ccatcacttg ttctcgcaaa tgccgttcta ccatgctgag gaagctacct atcatctcaa     5160
```

```
gaaactgctg ggagagtact atgtgtacga cccatccccg atcgtcgttg cggtctggag    5220
gtcgttccgt gagtgccgat tcgtggagga tcagggagac gtggtctttt tcaagaagta    5280
agcttgttac cccactgatg tcatcgtcat agtccaataa ctccaatgtc ggggagttag    5340
tttatgagga ataaagtgtt tagaatttga tcagggggga ataataaaag ccagtttga    5400 atctttttgt tataagtaat gtttatgtgt gtttctatat gttgtcaaat ggtcccatgt    5460
ttttcttcct ctcttttgt aacttgcaag tgttgtgttg tactttattt ggcttctttg     5520
taagttggta acgtggtct atatatggaa aaggtcttgt tttgttaaac ttatgttagt     5580
taactggatt cgtcttaac cacaaaaagt tttcaataag ctacaaattt agacacgcaa     5640
gccgatgcag tcattagtac atatatttat tgcaagtgat tacatggcaa cccaaacttc    5700
aaaaacagta ggttgctcca tttagtaacc tgaattgcct cctgattcta gttgatcccg    5760
gtgaatccaa aaattacgga tatgaatata ggcatatccg tatccgaatt atccgtttga    5820
cagctagcaa cgattgtaca attgcttctt taaaaaagga agaaagaaag aaagaaaaga    5880
atcaacatca gcgttaacaa acggccccgt tacggcccaa acggtcatat agagtaacgg    5940
cgttaagcgt tgaaagactc ctatcgaaat acgtaaccgc aaacgtgtca tagtcagatc    6000
ccctcttcct tcaccgcctc aaacacaaaa ataatcttct acagcctata tatacaaccc    6060 cccttctat ctctccttc tcacaattca tcatctttct ttctctaccc ccaattttaa      6120
gaaatcctct cttctcctct tcattttcaa ggtaaatctc tctctctctc tctctctctg    6180
ttattccttg ttttaattag gtatgtatta ttgctagttt gttaatctgc ttatcttatg    6240
tatgccttat gtgaatatct ttatcttgtt catctcatcc gtttagaagc tataaatttg    6300
ttgatttgac tgtgtatcta cacgtggtta tgtttatatc taatcagata tgaatttctt    6360
catattgttg cgtttgtgtg taccaatccg aaatcgttga ttttttttcat ttaatcgtgt   6420 agctaattgt acgtatacat atggatctac gtatcaattg ttcatctgtt tgtgtttgta   6480
tgtatacaga tctgaaaaca tcacttctct catctgattg tgttgttaca tacatagata    6540
tagatctgtt atatcatttt tttattaatt gtgtatatat atatgtgcat agatctggat    6600
tacatgattg tgattattta catgattttg ttatttacgt atgtatatat gtagatctgg    6660
actttttgga gttgttgact tgattgtatt tgtgtgtgta tatgtgtgtt ctgatcttga    6720
tatgttatgt atgtgcagcc aaggctacgg gcgatccacc atgtctccgg agaggagacc    6780
agttgagatt aggccagcta cagcagctga tatggccgcg gtttgtgata tcgttaacca    6840
ttacattgag acgtctacag tgaactttag gacagagcca caaacaccac aagagtggat    6900
tgatgatcta gagaggttgc aagatagata cccttggttg gttgctgagg ttgagggtgt    6960
tgtggctggt attgcttacg ctgggccctg gaaggctagg aacgcttacg attggacagt    7020
tgagagtact gtttacgtgt cacataggca tcaaaggttg ggcctaggtt ccacattgta    7080
cacacatttg cttaagtcta tggaggcgca aggttttaag tctgtggttg ctgttatagg    7140
ccttccaaac gatccatctg ttaggttgca tgaggctttg ggatacacag cccggggtac    7200
attgcgcgca gctggataca agcatggtgg atggcatgat gttggttttt ggcaaaggga    7260
ttttgagttg ccagctcctc caaggccagt taggccagtt acccagatct gagtcgaccg    7320
aatgagttcc aagatggttt gtgacgaagt tagttggttg tttttatgga actttgttta    7380
agctagcttg taatgtggaa agaacgtgtg gctttgtggt ttttaaatgt tggtgaataa    7440 agatgttttcc tttggattaa ctagtatttt tcctattggt ttcatggttt tagcacacaa    7500
cattttaaat atgctgttag atgatatgct gcctgcttta ttatttactt accctcacc    7560
```

```
ttcagtttca aagttgttgc aatgactctg tgtagtttaa gatcgagtga aagtagattt    7620
tgtctatatt tattaggggt atttgatatg ctaatggtaa acatggttta tgacagcgta    7680
cttttttggt tatggtgttg acgtttcctt ttaaacatta tagtagcgtc cttggtctgt    7740
gttcattggt tgaacaaagg cacactcact tggagatgcc gtctccactg atatttgaac    7800
aaa                                                                  7803

<210> SEQ ID NO 2
<211> LENGTH: 5003
<212> TYPE: DNA
<213> ORGANISM: Artificial Sequence
<220> FEATURE:
<223> OTHER INFORMATION: Plasmid pSBS4119

<400> SEQUENCE: 2
ctgcaggaat tcgatctcta ttgattcaaa ttacgatctg atactgataa cgtctagatt      60
tttagggtta aagcaatcaa tcacctgacg attcaaggtg gttggatcat gacgattcca     120
gaaaacatca agcaagctct caaagctaca ctctttggga tcatactgaa ctctaacaac     180
ctcgttatgt cccgtagtgc cagtacagac atcctcgtaa ctcggattgt gcacgatgcc     240
atgactatac ccaacctcgg tcttggtcac accaggaact ctctggtaag ctagctccac     300
tccccagaaa caaccggcgc caaattgcgc gaattgctga cctgaagacg gaacatcatc     360
gtcgggtcct tgggcgattg cggcggaaga tgggtcagct tgggcttgag gacgagaccc     420
gaatccgagt ctgttgaaaa ggttgttcat tggggatttg tatacggaga ttggtcgtcg     480
agaggtttga gggaaaggac aaatgggttt ggctctggag aaagagagtg cggctttaga     540
gagagaattg agaggtttag agagagatgc ggcggcgatg agcggaggag agacgacgag     600
gacctgcatt atcaaagcag tgacgtggtg aaatttggaa cttttaagag gcagatagat     660
ttattatttg tatccatttt cttcattgtt ctagaatgtc gcggaacaaa ttttaaaact     720
aaatcctaaa tttttctaat tttgttgcca atagtggata tgtgggccgt atagaaggaa     780
tctattgaag gcccaaaccc atactgacga gcccaaaggt tcgttttgcg ttttatgttt     840
cggttcgatg ccaacgccac attctgagct aggcaaaaaa caaacgtgtc tttgaataga     900
ctcctctcgt taacacatgc agcggctgca tggtgacgcc attaacacgt ggcctacaat     960
tgcatgatgt ctccattgac acgtgacttc cgtctccctt tcttaatata tctaacaaac    1020
actcctacct cttccaaaat atatacacat cttttttgatc aatctctcat tcaaaatctc    1080
attctctcta gtaaacaaga acaaaaaacc atggtccagg gcaaaaggc cgagaagatc    1140 tcgtgggcga ccatccgtga gcacaaccgc caagacaacg cgtggatcgt gatccaccac    1200
aaggtgtacg acatctcggc ctttgaggac caccccgggcg cgtcgtcat gttcacgcag    1260 gccggcgaag acgcgaccga tgcgttcgct gtcttccacc cgagctcggc gctcaagctc    1320
ctcgagcagt actacgtcgg cgacgtcgac cagtcgacgg cggccgtcga cacgtcgatc    1380
tcggacgagg tcaagaagag ccagtcggac ttcattgcgt cgtaccgcaa gctgcgcctt    1440
gaagtcaagc gcctcggctt gtacgactcg agcaagctct actacctcta caagtgcgcc    1500
tcgacgctga gcattgcgct tgtgtcggcg gccatttgcc tccactttga ctcgacggcc    1560
atgtacatgg tcgcggctgt catccttggc ctctttttacc agcagtgcgg ctggctcgcc    1620
catgactttc tgcaccacca agtgtttgag aaccacttgt ttggcgacct cgtcggcgtc    1680
atggtcggca acctctggca gggcttctcg gtgcagtggt ggaagaacaa gcacaacacg    1740
caccatgcga tccccaacct ccacgcgacg cccgagatcg ccttccacgg cgaccgggac    1800
```

```
attgacacga tgccgattct cgcgtggtcg ctcaagatgg cgcagcacgc ggtcgactcg   1860
cccgtcgggc tcttcttcat gcgctaccaa gcgtacctgt actttcccat cttgctcttt   1920
gcgcgtatct cgtgggtgat ccagtcggcc atgtacgcct ctacaacgt tgggcccggc    1980
ggcacctttg acaaggtcca gtacccgctg ctcgagcgcg ccggcctcct cctctactac   2040
ggctggaacc tcggccttgt gtacgcagcc aacatgtcgc tgctccaagc ggctgcgttc   2100
ctctttgtga gccaggcgtc gtgcggcctc ttcctcgcga tggtctttag cgtcggccac   2160
aacggcatgg aggtctttga caaggacagc aagcccgatt tttggaagct gcaagtgctc   2220
tcgacgcgca acgtgacgtc gtcgctctgg atcgactggt tcatgggcgg cctcaactac   2280
cagatcgacc accacttgtt cccgatggtg ccccggcaca acctcccggc gctcaacgtg   2340
ctcgtcaagt cgctctgcaa gcagtacgac atcccatacc acgagacggg cttcatcgcg   2400
ggcatggccg aggtcgtcgt gcacctcgag cgcatctcga tcgagttctt caaggagttt   2460
cccgccatgt aagcttgtta ccccactgat gtcatcgtca tagtccaata actccaatgt   2520
cggggagtta gtttatgagg aataaagtgt ttagaatttg atcaggggga gataataaaa   2580
gccgagtttg aatcttttg ttataagtaa tgtttatgtg tgtttctata tgttgtcaaa    2640
tggtcccatg ttttcttcc tctctttttg taacttgcaa gtgttgtgtt gtactttatt    2700
tggcttcttt gtaagttggt aacggtggtc tatatatgga aaaggtcttg ttttgttaaa   2760
cttatgttag ttaactggat tcgtctttaa ccacaaaaag ttttcaataa gctacaaatt   2820
tagacacgca agccgatgca gtcattagta catatattta ttgcaagtga ttacatggca   2880
acccaaactt caaaaacagt aggttgctcc atttagtaac ctgaattgcc tcctgattct   2940
agttgatccc ggtaccgaat tcgaatccaa aaattacgga tatgaatata ggcatatccg   3000
tatccgaatt atccgtttga cagctagcaa cgattgtaca attgcttctt taaaaaagga   3060
agaaagaaag aaagaaaaga atcaacatca gcgttaacaa acggcccgt tacgcccaa     3120
acggtcatat agagtaacgg cgttaagcgt tgaaagactc ctatcgaaat acgtaaccgc   3180
aaacgtgtca tagtcagatc ccctcttcct tcaccgcctc aaacacaaaa ataatcttct   3240
acagcctata tatacaaccc ccccttctat ctctcctttc tcacaattca tcatctttct   3300
ttctctaccc ccaatttaa gaaatcctct cttctcctct tcatttcaa ggtaaatctc     3360
tctctctctc tctctctctg ttattccttg ttttaattag gtatgtatta ttgctagttt   3420
gttaatctgc ttatcttatg tatgccttat gtgaatatct ttatcttgtt catctcatcc   3480
gtttagaagc tataaatttg ttgatttgac tgtgtatcta cacgtggtta tgtttatatc   3540
taatcagata tgaatttctt catattgttg cgtttgtgtg taccaatccg aaatcgttga   3600
ttttttcat ttaatcgtgt agctaattgt acgtatacat atggatctac gtatcaattg    3660
ttcatctgtt tgtgtttgta tgtatacaga tctgaaaaca tcacttctct catctgattg   3720
tgttgttaca tacatagata tagatctgtt atatcatttt tttattaatt gtgtatatat   3780
atatgtgcat agatctggat tacatgattg tgattattta catgattttg ttatttacgt   3840
atgtatatat gtagatctgg acttttggg gttgttgact tgattgtatt tgtgtgtgta    3900
tatgtgtgtt ctgatcttga tatgttatgt atgtgcagcc aaggctacgg gcgatccacc   3960
atgtctccgg agaggagacc agttgagatt aggccagcta cagcagctga tatggccgcg   4020
gtttgtgata tcgttaacca ttacattgag acgtctacag tgaactttag gacagagcca   4080
caaacaccac aagagtggat tgatgatcta gagaggttgc aagatagata cccttggttg   4140
gttgctgagg ttgagggtgt tgtggctggt attgcttacg ctgggccctg gaaggctagg   4200
```

-continued

| | |
|---|---|
| aacgcttacg attggacagt tgagagtact gtttacgtgt cacataggca tcaaaggttg | 4260 |
| ggcctaggtt ccacattgta cacacatttg cttaagtcta tggaggcgca aggttttaag | 4320 |
| tctgtggttg ctgttatagg ccttccaaac gatccatctg ttaggttgca tgaggctttg | 4380 |
| ggatacacag cccggggtac attgcgcgca gctggataca agcatggtgg atggcatgat | 4440 |
| gttggttttt ggcaaaggga ttttgagttg ccagctcctc caaggccagt taggccagtt | 4500 |
| acccagatct gagtcgaccg aatgagttcc aagatggttt tgacgaagt tagttggttg | 4560 |
| tttttatgga actttgttta agctagcttg taatgtggaa agaacgtgtg ctttgtggt | 4620 |
| ttttaaatgt tggtgaataa agatgttccc tttggattaa ctagtatttt tcctattggt | 4680 |
| ttcatggttt tagcacacaa cattttaaat atgctgttag atgatatgct gcctgcttta | 4740 |
| ttatttactt accccctcacc ttcagtttca aagttgttgc aatgactctg tgtagtttaa | 4800 |
| gatcgagtga agtagatttt tgtctatatt tattaggggt atttgatatg ctaatggtaa | 4860 |
| acatggttta tgacagcgta cttttttggt tatggtgttg acgtttcctt ttaaacatta | 4920 |
| tagtagcgtc cttggtctgt gttcattggt tgaacaaagg cacactcact tggagatgcc | 4980 |
| gtctccactg atatttgaac aaa | 5003 |

<210> SEQ ID NO 3
<211> LENGTH: 5013
<212> TYPE: DNA
<213> ORGANISM: Artificial Sequence
<220> FEATURE:
<223> OTHER INFORMATION: Plasmid pSBS4763

<400> SEQUENCE: 3

| | |
|---|---|
| ctgcaggaat tcgatctcta ttgattcaaa ttacgatctg atactgataa cgtctagatt | 60 |
| tttagggtta aagcaatcaa tcacctgacg attcaaggtg gttggatcat gacgattcca | 120 |
| gaaaacatca agcaagctct caaagctaca ctctttggga tcatactgaa ctctaacaac | 180 |
| ctcgttatgt cccgtagtgc cagtacagac atcctcgtaa ctcggattgt gcacgatgcc | 240 |
| atgactatac ccaacctcgg tcttggtcac accaggaact ctctggtaag ctagctccac | 300 |
| tccccagaaa caaccggcgc caaattgcgc gaattgctga cctgaagacg aaacatcatc | 360 |
| gtcgggtcct tgggcgattg cggcggaaga tgggtcagct tgggcttgag gacgagaccc | 420 |
| gaatccgagt ctgttgaaaa ggttgttcat tgggatttg tatacggaga ttggtcgtcg | 480 |
| agaggtttga gggaaaggac aaatgggttt ggctctggag aaagagagtg cggctttaga | 540 |
| gagagaattg agaggtttag agagagatgc ggcggcgatg agcggaggag agacgacgag | 600 |
| gacctgcatt atcaaagcag tgacgtggtg aaatttggaa cttttaagag gcagatagat | 660 |
| ttattatttg tatccatttt cttcattgtt ctagaatgtc gcggaacaaa ttttaaaact | 720 |
| aaatcctaaa ttttctaat tttgttgcca atagtggata tgtgggccgt atagaaggaa | 780 |
| tctattgaag gcccaaaccc atactgacga gcccaaaggt tcgttttgcg ttttatgttt | 840 |
| cggttcgatg ccaacgccac attctgagct aggcaaaaaa caaacgtgtc tttgaataga | 900 |
| ctcctctcgt taacacatgc agcggctgca tggtgacgcc attaacacgt ggcctacaat | 960 |
| tgcatgatgt ctccattgac acgtgacttc tcgtctcctt tcttaatata tctaacaaac | 1020 |
| actcctacct cttccaaaat atatacacat cttttgatc aatctctcat tcaaaatctc | 1080 |
| attctctcta gtaaacaaga acaaaaaacc atggctgctg ctcccagtgt gaggacgttt | 1140 |
| actcgggccg aggttttgaa tgccgaggct ctgaatgagg caagaagga tgccgaggca | 1200 |
| cccttcttga tgatcatcga caacaaggtg tacgatgtcc gcgagttcgt ccctgatcat | 1260 |

-continued

```
cccggtggaa gtgtgattct cacgcacgtt ggcaaggacg gcactgacgt ctttgacact    1320
tttcaccccg aggctgcttg ggagactctt gccaacttt acgttggtga tattgacgag    1380
agcgaccgcg atatcaagaa tgatgacttt gcggccgagg tccgcaagct gcgtaccttg    1440
ttccagtctc ttggttacta cgattcttcc aaggcatact acgccttcaa ggtctcgttc    1500
aacctctgca tctgggggttt gtcgacggtc attgtggcca agtggggcca gacctcgacc    1560
ctcgccaacg tgctctcggc tgcgcttttg ggtctgttct ggcagcagtg cggatggttg    1620
gctcacgact ttttgcatca ccaggtcttc caggaccgtt tctggggtga tcttttcggc    1680
gccttcttgg gaggtgtctg ccagggcttc tcgtcctcgt ggtggaagga caagcacaac    1740
actcaccacg ccgcccccaa cgtccacggc gaggatcccg acattgacac ccaccctctg    1800
ttgacctgga gtgagcatgc gttggagatg ttctcggatg tcccagatga ggagctgacc    1860
cgcatgtggt cgcgtttcat ggtcctgaac cagacctggt tttacttccc cattctctcg    1920
tttgcccgtc tctcctggtg cctccagtcc attctctttg tgctgcctaa cggtcaggcc    1980
cacaagccct cgggcgcgcg tgtgcccatc tcgttggtcg agcagctgtc gcttgcgatg    2040
cactggacct ggtacctcgc caccatgttc ctgttcatca aggatcccgt caacatgctg    2100
gtgtactttt tggtgtcgca ggcggtgtgc ggaaacttgt tggcgatcgt gttctcgctc    2160
aaccacaacg gtatgcctgt gatctcgaag gaggaggcgg tcgatatgga tttcttcacg    2220
aagcagatca tcacgggtcg tgatgtccac ccgggtctat ttgccaactg gttcacgggt    2280
ggattgaact atcagatcga gcaccacttg ttcccttcga tgcctcgcca caacttttca    2340
aagatccagc ctgctgtcga gaccctgtgc aaaaagtaca atgtccgata ccacaccacc    2400
ggtatgatcg agggaactgc agaggtcttt agccgtctga acgaggtctc caaggctgcc    2460
tccaagatgg gtaaggcgca gtaagcttgt taccccactg atgtcatcgt catagtccaa    2520
taactccaat gtcggggagt tagtttatga ggaataaagt gtttagaatt tgatcagggg    2580
gagataataa aagccgagtt tgaatctttt tgttataagt aatgtttatg tgtgtttcta    2640
tatgttgtca aatggtccca tgttttttctt cctctctttt tgtaacttgc aagtgttgtg    2700
ttgtactta tttggcttct ttgtaagttg gtaacggtgg tctatatatg gaaaaggtct    2760
tgttttgtta aacttatgtt agttaactgg attcgtcttt aaccacaaaa agttttcaat    2820
aagctacaaa tttagacacg caagccgatg cagtcattag tacatatatt tattgcaagt    2880
gattacatgg caacccaaac ttcaaaaaca gtaggttgct ccatttagta acctgaattg    2940
cctcctgatt ctagttgatc ccggtaccga attcgaatcc aaaaattacg gatatgaata    3000
taggcatatc cgtatccgaa ttatccgttt gacagctagc aacgattgta caattgcttc    3060
tttaaaaaag gaagaaagaa agaaagaaaa gaatcaacat cagcgttaac aaacggcccc    3120
gttacggccc aaacggtcat atagagtaac ggcgttaagc gttgaaagac tcctatcgaa    3180
atacgtaacc gcaaacgtgt catagtcaga tcccctcttc cttcaccgcc tcaaacacaa    3240
aaataatctt ctacagccta tatatacaac cccccttct atctctcctt tctcacaatt    3300
catcatcttt ctttctctac ccccaatttt aagaaatcct ctcttctcct cttcattttc    3360
aaggtaaatc tctctctctc tctctctctc tgttattcct tgttttaatt aggtatgtat    3420
tattgctagt ttgttaatct gcttatctta tgtatgcctt atgtgaatat ctttatcttg    3480
ttcatctcat ccgtttagaa gctataaatt tgttgatttg actgtgtatc tacacgtggt    3540
tatgtttata tctaatcaga tatgaatttc ttcatattgt tgcgtttgtg tgtaccaatc    3600
cgaaatcgtt gatttttttc atttaatcgt gtagctaatt gtacgtatac atatggatct    3660
```

-continued

```
acgtatcaat tgttcatctg tttgtgtttg tatgtataca gatctgaaaa catcacttct    3720
ctcatctgat tgtgttgtta catacataga tatagatctg ttatatcatt tttttattaa    3780
ttgtgtatat atatatgtgc atagatctgg attacatgat tgtgattatt tacatgattt    3840
tgttatttac gtatgtatat atgtagatct ggactttttg gagttgttga cttgattgta    3900
tttgtgtgtg tatatgtgtg ttctgatctt gatatgttat gtatgtgcag ccaaggctac    3960
gggcgatcca ccatgtctcc ggagaggaga ccagttgaga ttaggccagc tacagcagct    4020
gatatggccg cggtttgtga tatcgttaac cattacattg agacgtctac agtgaacttt    4080
aggacagagc cacaaacacc acaagagtgg attgatgatc tagagaggtt gcaagataga    4140 taccccttggt tggttgctga ggttgagggt gttgtggctg gtattgctta cgctgggccc    4200
tggaaggcta ggaacgctta cgattggaca gttgagagta ctgtttacgt gtcacatagg    4260
catcaaaggt tgggcctagg ttccacattg tacacacatt tgcttaagtc tatggaggcg    4320
caaggtttta agtctgtggt tgctgttata ggccttccaa acgatccatc tgttaggttg    4380
catgaggctt tgggatacac agcccgsgggt acattgcgcg cagctggata caagcatggt    4440
ggatggcatg atgttggttt ttggcaaagg gattttgagt tgccagctcc tccaaggcca    4500
gttaggccag ttacccagat ctgagtcgac cgaatgagtt ccaagatggt ttgtgacgaa    4560
gttagttggt tgtttttatg gaactttgtt taagctagct tgtaatgtgg aaagaacgtg    4620
tggctttgtg gtttttaaat gttggtgaat aaagatgttt cctttggatt aactagtatt    4680
tttcctattg gtttcatggt tttagcacac aacattttaa atatgctgtt agatgatatg    4740
ctgcctgctt tattatttac ttacccctca ccttcagttt caaagttgtt gcaatgactc    4800
tgtgtagttt aagatcgagt gaaagtagat tttgtctata tttattaggg gtatttgata    4860
tgctaatggt aaacatggtt tatgacagcg tactttttttg gttatggtgt tgacgtttcc    4920
ttttaaacat tatagtagcg tccttggtct gtgttcattg gttgaacaaa ggcacactca    4980
cttggagatg ccgtctccac tgatatttga aca                                 5013
```

<210> SEQ ID NO 4
<211> LENGTH: 448
<212> TYPE: PRT
<213> ORGANISM: Borago officinalis

<400> SEQUENCE: 4

```
Met Ala Ala Gln Ile Lys Lys Tyr Ile Thr Ser Asp Glu Leu Lys Asn
  1               5                  10                  15

His Asp Lys Pro Gly Asp Leu Trp Ile Ser Ile Gln Gly Lys Ala Tyr
             20                  25                  30

Asp Val Ser Asp Trp Val Lys Asp His Pro Gly Gly Ser Phe Pro Leu
         35                  40                  45

Lys Ser Leu Ala Gly Gln Glu Val Thr Asp Ala Phe Val Ala Phe His
     50                  55                  60

Pro Ala Ser Thr Trp Lys Asn Leu Asp Lys Phe Phe Thr Gly Tyr Tyr
 65                  70                  75                  80

Leu Lys Asp Tyr Ser Val Ser Glu Val Ser Lys Asp Tyr Arg Lys Leu
                 85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
    130                 135                 140
```

```
Cys Leu Met Gly Phe Leu Trp Ile Gln Ser Gly Trp Ile Gly His Asp
145                 150                 155                 160

Ala Gly His Tyr Met Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190

Lys Trp Asn His Asn Ala His His Ile Ala Cys Asn Ser Leu Glu Tyr
                195                 200                 205

Asp Pro Asp Leu Gln Tyr Ile Pro Phe Leu Val Val Ser Ser Lys Phe
            210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
            260                 265                 270

Leu Leu Thr Lys Arg Asn Val Ser Tyr Arg Ala His Glu Leu Leu Gly
        275                 280                 285

Cys Leu Val Phe Ser Ile Trp Tyr Pro Leu Leu Val Ser Cys Leu Pro
            290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                325                 330                 335

Tyr Val Gly Lys Pro Lys Gly Asn Asn Trp Phe Glu Lys Gln Thr Asp
            340                 345                 350

Gly Thr Leu Asp Ile Ser Cys Pro Pro Trp Met Asp Trp Phe His Gly
        355                 360                 365

Gly Leu Gln Phe Gln Ile Glu His His Leu Phe Pro Lys Met Pro Arg
        370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
            420                 425                 430

Lys Pro Leu Pro Lys Asn Leu Val Trp Glu Ala Leu His Thr His Gly
        435                 440                 445

<210> SEQ ID NO 5
<211> LENGTH: 453
<212> TYPE: PRT
<213> ORGANISM: Primula farinosa

<400> SEQUENCE: 5

Met Ala Asn Lys Ser Pro Pro Asn Pro Lys Thr Gly Tyr Ile Thr Ser
1               5                   10                  15

Ser Asp Leu Lys Ser His Asn Lys Ala Gly Asp Leu Trp Ile Ser Ile
            20                  25                  30

His Gly Gln Val Tyr Asp Val Ser Ser Trp Ala Ala Leu His Pro Gly
        35                  40                  45

Gly Thr Ala Pro Leu Met Ala Leu Ala Gly His Asp Val Thr Asp Ala
    50                  55                  60

Phe Leu Ala Tyr His Pro Pro Ser Thr Ala Arg Leu Leu Pro Pro Leu
65                  70                  75                  80
```

Ser Thr Asn Leu Leu Leu Gln Asn His Ser Val Ser Pro Thr Ser Ser
                85                  90                  95

Asp Tyr Arg Lys Leu Leu Asp Asn Phe His Lys His Gly Leu Phe Arg
            100                 105                 110

Ala Arg Gly His Thr Ala Tyr Ala Thr Phe Val Phe Met Ile Ala Met
        115                 120                 125

Phe Leu Met Ser Val Thr Gly Val Leu Cys Ser Asp Ser Ala Trp Val
    130                 135                 140

His Leu Ala Ser Gly Gly Ala Met Gly Phe Ala Trp Ile Gln Cys Gly
145                 150                 155                 160

Trp Ile Gly His Asp Ser Gly His Tyr Arg Ile Met Ser Asp Arg Lys
                165                 170                 175

Trp Asn Trp Phe Ala Gln Ile Leu Ser Thr Asn Cys Leu Gln Gly Ile
            180                 185                 190

Ser Ile Gly Trp Trp Lys Trp Asn His Asn Ala His His Ile Ala Cys
        195                 200                 205

Asn Ser Leu Asp Tyr Asp Pro Asp Leu Gln Tyr Ile Pro Leu Leu Val
    210                 215                 220

Val Ser Pro Lys Phe Phe Asn Ser Leu Thr Ser Arg Phe Tyr Asp Lys
225                 230                 235                 240

Lys Leu Asn Phe Asp Gly Val Ser Arg Phe Leu Val Cys Tyr Gln His
                245                 250                 255

Trp Thr Phe Tyr Pro Val Met Cys Val Ala Arg Leu Asn Met Leu Ala
            260                 265                 270

Gln Ser Phe Ile Thr Leu Phe Ser Ser Arg Glu Val Cys His Arg Ala
        275                 280                 285

Gln Glu Val Phe Gly Leu Ala Val Phe Trp Val Trp Phe Pro Leu Leu
    290                 295                 300

Leu Ser Cys Leu Pro Asn Trp Gly Glu Arg Ile Met Phe Leu Leu Ala
305                 310                 315                 320

Ser Tyr Ser Val Thr Gly Ile Gln His Val Gln Phe Ser Leu Asn His
                325                 330                 335

Phe Ser Ser Asp Val Tyr Val Gly Pro Val Gly Asn Asp Trp Phe
            340                 345                 350

Lys Lys Gln Thr Ala Gly Thr Leu Asn Ile Ser Cys Pro Ala Trp Met
        355                 360                 365

Asp Trp Phe His Gly Gly Leu Gln Phe Gln Val Glu His His Leu Phe
    370                 375                 380

Pro Arg Met Pro Arg Gly Gln Phe Arg Lys Ile Ser Pro Phe Val Arg
385                 390                 395                 400

Asp Leu Cys Lys Lys His Asn Leu Pro Tyr Asn Ile Ala Ser Phe Thr
                405                 410                 415

Lys Ala Asn Val Phe Thr Leu Lys Thr Leu Arg Asn Thr Ala Ile Glu
            420                 425                 430

Ala Arg Asp Leu Ser Asn Pro Leu Pro Lys Asn Met Val Trp Glu Ala
        435                 440                 445

Leu Lys Thr Leu Gly
    450

<210> SEQ ID NO 6
<211> LENGTH: 453
<212> TYPE: PRT
<213> ORGANISM: Primula vialli

<400> SEQUENCE: 6

```
Met Ala Asn Lys Ser Pro Pro Asn Pro Lys Thr Gly Tyr Ile Thr Ser
1               5                   10                  15

Ser Asp Leu Lys Gly His Asn Lys Ala Gly Asp Leu Trp Ile Ser Ile
            20                  25                  30

His Gly Glu Val Tyr Asp Val Ser Trp Ala Gly Leu His Pro Gly
        35                  40                  45

Gly Ser Ala Pro Leu Met Ala Leu Ala Gly His Asp Val Thr Asp Ala
50                  55                  60

Phe Leu Ala Tyr His Pro Pro Ser Thr Ala Arg Leu Leu Pro Pro Leu
65                  70                  75                  80

Ser Thr Asn Leu Leu Leu Gln Asn His Ser Val Ser Pro Thr Ser Ser
                85                  90                  95

Asp Tyr Arg Lys Leu Leu His Asn Phe His Lys Ile Gly Met Phe Arg
            100                 105                 110

Ala Arg Gly His Thr Ala Tyr Ala Thr Phe Val Ile Met Ile Val Met
        115                 120                 125

Phe Leu Thr Ser Val Thr Gly Val Leu Cys Ser Asp Ser Ala Trp Val
130                 135                 140

His Leu Ala Ser Gly Ala Ala Met Gly Phe Ala Trp Ile Gln Cys Gly
145                 150                 155                 160

Trp Ile Gly His Asp Ser Gly His Tyr Arg Ile Met Ser Asp Arg Lys
            165                 170                 175

Trp Asn Trp Phe Ala Gln Val Leu Ser Thr Asn Cys Leu Gln Gly Ile
        180                 185                 190

Ser Ile Gly Trp Trp Lys Trp Asn His Asn Ala His His Ile Ala Cys
    195                 200                 205

Asn Ser Leu Asp Tyr Asp Pro Asp Leu Gln Tyr Ile Pro Leu Leu Val
    210                 215                 220

Val Ser Pro Lys Phe Phe Asn Ser Leu Thr Ser Arg Phe Tyr Asp Lys
225                 230                 235                 240

Lys Leu Asn Phe Asp Gly Val Ser Arg Phe Leu Val Cys Tyr Gln His
            245                 250                 255

Trp Thr Phe Tyr Pro Val Met Cys Val Ala Arg Leu Asn Met Ile Ala
        260                 265                 270

Gln Ser Phe Ile Thr Leu Phe Ser Ser Arg Glu Val Gly His Arg Ala
    275                 280                 285

Gln Glu Ile Phe Gly Leu Ala Val Phe Val Trp Phe Pro Leu Leu
290                 295                 300

Leu Ser Cys Leu Pro Asn Trp Ser Glu Arg Ile Met Phe Leu Leu Ala
305                 310                 315                 320

Ser Tyr Ser Val Thr Gly Ile Gln His Val Gln Phe Ser Leu Asn His
            325                 330                 335

Phe Ser Ser Asp Val Tyr Val Gly Pro Pro Val Ala Asn Asp Trp Phe
        340                 345                 350

Lys Lys Gln Thr Ala Gly Thr Leu Asn Ile Ser Cys Pro Ala Trp Met
    355                 360                 365

Asp Trp Phe His Gly Gly Leu Gln Phe Gln Val Glu His His Leu Phe
    370                 375                 380

Pro Arg Met Pro Arg Gly Gln Phe Arg Lys Ile Ser Pro Phe Val Arg
385                 390                 395                 400

Asp Leu Cys Lys Lys His Asn Leu Pro Tyr Asn Ile Ala Ser Phe Thr
            405                 410                 415

Lys Ala Asn Val Leu Thr Leu Lys Thr Leu Arg Asn Thr Ala Ile Glu
```

```
                420             425             430
Ala Arg Asp Leu Ser Asn Pro Thr Pro Lys Asn Met Val Trp Glu Ala
                435             440             445
Val His Thr His Gly
        450

<210> SEQ ID NO 7
<211> LENGTH: 457
<212> TYPE: PRT
<213> ORGANISM: Mortierella alpina

<400> SEQUENCE: 7

Met Ala Ala Ala Pro Ser Val Arg Thr Phe Thr Arg Ala Glu Val Leu
1               5                   10                  15
Asn Ala Glu Ala Leu Asn Glu Gly Lys Lys Asp Ala Glu Ala Pro Phe
                20                  25                  30
Leu Met Ile Ile Asp Asn Lys Val Tyr Asp Val Arg Glu Phe Val Pro
                35                  40                  45
Asp His Pro Gly Gly Ser Val Ile Leu Thr His Val Gly Lys Asp Gly
            50                  55                  60
Thr Asp Val Phe Asp Thr Phe His Pro Glu Ala Ala Trp Glu Thr Leu
65                  70                  75                  80
Ala Asn Phe Tyr Val Gly Asp Ile Asp Glu Ser Asp Arg Asp Ile Lys
                85                  90                  95
Asn Asp Asp Phe Ala Ala Glu Val Arg Lys Leu Arg Thr Leu Phe Gln
                100                 105                 110
Ser Leu Gly Tyr Tyr Asp Ser Ser Lys Ala Tyr Tyr Ala Phe Lys Val
            115                 120                 125
Ser Phe Asn Leu Cys Ile Trp Gly Leu Ser Thr Val Ile Val Ala Lys
        130                 135                 140
Trp Gly Gln Thr Ser Thr Leu Ala Asn Val Leu Ser Ala Ala Leu Leu
145                 150                 155                 160
Gly Leu Phe Trp Gln Gln Cys Gly Trp Leu Ala His Asp Phe Leu His
                165                 170                 175
His Gln Val Phe Gln Asp Arg Phe Trp Gly Asp Leu Phe Gly Ala Phe
                180                 185                 190
Leu Gly Gly Val Cys Gln Gly Phe Ser Ser Ser Trp Trp Lys Asp Lys
            195                 200                 205
His Asn Thr His His Ala Ala Pro Asn Val His Gly Glu Asp Pro Asp
        210                 215                 220
Ile Asp Thr His Pro Leu Leu Thr Trp Ser Glu His Ala Leu Glu Met
225                 230                 235                 240
Phe Ser Asp Val Pro Asp Glu Glu Leu Thr Arg Met Trp Ser Arg Phe
                245                 250                 255
Met Val Leu Asn Gln Thr Trp Phe Tyr Phe Pro Ile Leu Ser Phe Ala
                260                 265                 270
Arg Leu Ser Trp Cys Leu Gln Ser Ile Leu Phe Val Leu Pro Asn Gly
            275                 280                 285
Gln Ala His Lys Pro Ser Gly Ala Arg Val Pro Ile Ser Leu Val Glu
        290                 295                 300
Gln Leu Ser Leu Ala Met His Trp Thr Trp Tyr Leu Ala Thr Met Phe
305                 310                 315                 320
Leu Phe Ile Lys Asp Pro Val Asn Met Leu Val Tyr Phe Leu Val Ser
                325                 330                 335
Gln Ala Val Cys Gly Asn Leu Leu Ala Ile Val Phe Ser Leu Asn His
```

```
            340                 345                 350
Asn Gly Met Pro Val Ile Ser Lys Glu Glu Ala Val Asp Met Asp Phe
            355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
            435                 440                 445

Ala Ala Ser Lys Met Gly Lys Ala Gln
        450                 455

<210> SEQ ID NO 8
<211> LENGTH: 523
<212> TYPE: PRT
<213> ORGANISM: Mucor circinelloides

<400> SEQUENCE: 8

Met Pro Pro Asn Thr Ala Ala Asp Arg Leu Leu Ser Ser Thr Ser Thr
1               5                   10                  15

Arg Ser Ser Asn Ile Val Thr Glu Glu Lys Phe Gln Glu Leu Ile Lys
            20                  25                  30

Gln Gly Asp Ser Val Phe Ile Tyr Glu Gln Lys Val Tyr Arg Val Asn
        35                  40                  45

Asn Phe Met Ala Lys His Pro Gly Gly Glu Ala Ala Leu Arg Ser Ala
    50                  55                  60

Leu Gly Arg Asp Val Thr Asp Glu Ile Arg Thr Met His Pro Pro Gln
65                  70                  75                  80

Val Tyr Glu Lys Met Ile Asn Leu Tyr Cys Ile Gly Asp Tyr Met Pro
                85                  90                  95

Asp Val Ile Arg Pro Ala Ser Met Lys Gln Gln His Thr Phe Thr Lys
            100                 105                 110

Pro Lys Glu Asp Lys Pro Val Leu Thr Ala Thr Trp Glu Gly Gly Phe
        115                 120                 125

Thr Val Gln Ala Tyr Asp Asp Ala Ile Gln Asp Leu His Lys His His
    130                 135                 140

Ser His Asp Leu Ile Lys Asp Ala Val Leu Gln Lys Asp Leu Asn Gly
145                 150                 155                 160

Asp Gln Ile Arg Asn Ala Tyr Arg Lys Leu Glu Ala Glu Leu Tyr Ala
                165                 170                 175

Lys Gly Leu Phe Lys Cys Asn Tyr Trp Lys Tyr Ala Arg Glu Gly Cys
            180                 185                 190

Arg Tyr Thr Leu Leu Ile Phe Leu Ser Leu Trp Phe Thr Leu Lys Gly
        195                 200                 205

Thr Glu Thr Trp His Tyr Met Ala Gly Ala Ala Phe Met Ala Met Phe
    210                 215                 220

Trp His Gln Leu Val Phe Thr Ala His Asp Ala Gly His Asn Glu Ile
225                 230                 235                 240

Thr Gly Lys Ser Glu Ile Asp His Val Ile Gly Val Ile Ile Ala Asn
                245                 250                 255

Phe Ile Gly Gly Leu Ser Leu Gly Trp Trp Lys Asp Asn His Asn Val
```

```
                260                 265                 270
His His Ile Val Thr Asn His Pro Glu His Asp Pro Asp Ile Gln His
            275                 280                 285

Val Pro Phe Met Ala Ile Thr Thr Lys Phe Phe Asn Asn Ile Tyr Ser
290                 295                 300

Thr Tyr Tyr Lys Arg Val Leu Pro Phe Asp Ala Ala Ser Arg Phe Phe
305                 310                 315                 320

Val Arg His Gln His Tyr Leu Tyr Tyr Leu Ile Leu Ser Phe Gly Arg
            325                 330                 335

Phe Asn Leu His Arg Leu Ser Phe Ala Tyr Leu Leu Thr Cys Lys Asn
            340                 345                 350

Val Arg Thr Arg Thr Leu Glu Leu Val Gly Ile Thr Phe Phe Phe Val
            355                 360                 365

Trp Phe Gly Ser Leu Leu Ser Thr Leu Pro Thr Trp Asn Ile Arg Ile
            370                 375                 380

Ala Tyr Ile Met Val Ser Tyr Met Leu Thr Phe Pro Leu His Val Gln
385                 390                 395                 400

Ile Thr Leu Ser His Phe Gly Met Ser Thr Glu Asp Arg Gly Pro Asp
                405                 410                 415

Glu Pro Phe Pro Ala Lys Met Leu Arg Thr Thr Met Asp Val Asp Cys
            420                 425                 430

Pro Glu Trp Leu Asp Trp Phe His Gly Gly Leu Gln Tyr Gln Ala Val
            435                 440                 445

His His Leu Phe Pro Arg Leu Pro Arg His Asn Leu Arg Gln Cys Val
            450                 455                 460

Pro Leu Val Lys Lys Phe Cys Asp Glu Val Gly Leu His Tyr Tyr Met
465                 470                 475                 480

Tyr Asn Phe Ser Thr Gly Asn Gly Val Val Leu Gly Thr Leu Lys Ser
                485                 490                 495

Val Ala Asp Gln Val Gly Phe Met Asn Glu Val Ala Lys Ser Asn Ala
            500                 505                 510

Glu Ile Trp Ala Asn Asp Lys Glu His Ala His
            515                 520
```

<210> SEQ ID NO 9
<211> LENGTH: 456
<212> TYPE: PRT
<213> ORGANISM: Thraustochytrium aureum

<400> SEQUENCE: 9

```
Met Gly Arg Gly Gly Glu Lys Ser Glu Val Asp Gln Val Gln Pro Gln
1               5                   10                  15

Lys Thr Glu Gln Leu Gln Lys Ala Lys Trp Asp Val Val Arg Ile
            20                  25                  30

Asn Gly Val Glu Tyr Asp Val Thr Asp Tyr Leu Arg Lys His Pro Gly
            35                  40                  45

Gly Ser Val Ile Lys Tyr Gly Leu Ala Asn Thr Gly Ala Asp Ala Thr
        50                  55                  60

Ser Leu Phe Glu Ala Phe His Met Arg Ser Lys Lys Ala Gln Met Val
65                  70                  75                  80

Leu Lys Ser Leu Pro Lys Arg Ala Pro Val Leu Glu Ile Gln Pro Asn
                85                  90                  95

Gln Leu Pro Glu Glu Gln Thr Lys Glu Ala Glu Met Leu Arg Asp Phe
            100                 105                 110

Lys Lys Phe Glu Asp Glu Ile Arg Arg Asp Gly Leu Met Glu Pro Ser
```

```
                115                 120                 125
        Phe Trp His Arg Ala Tyr Arg Leu Ser Glu Leu Val Gly Met Phe Thr
        130                 135                 140

Leu Gly Leu Tyr Leu Phe Ser Leu Asn Thr Pro Leu Ser Ile Ala Ala
        145                 150                 155                 160

Gly Val Leu Val His Gly Leu Phe Gly Ala Phe Cys Gly Trp Cys Gln
                            165                 170                 175

His Glu Ala Gly His Gly Ser Phe Phe Tyr Ser Leu Trp Trp Gly Lys
                        180                 185                 190

Arg Val Gln Ala Met Leu Ile Gly Phe Gly Leu Gly Thr Ser Gly Asp
                    195                 200                 205

Met Trp Asn Met Met His Asn Lys His His Ala Ala Thr Gln Lys Val
        210                 215                 220

His His Asp Leu Asp Ile Asp Thr Thr Pro Phe Val Ala Phe Phe Asn
        225                 230                 235                 240

Thr Ala Phe Glu Lys Asn Arg Trp Lys Gly Phe Ser Lys Ala Trp Val
                            245                 250                 255

Arg Phe Gln Ala Phe Thr Phe Ile Pro Val Thr Ser Gly Met Ile Val
                        260                 265                 270

Met Leu Phe Trp Leu Phe Phe Leu His Pro Arg Arg Val Val Gln Lys
                    275                 280                 285

Lys Asn Phe Glu Glu Gly Phe Trp Met Leu Ser Ser His Ile Val Arg
        290                 295                 300

Thr Tyr Leu Phe His Leu Val Thr Gly Trp Glu Ser Leu Ala Ala Cys
        305                 310                 315                 320

Tyr Leu Val Gly Tyr Trp Ala Cys Met Trp Val Ser Gly Met Tyr Leu
                            325                 330                 335

Phe Gly His Phe Ser Leu Ser His Thr His Met Asp Ile Val Glu Ala
                        340                 345                 350

Asp Val His Lys Asn Trp Val Arg Tyr Ala Val Asp His Thr Val Asp
                    355                 360                 365

Ile Ser Pro Ser Asn Pro Leu Val Cys Trp Val Met Gly Tyr Leu Asn
        370                 375                 380

Met Gln Thr Ile His His Leu Trp Pro Ala Met Pro Gln Tyr His Gln
        385                 390                 395                 400

Val Glu Val Ser Arg Arg Phe Ala Ile Phe Ala Lys Lys His Gly Leu
                            405                 410                 415

Asn Tyr Arg Val Val Ser Tyr Phe Glu Ala Trp Arg Leu Met Leu Gln
                        420                 425                 430

Asn Leu Ala Asp Val Gly Ser His Tyr His Glu Asn Gly Val Lys Arg
                    435                 440                 445

Ala Pro Lys Lys Ala Lys Ala Gln
        450                 455

<210> SEQ ID NO 10
<211> LENGTH: 453
<212> TYPE: PRT
<213> ORGANISM: Saprolegnia diclina

<400> SEQUENCE: 10

Met Val Gln Gly Gln Lys Ala Glu Lys Ile Ser Trp Ala Thr Ile Arg
        1               5                   10                  15

Glu His Asn Arg Gln Asp Asn Ala Trp Ile Val Ile His His Lys Val
                        20                  25                  30

Tyr Asp Ile Ser Ala Phe Glu Asp His Pro Gly Gly Val Val Met Phe
```

```
              35                  40                  45
Thr Gln Ala Gly Glu Asp Ala Thr Asp Ala Phe Ala Val Phe His Pro
 50                  55                  60

Ser Ser Ala Leu Lys Leu Leu Glu Gln Tyr Tyr Val Gly Asp Val Asp
 65                  70                  75                  80

Gln Ser Thr Ala Ala Val Asp Thr Ser Ile Ser Asp Glu Val Lys Lys
                     85                  90                  95

Ser Gln Ser Asp Phe Ile Ala Ser Tyr Arg Lys Leu Arg Leu Glu Val
                100                 105                 110

Lys Arg Leu Gly Leu Tyr Asp Ser Ser Lys Leu Tyr Tyr Leu Tyr Lys
                115                 120                 125

Cys Ala Ser Thr Leu Ser Ile Ala Leu Val Ser Ala Ala Ile Cys Leu
130                 135                 140

His Phe Asp Ser Thr Ala Met Tyr Met Val Ala Ala Val Ile Leu Gly
145                 150                 155                 160

Leu Phe Tyr Gln Gln Cys Gly Trp Leu Ala His Asp Phe Leu His His
                165                 170                 175

Gln Val Phe Glu Asn His Leu Phe Gly Asp Leu Val Gly Val Met Val
                180                 185                 190

Gly Asn Leu Trp Gln Gly Phe Ser Val Gln Trp Trp Lys Asn Lys His
                195                 200                 205

Asn Thr His His Ala Ile Pro Asn Leu His Ala Thr Pro Glu Ile Ala
210                 215                 220

Phe His Gly Asp Pro Asp Ile Asp Thr Met Pro Ile Leu Ala Trp Ser
225                 230                 235                 240

Leu Lys Met Ala Gln His Ala Val Asp Ser Pro Val Gly Leu Phe Phe
                245                 250                 255

Met Arg Tyr Gln Ala Tyr Leu Tyr Phe Pro Ile Leu Leu Phe Ala Arg
                260                 265                 270

Ile Ser Trp Val Ile Gln Ser Ala Met Tyr Ala Phe Tyr Asn Val Gly
                275                 280                 285

Pro Gly Gly Thr Phe Asp Lys Val Gln Tyr Pro Leu Leu Glu Arg Ala
290                 295                 300

Gly Leu Leu Leu Tyr Tyr Gly Trp Asn Leu Gly Leu Val Tyr Ala Ala
305                 310                 315                 320

Asn Met Ser Leu Leu Gln Ala Ala Ala Phe Leu Phe Val Ser Gln Ala
                325                 330                 335

Ser Cys Gly Leu Phe Leu Ala Met Val Phe Ser Val Gly His Asn Gly
                340                 345                 350

Met Glu Val Phe Asp Lys Asp Ser Lys Pro Asp Phe Trp Lys Leu Gln
                355                 360                 365

Val Leu Ser Thr Arg Asn Val Thr Ser Ser Leu Trp Ile Asp Trp Phe
370                 375                 380

Met Gly Gly Leu Asn Tyr Gln Ile Asp His His Leu Phe Pro Met Val
385                 390                 395                 400

Pro Arg His Asn Leu Pro Ala Leu Asn Val Leu Val Lys Ser Leu Cys
                405                 410                 415

Lys Gln Tyr Asp Ile Pro Tyr His Glu Thr Gly Phe Ile Ala Gly Met
                420                 425                 430

Ala Glu Val Val Val His Leu Glu Arg Ile Ser Ile Glu Phe Phe Lys
                435                 440                 445

Glu Phe Pro Ala Met
                450
```

<210> SEQ ID NO 11
<211> LENGTH: 467
<212> TYPE: PRT
<213> ORGANISM: Mucor circinelloides

<400> SEQUENCE: 11

```
Met Ser Ser Asp Val Gly Ala Thr Val Pro His Phe Tyr Thr Arg Ala
1               5                   10                  15

Glu Leu Ala Asp Ile His Gln Asp Val Leu Asp Lys Lys Pro Glu Ala
            20                  25                  30

Arg Lys Leu Ile Val Val Glu Asn Lys Val Tyr Asp Ile Thr Asp Phe
        35                  40                  45

Val Phe Asp His Pro Gly Gly Glu Arg Val Leu Leu Thr Gln Glu Gly
    50                  55                  60

Arg Asp Ala Thr Asp Val Phe His Glu Met His Pro Pro Ser Ala Tyr
65                  70                  75                  80

Glu Leu Leu Ala Asn Cys Tyr Val Gly Asp Cys Glu Pro Lys Leu Pro
                85                  90                  95

Ile Asp Ser Thr Asp Lys Lys Ala Leu Asn Ser Ala Ala Phe Ala Gln
            100                 105                 110

Glu Ile Arg Asp Leu Arg Asp Lys Leu Glu Lys Gln Gly Tyr Phe Asp
        115                 120                 125

Ala Ser Thr Gly Phe Tyr Ile Tyr Lys Val Ser Thr Thr Leu Leu Val
    130                 135                 140

Cys Ile Val Gly Leu Ala Ile Leu Lys Ala Trp Gly Arg Glu Ser Thr
145                 150                 155                 160

Leu Ala Val Phe Ile Ala Ala Ser Leu Val Gly Leu Phe Trp Gln Gln
                165                 170                 175

Cys Gly Trp Leu Ala His Asp Tyr Ala His Tyr Gln Val Ile Lys Asp
            180                 185                 190

Pro Asn Val Asn Asn Leu Phe Leu Val Thr Phe Gly Asn Leu Val Gln
        195                 200                 205

Gly Phe Ser Leu Ser Trp Trp Lys Asn Lys His Asn Thr His His Ala
    210                 215                 220

Ser Thr Asn Val Ser Gly Glu Asp Pro Asp Ile Asp Thr Ala Pro Ile
225                 230                 235                 240

Leu Leu Trp Asp Glu Phe Ala Val Ala Asn Phe Tyr Gly Ser Leu Lys
                245                 250                 255

Asp Asn Ala Ser Gly Phe Asp Arg Phe Ile Ala Glu His Ile Leu Pro
            260                 265                 270

Tyr Gln Thr Arg Tyr Tyr Phe Phe Ile Leu Gly Phe Ala Arg Thr Ser
        275                 280                 285

Trp Ala Ile Gln Ser Ile Ile Tyr Ser Phe Lys Asn Glu Thr Leu Asn
    290                 295                 300

Lys Ser Lys Leu Leu Ser Trp Cys Glu Arg Ile Phe Leu Ile Val His
305                 310                 315                 320

Trp Val Phe Phe Thr Tyr Cys Thr Ile Ala Trp Ile Ser Ser Ile Arg
                325                 330                 335

Asn Ile Ala Met Phe Phe Val Val Ser Gln Ile Thr Thr Gly Tyr Leu
            340                 345                 350

Leu Ala Ile Val Phe Ala Met Asn His Asn Gly Met Pro Val Tyr Ser
        355                 360                 365

Pro Glu Glu Ala Asn His Thr Glu Phe Tyr Glu Leu Gln Cys Ile Thr
    370                 375                 380
```

```
Gly Arg Asp Val Asn Cys Thr Val Phe Gly Asp Trp Leu Met Gly Gly
385                 390                 395                 400

Leu Asn Tyr Gln Ile Glu His His Leu Phe Pro Glu Met Pro Arg His
            405                 410                 415

His Leu Ser Lys Val Lys Ser Met Val Lys Pro Ile Ala Gln Lys Tyr
        420                 425                 430

Asn Ile Pro Tyr His Asp Thr Thr Val Ile Gly Gly Thr Ile Glu Val
            435                 440                 445

Leu Gln Thr Leu Asp Phe Val Gln Lys Ile Ser Gln Lys Phe Ser Lys
    450                 455                 460

Lys Met Leu
465

<210> SEQ ID NO 12
<211> LENGTH: 383
<212> TYPE: PRT
<213> ORGANISM: Borago officinalis

<400> SEQUENCE: 12

Met Gly Gly Gly Arg Met Pro Val Pro Thr Lys Gly Lys Lys Ser
1               5                   10                  15

Lys Ser Asp Val Phe Gln Arg Val Pro Ser Glu Lys Pro Pro Phe Thr
            20                  25                  30

Val Gly Asp Leu Lys Lys Val Ile Pro Pro His Cys Phe Gln Arg Ser
        35                  40                  45

Val Leu His Ser Phe Ser Tyr Val Val Tyr Asp Leu Val Ile Ala Ala
    50                  55                  60

Leu Phe Phe Tyr Thr Ala Ser Arg Tyr Ile His Leu Gln Pro His Pro
65                  70                  75                  80

Leu Ser Tyr Val Ala Trp Pro Leu Tyr Trp Phe Cys Gln Gly Ser Val
            85                  90                  95

Leu Thr Gly Val Trp Val Ile Ala His Glu Cys Gly His His Ala Phe
        100                 105                 110

Ser Asp Tyr Gln Trp Leu Asp Asp Thr Val Gly Leu Leu Leu His Ser
    115                 120                 125

Ala Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Arg Ser Gly Ile Ser Trp Ser Ser Glu Tyr Leu Asn Asn Pro Pro
            165                 170                 175

Gly Arg Val Leu Val Leu Leu Val Gln Leu Thr Leu Gly Trp Pro Leu
        180                 185                 190

Tyr Leu Met Phe Asn Val Ser Gly Arg Pro Tyr Asp Arg Phe Ala Cys
    195                 200                 205

His Phe Asp Pro Lys Ser Pro Ile Tyr Asn Asp Arg Glu Arg Leu Gln
            210                 215                 220

Ile Tyr Ile Ser Asp Ala Gly Ile Val Ala Val Met Tyr Gly Leu Tyr
225                 230                 235                 240

Arg Leu Val Ala Ala Lys Gly Val Ala Trp Val Val Cys Tyr Tyr Gly
            245                 250                 255

Val Pro Leu Leu Val Val Asn Gly Phe Leu Val Leu Ile Thr Tyr Leu
        260                 265                 270

Gln His Thr Gln Pro Ser Leu Pro His Tyr Asp Ser Ser Glu Trp Asp
    275                 280                 285
```

```
Trp Leu Lys Gly Ala Leu Ala Thr Val Asp Arg Asp Tyr Gly Phe Leu
        290                 295                 300

Asn Lys Val Leu His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Asp Tyr Tyr Gln Cys Asp Arg Thr Pro Val Phe
                340                 345                 350

Lys Ala Met Tyr Arg Glu Val Lys Glu Cys Ile Tyr Val Glu Ala Asp
                355                 360                 365

Glu Gly Asp Asn Lys Lys Gly Val Phe Trp Tyr Lys Asn Lys Leu
        370                 375                 380

<210> SEQ ID NO 13
<211> LENGTH: 382
<212> TYPE: PRT
<213> ORGANISM: Helianthus annuus

<400> SEQUENCE: 13

Met Gly Ala Gly Gly Arg Met Ser Ser Pro Asn Gly Lys Glu Lys Asp
1               5                   10                  15

Gly Pro Lys Pro Leu Glu Arg Ala Leu His Glu Lys Pro Pro Phe Thr
                20                  25                  30

Val Gly Asp Ile Lys Lys Val Ile Pro Pro His Cys Phe Lys Arg Ser
                35                  40                  45

Val Ile Arg Ser Phe Ser Tyr Val Val Tyr Asp Leu Thr Ile Ala Ser
        50                  55                  60

Ile Phe Tyr Tyr Leu Ala Asn Asn Tyr Ile Pro Leu Leu Pro Asn Ser
65                  70                  75                  80

Leu Ala Tyr Val Ala Trp Pro Val Tyr Trp Ile Phe Gln Gly Cys Val
                85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Leu His Ser
            115                 120                 125

Ala Leu Leu Val Pro Tyr Phe Ser Trp Lys Tyr Ser His Arg Arg His
        130                 135                 140

His Ser Asn Thr Gly Ser Ile Glu His Asp Glu Val Phe Val Pro Lys
145                 150                 155                 160

Leu Lys Ser Ser Val Arg Ser Thr Ala Lys Tyr Leu Asn Asn Pro Pro
                165                 170                 175

Gly Arg Ile Leu Thr Leu Leu Val Thr Leu Thr Met Gly Trp Pro Leu
            180                 185                 190

Tyr Leu Met Phe Asn Val Ser Gly Arg Tyr Tyr Asp Arg Phe Ala Cys
        195                 200                 205

His Phe Asp Pro Asn Ser Pro Ile Tyr Ser Asn Arg Glu Arg Ala Gln
    210                 215                 220

Ile Phe Ile Ser Asp Ala Gly Ile Leu Thr Val Phe Tyr Ile Leu Phe
225                 230                 235                 240

Arg Leu Ala Ser Thr Lys Gly Leu Val Trp Val Leu Thr Met Tyr Gly
                245                 250                 255

Gly Pro Leu Leu Val Val Asn Gly Phe Leu Val Leu Ile Thr Phe Leu
            260                 265                 270

Gln His Thr His Pro Ser Leu Pro His Tyr Asp Ser Thr Glu Trp Asp
        275                 280                 285
```

```
Trp Leu Arg Gly Ala Leu Ala Thr Val Asp Arg Asp Tyr Gly Ile Leu
    290                 295                 300

Asn Lys Val Phe His Asn Ile Thr Asp Thr His Val Thr His His Leu
305                 310                 315                 320

Phe Ser Thr Met Pro His Tyr His Ala Met Glu Ala Thr Lys Ala Ile
                325                 330                 335

Lys Pro Ile Leu Gly Asp Tyr Tyr Gln Phe Asp Gly Thr Ser Ile Phe
            340                 345                 350

Lys Ala Met Tyr Arg Glu Thr Lys Glu Cys Ile Tyr Val Asp Lys Asp
            355                 360                 365

Glu Asp Val Lys Asp Gly Val Tyr Trp Tyr Arg Asn Lys Ile
370                 375                 380

<210> SEQ ID NO 14
<211> LENGTH: 384
<212> TYPE: PRT
<213> ORGANISM: Brassica napus

<400> SEQUENCE: 14

Met Gly Ala Gly Gly Arg Met Gln Val Ser Pro Pro Ser Ser Pro
1               5                   10                  15

Gly Thr Asn Thr Leu Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Pro Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
            180                 185                 190

Tyr Leu Ala Phe Asn Val Ser Gly Arg Pro Tyr Ser Asp Gly Phe Ala
        195                 200                 205

Cys His Phe His Pro Asn Ala Pro Ile Tyr Asn Asp Arg Glu Arg Leu
    210                 215                 220

Gln Ile Tyr Ile Ser Asp Ala Gly Val Leu Ser Val Cys Tyr Gly Leu
225                 230                 235                 240

Tyr Arg Tyr Ala Gly Ser Arg Gly Val Ala Ser Met Val Cys Val Tyr
                245                 250                 255

Gly Val Pro Leu Met Ile Val Asn Cys Phe Leu Val Leu Ile Thr Tyr
            260                 265                 270

Leu Gln His Thr His Pro Ser Leu Pro His Tyr Asp Ser Ser Glu Trp
        275                 280                 285
```

```
Asp Trp Leu Arg Gly Ala Leu Ala Thr Val Asp Arg Asp Tyr Gly Ile
        290                 295                 300

Leu Ser Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
                    325                 330                 335

Ile Lys Pro Ile Leu Gly Glu Tyr Tyr Gln Phe Asp Gly Thr Pro Val
                340                 345                 350

Val Lys Ala Met Trp Arg Glu Ala Lys Glu Cys Ile Tyr Val Glu Pro
                355                 360                 365

Asp Arg Gln Gly Glu Lys Lys Gly Val Phe Trp Tyr Asn Asn Lys Leu
        370                 375                 380
```

<210> SEQ ID NO 15
<211> LENGTH: 388
<212> TYPE: PRT
<213> ORGANISM: Oriza sativa

<400> SEQUENCE: 15

```
Met Gly Ala Gly Gly Arg Met Thr Glu Lys Glu Arg Glu Gln Gln
1               5                   10                  15

Lys Leu Leu Gly Arg Ala Gly Asn Gly Ala Ala Val Gln Arg Ser Pro
                20                  25                  30

Thr Asp Lys Pro Pro Phe Thr Leu Gly Gln Ile Lys Lys Ala Ile Pro
                35                  40                  45

Pro His Cys Phe Gln Arg Ser Val Ile Lys Ser Phe Ser Tyr Val Val
        50                  55                  60

His Asp Leu Val Ile Val Ala Ala Leu Leu Tyr Phe Ala Leu Val Met
65                  70                  75                  80

Ile Pro Val Leu Pro Ser Gly Met Glu Phe Ala Ala Trp Pro Leu Tyr
                85                  90                  95

Trp Ile Ala Gln Gly Cys Val Leu Thr Gly Val Trp Val Ile Ala His
                100                 105                 110

Glu Cys Gly His His Ala Phe Ser Asp Tyr Ser Val Leu Asp Asp Ile
        115                 120                 125

Val Gly Leu Val Leu His Ser Ser Leu Leu Val Pro Tyr Phe Ser Trp
130                 135                 140

Lys Tyr Ser His Arg Arg His His Ser Asn Thr Gly Ser Leu Glu Arg
145                 150                 155                 160

Asp Glu Val Phe Val Pro Lys Gln Lys Ser Ala Met Ala Trp Tyr Thr
                165                 170                 175

Pro Tyr Val Tyr His Asn Pro Ile Gly Arg Leu Val His Ile Phe Val
                180                 185                 190

Gln Leu Thr Leu Gly Trp Pro Leu Tyr Leu Ala Phe Asn Val Ser Gly
        195                 200                 205

Arg Pro Tyr Pro Arg Phe Ala Cys His Phe Asp Pro Tyr Gly Pro Ile
210                 215                 220

Tyr Asn Asp Arg Glu Arg Val Gln Ile Phe Ile Ser Asp Val Gly Val
225                 230                 235                 240

Val Ser Ala Gly Leu Ala Leu Phe Lys Leu Ser Ser Ala Phe Gly Phe
                245                 250                 255

Trp Trp Val Val Arg Val Tyr Gly Val Pro Leu Leu Ile Val Asn Ala
                260                 265                 270

Trp Leu Val Leu Ile Thr Tyr Leu Gln His Thr His Pro Ala Leu Pro
        275                 280                 285
```

His Tyr Asp Ser Ser Glu Trp Asp Trp Leu Arg Gly Ala Leu Ala Thr
290                 295                 300

Val Asp Arg Asp Tyr Gly Ile Leu Asn Lys Val Phe His Asn Ile Thr
305                 310                 315                 320

Asp Thr His Val Ala His His Leu Phe Ser Thr Met Pro His Tyr His
                325                 330                 335

Ala Met Glu Ala Thr Lys Ala Ile Arg Pro Ile Leu Gly Glu Tyr Tyr
            340                 345                 350

Gln Phe Asp Pro Thr Pro Val Ala Lys Ala Thr Trp Arg Glu Ala Lys
        355                 360                 365

Glu Cys Ile Tyr Val Glu Pro Glu Asp Asn Lys Gly Val Phe Trp Tyr
370                 375                 380

Asn Asn Lys Phe
385

<210> SEQ ID NO 16
<211> LENGTH: 399
<212> TYPE: PRT
<213> ORGANISM: Mortierella alpina

<400> SEQUENCE: 16

Met Ala Pro Pro Asn Thr Ile Asp Ala Gly Leu Thr Gln Arg His Ile
1               5                   10                  15

Ser Thr Ser Ala Pro Asn Ser Ala Lys Pro Ala Phe Glu Arg Asn Tyr
            20                  25                  30

Gln Leu Pro Glu Phe Thr Ile Lys Glu Ile Arg Glu Cys Ile Pro Ala
        35                  40                  45

His Cys Phe Glu Arg Ser Gly Leu Arg Gly Leu Cys His Val Ala Ile
    50                  55                  60

Asp Leu Thr Trp Ala Ser Leu Leu Phe Leu Ala Ala Thr Gln Ile Asp
65                  70                  75                  80

Lys Phe Glu Asn Pro Leu Ile Arg Tyr Leu Ala Trp Pro Val Tyr Trp
                85                  90                  95

Ile Met Gln Gly Ile Val Cys Thr Gly Val Trp Val Leu Ala His Glu
            100                 105                 110

Cys Gly His Gln Ser Phe Ser Thr Ser Lys Thr Leu Asn Asn Thr Val
        115                 120                 125

Gly Trp Ile Leu His Ser Met Leu Leu Val Pro Tyr His Ser Trp Arg
    130                 135                 140

Ile Ser His Ser Lys His His Lys Ala Thr Gly His Met Thr Lys Asp
145                 150                 155                 160

Gln Val Phe Val Pro Lys Thr Arg Ser Gln Val Gly Leu Pro Pro Lys
                165                 170                 175

Glu Asn Ala Ala Ala Ala Val Gln Glu Glu Asp Met Ser Val His Leu
            180                 185                 190

Asp Glu Glu Ala Pro Ile Val Thr Leu Phe Trp Met Val Ile Gln Phe
        195                 200                 205

Leu Phe Gly Trp Pro Ala Tyr Leu Ile Met Asn Ala Ser Gly Gln Asp
210                 215                 220

Tyr Gly Arg Trp Thr Ser His Phe His Thr Tyr Ser Pro Ile Phe Glu
225                 230                 235                 240

Pro Arg Asn Phe Phe Asp Ile Ile Ile Ser Asp Leu Gly Val Leu Ala
                245                 250                 255

Ala Leu Gly Ala Leu Ile Tyr Ala Ser Met Gln Leu Ser Leu Leu Thr
            260                 265                 270

```
Val Thr Lys Tyr Tyr Ile Val Pro Tyr Leu Phe Val Asn Phe Trp Leu
        275                 280                 285

Val Leu Ile Thr Phe Leu Gln His Thr Asp Pro Lys Leu Pro His Tyr
        290                 295                 300

Arg Glu Gly Ala Trp Asn Phe Gln Arg Gly Ala Leu Cys Thr Val Asp
305                 310                 315                 320

Arg Ser Phe Gly Lys Phe Leu Asp His Met Phe His Gly Ile Val His
                325                 330                 335

Thr His Val Ala His His Leu Phe Ser Gln Met Pro Phe Tyr His Ala
                340                 345                 350

Glu Glu Ala Thr Tyr His Leu Lys Lys Leu Leu Gly Tyr Tyr Val
                355                 360                 365

Tyr Asp Pro Ser Pro Ile Val Val Ala Val Trp Arg Ser Phe Arg Glu
370                 375                 380

Cys Arg Phe Val Glu Asp Gln Gly Asp Val Val Phe Phe Lys Lys
385                 390                 395

<210> SEQ ID NO 17
<211> LENGTH: 424
<212> TYPE: PRT
<213> ORGANISM: Aspergillus furnigatus

<400> SEQUENCE: 17

Met Ala Ser Asp Ala Glu Lys Thr Ser Ser Lys Met Ile Asp Thr Tyr
1               5                   10                  15

Gly Asn Glu Phe Lys Ile Pro Asp Tyr Thr Ile Lys Gln Ile Arg Asp
                20                  25                  30

Ala Ile Pro Ala His Cys Tyr Gln Arg Ser Ala Ala Thr Ser Leu Tyr
            35                  40                  45

Tyr Val Phe Arg Asp Met Ala Ile Leu Ala Ser Val Phe Tyr Val Phe
        50                  55                  60

His Asn Tyr Val Thr Pro Glu Thr Val Pro Ser Met Pro Val Arg Val
65                  70                  75                  80

Val Leu Trp Thr Ile Tyr Thr Val Val Gln Gly Leu Val Gly Thr Gly
                85                  90                  95

Val Trp Val Leu Ala His Glu Cys Gly His Gln Ala Phe Ser Thr Ser
                100                 105                 110

Lys Val Leu Asn Asp Thr Val Gly Trp Ile Cys His Ser Leu Leu Leu
            115                 120                 125

Val Pro Tyr Phe Ser Trp Lys Ile Ser His Gly Lys His His Lys Ala
        130                 135                 140

Thr Gly Asn Ile Ala Arg Asp Met Val Phe Val Pro Lys Thr Arg Glu
145                 150                 155                 160

Glu Tyr Ala Thr Arg Ile Gly Arg Ala Ala His Glu Leu Ser Glu Leu
                165                 170                 175

Met Glu Glu Thr Pro Ile Leu Thr Ala Thr Asn Leu Val Leu Gln Gln
            180                 185                 190

Leu Phe Gly Trp Pro Met Tyr Leu Leu Thr Asn Val Thr Gly His Asn
        195                 200                 205

Asn His Glu Arg Gln Pro Glu Gly Arg Gly Lys Gly Lys Arg Asn Gly
    210                 215                 220

Tyr Phe Gly Gly Val Asn His Phe Asn Pro Ser Ser Pro Leu Tyr Glu
225                 230                 235                 240

Ala Lys Asp Ala Lys Leu Ile Val Leu Ser Asp Leu Gly Leu Phe Leu
                245                 250                 255
```

```
Val Gly Ser Leu Leu Tyr Tyr Ile Gly Ser Thr Tyr Gly Trp Leu Asn
            260                 265                 270

Leu Leu Val Trp Tyr Gly Ile Pro Tyr Leu Trp Val Asn His Trp Leu
        275                 280                 285

Val Ala Ile Thr Phe Leu Gln His Thr Asp Pro Thr Leu Pro His Tyr
    290                 295                 300

Gln Pro Glu Ala Trp Asp Phe Thr Arg Gly Ala Ala Thr Ile Asp
305                 310                 315                 320

Arg Asp Phe Gly Phe Val Gly Arg His Ile Phe His Gly Ile Ile Glu
                325                 330                 335

Thr His Val Leu His His Tyr Val Ser Thr Ile Pro Phe Tyr His Ala
                340                 345                 350

Asp Glu Ala Ser Glu Ala Ile Gln Lys Val Met Gly Pro His Tyr Arg
                355                 360                 365

Ser Glu Ala His Thr Gly Trp Thr Gly Phe Leu Lys Ala Leu Trp Thr
            370                 375                 380

Ser Ala Arg Thr Cys Gln Trp Val Glu Pro Thr Glu Gly Ala Lys Gly
385                 390                 395                 400

Glu Ser Gln Tyr Val Leu Phe Tyr Arg Asn Ile Asn Gly Ile Gly Val
                405                 410                 415

Pro Pro Ala Lys Ile Pro Ala Lys
            420

<210> SEQ ID NO 18
<211> LENGTH: 436
<212> TYPE: PRT
<213> ORGANISM: Candida albicans

<400> SEQUENCE: 18

Met Ala Ala Ala Thr Thr Ser Phe Ser Ser Gly Phe Asn Asn Asn Asn
1               5                   10                  15

Asn Ala Asp Gln Ser Thr Asp Ser Ser Ala Thr Ile Ser Lys Ser Gly
            20                  25                  30

Asn Val Ala Ser Phe Lys Thr Thr Ser Thr Thr Ser Thr Tyr Gln Thr
        35                  40                  45

Asn Leu Thr Ala Ile Asp Thr Tyr Gly Asn Glu Phe Lys Val Pro Asp
    50                  55                  60

Tyr Thr Ile Lys Asp Ile Leu Ser Ala Ile Pro Thr His Cys Tyr Glu
65                  70                  75                  80

Arg Arg Leu Leu Gln Ser Leu Ser Tyr Val Phe Arg Asp Ile Phe Cys
                85                  90                  95

Met Val Val Leu Gly Phe Ile Ala Asn Asn Tyr Ile His Leu Ile Pro
            100                 105                 110

Asn Gln Phe Ile Arg Phe Ala Ala Trp Thr Gly Tyr Val Trp Cys Gln
        115                 120                 125

Gly Leu Phe Gly Thr Gly Ile Trp Val Leu Ala His Glu Cys Gly His
    130                 135                 140

Gln Ala Phe Ser Asp Tyr Gly Ser Val Asn Asp Phe Val Gly Trp Val
145                 150                 155                 160

Leu His Ser Tyr Leu Leu Val Pro Tyr Phe Ser Trp Lys Phe Ser His
                165                 170                 175

Gly Lys His His Lys Ala Thr Gly His Leu Thr Arg Asp Met Val Phe
            180                 185                 190

Val Pro Lys Thr Lys Glu Glu Phe Leu Gln Asn Arg Gly Val Lys Asp
        195                 200                 205
```

```
Leu Asp Asp Leu Leu Gly Asp Ser Pro Met Tyr Ser Leu Leu Thr Leu
    210                 215                 220

Ile Phe Gln Gln Thr Phe Gly Trp Ile Ser Tyr Leu Val Ala Asn Val
225                 230                 235                 240

Ser Gly Gln Lys Tyr Pro Gly Val Ser Phe Leu Lys Leu Asn His Phe
            245                 250                 255

Asn Pro Asn Ser Leu Ile Phe Asp Lys Lys Asp Tyr Trp Tyr Ile Leu
            260                 265                 270

Leu Ser Asp Leu Gly Ile Leu Leu Gln Phe Phe Asn Leu Tyr Val Trp
    275                 280                 285

Tyr Gln Ser Phe Gly Gly Phe Asn Leu Leu Val Asn Tyr Val Leu Pro
290                 295                 300

Tyr Phe Leu Val Asn His Trp Leu Val Phe Ile Thr Tyr Leu Gln His
305                 310                 315                 320

Ser Asp Pro Gln Met Pro His Tyr Glu Ala Ser Gln Trp Thr Phe Ala
            325                 330                 335

Arg Gly Ala Ala Ala Thr Ile Asp Arg Glu Phe Gly Phe Val Gly Lys
            340                 345                 350

His Ile Phe His Asp Ile Ile Glu Thr His Val Leu His His Tyr Val
            355                 360                 365

Ser Arg Ile Pro Phe Tyr Asn Ala Arg Glu Ala Ser Glu Ala Ile Lys
370                 375                 380

Lys Val Met Gly Ile His Tyr Gln His Ser Asp Glu Asn Met Trp Val
385                 390                 395                 400

Ser Leu Trp Lys Ser Ala Arg Trp Cys Gln Phe Val Asp Gly Asn Asn
            405                 410                 415

Gly Val Leu Met Tyr Arg Asn Thr Asn Gly Phe Gly Val Asp Pro Lys
            420                 425                 430

Lys Gln Thr His
        435

<210> SEQ ID NO 19
<211> LENGTH: 433
<212> TYPE: PRT
<213> ORGANISM: Candida albicans

<400> SEQUENCE: 19

Met Ser Val Val Glu Ala Ser Ser Ser Val Val Glu Asp Ser Thr
1               5                   10                  15

Ala Ser Asn Val Val Gln Arg Gly Asn Ile Ser Ser Phe Ala Ser Thr
            20                  25                  30

Thr Ala Ser Ser Asn Leu Thr Thr Ile Asp Thr Asn Gly Lys Val Phe
            35                  40                  45

Lys Val Pro Asp Tyr Ser Ile Lys Asp Ile Leu Gln Ala Ile Pro Lys
    50                  55                  60

His Cys Tyr Glu Arg Ser Leu Ile Arg Ser Leu Gly Tyr Val Val Arg
65                  70                  75                  80

Asp Ile Thr Met Met Val Ile Ile Gly Tyr Val Gly His Thr Phe Ile
                85                  90                  95

Pro Met Val Gln Ile Pro Glu Tyr Pro Ser Leu Ala Tyr Gly Leu Arg
            100                 105                 110

Gly Ala Leu Trp Met Val Gln Ser Tyr Cys Ile Gly Leu Phe Gly Phe
        115                 120                 125

Gly Leu Trp Ile Leu Ala His Glu Cys Gly His Gly Ala Phe Ser Asp
    130                 135                 140
```

```
Tyr Gln Asn Ile Asn Asp Phe Ile Gly Trp Val Leu His Ser Tyr Leu
145                 150                 155                 160

Ile Val Pro Tyr Phe Ser Trp Lys Phe Ser His Ala Lys His His Lys
                165                 170                 175

Ala Thr Gly His Leu Thr Lys Asp Met Val Phe Ile Pro Tyr Thr Lys
            180                 185                 190

Glu Glu Tyr Leu Glu Lys Asn Lys Val Glu Lys Val Ala Asp Leu Met
        195                 200                 205

Glu Glu Ser Pro Ile Tyr Ser Phe Leu Val Leu Val Phe Gln Gln Leu
        210                 215                 220

Gly Gly Leu Gln Leu Tyr Leu Ala Thr Asn Ala Thr Gly Gln Val Tyr
225                 230                 235                 240

Pro Gly Tyr Ser Lys Ile Ala Lys Ser His Tyr Thr Pro Thr Ser Pro
                245                 250                 255

Val Phe Asp Lys His Gln Tyr Trp Tyr Ile Val Leu Ser Asp Ile Gly
                260                 265                 270

Ile Ile Leu Ala Phe Thr Thr Val Tyr Gln Trp Tyr Lys Asn Phe Gly
            275                 280                 285

Leu Phe Asn Met Met Ile Asn Trp Phe Val Pro Trp Leu Trp Val Asn
    290                 295                 300

His Trp Leu Val Phe Val Thr Phe Leu Gln His Thr Asp Pro Thr Met
305                 310                 315                 320

Pro His Tyr Thr Ser Lys Glu Trp Thr Phe Ala Arg Gly Ala Ala Ala
                325                 330                 335

Thr Ile Asp Arg Asn Phe Gly Phe Val Gly Gln His Ile Phe His Asp
            340                 345                 350

Ile Ile Glu Thr His Val Leu His His Tyr Val Ser Arg Ile Pro Phe
            355                 360                 365

Tyr Asn Ala Arg Glu Ala Thr Asp Ala Ile Arg Lys Val Met Gly Glu
    370                 375                 380

His Tyr Arg Tyr Glu Gly Glu Ser Met Trp Tyr Ser Leu Trp Lys Cys
385                 390                 395                 400

Met Arg Met Cys Gln Phe Val Asp Asp Asp Lys Glu Asp Ala Lys Gly
            405                 410                 415

Val Met Met Phe Arg Asn Val Asn Gly Trp Gly Pro Val Lys Pro Lys
            420                 425                 430

Asp
```

SAFFLOWER WITH ELEVATED GAMMA-LINOLENIC ACID

CROSS-REFERENCE TO RELATED APPLICATIONS

This application is a divisional of U.S. Nonprovisional application Ser. No. 11/438,951, filed May 22, 2006, now U.S. Pat. No. 7,893,321, issued Feb. 22, 2011, which claims the benefit of U.S. Provisional Application No. 60/684,134, filed May 23, 2005, and U.S. Provisional Application No. 60/735,984, filed Nov. 10, 2005, all of which are hereby incorporated by reference in their entirety.

BACKGROUND OF THE INVENTION

Gamma-linolenic acid (GLA) is an essential fatty acid in the omega-6 family that is found primarily in plant-based oils. GLA is synthesized from linoleic acid (LA) via the action of the enzyme delta-six desaturase (Δ6-desaturase). The beneficial effects of GLA derive from the fact that GLA serves as the precursor to a number of other essential fatty acids such as arachidonic acid, which is a precursor of prostaglandins and other physiologically important molecules.

Unsaturated fatty acids such as linoleic ($C_{18}\Delta$ 9, 12) and α-linolenic ($C_{18}\Delta$ 9, 12, 15) acids are essential dietary constituents that cannot be synthesized by vertebrates because while vertebrate cells can introduce double bonds at the Δ 9 position of fatty acids, they cannot introduce additional double bonds between the Δ 9 double bond and the methyl-terminus of the fatty acid chain. Because they are required to synthesize other products, linoleic and α-linolenic acids are essential fatty acids, which are usually obtained from plant sources. LA can be converted by mammals into GLA ($C_{18}\Delta$ 6, 9, 12) which can in turn be converted to arachidonic acid (20:4), a critically important fatty acid since it is an essential precursor of most prostaglandins.

The dietary provision of LA, by virtue of its enzymatic conversion to GLA and then into arachidonic acid, could satisfy the dietary need for GLA and arachidonic acid. However, the consumption of fats that are less highly unsaturated, such as LA, has been correlated with health risks such as hypercholesterolemia, atherosclerosis and other clinical disorders which increase susceptibility to coronary disease. In contrast, the consumption of fats that are more highly unsaturated has been associated with decreased blood cholesterol concentration and reduced risk of atherosclerosis. Consumption of the unsaturated fatty acid GLA has been shown to be particularly beneficial. Thus, the consumption of the more unsaturated GLA would be preferred over the consumption of LA. It would thus be desirable to generate additional sources rich in GLA for human consumption.

GLA acts as a precursor for the formation of eicosanoids including prostaglandins. Prostaglandins are vital hormone-like compounds that strengthen cell membranes and serve as cellular signaling molecules. Beneficial effects of GLA have been observed in humans and animals. GLA may help to regulate blood pressure, reduce inflammation and improve immune function. GLA supplementation may benefit a wide range of diseases and conditions including lupus, cancer, allergies, arthritis and ulcerative colitis. GLA may improve the efficacy of drugs used to treat cancer. GLA may help to reduce the symptoms of premenstrual syndrome and menopause; to improve skin health and to treat eczema, acne, rosacea, psoriasis and dandruff; to improve psychiatric and neurological disorders including Alzheimer's disease, Huntington's chorea, multiple sclerosis, attention deficit hyperactivity disorder, depression and Raynaud's phenomenon; to block diabetic neuropathy; to treat cirrhosis of the liver; to improve dry-eye conditions such as Sjögren's syndrome; and to treat cardiovascular disease, osteoporosis, hyperlipidemia and other symptoms associated with aging. Furthermore, GLA has been implicated as a stimulator for the body to burn brown fat. Brown fat is the inner body fat that surrounds vital organs and acts as a fat-burning factory, using calories for heat rather than storing them as white fat. The burning of brown fat is important for the maintenance of ideal body weight. Increased GLA consumption may thus help to stimulate the process of brown fat metabolism.

Existing GLA supplements are typically derived from plant sources that are naturally higher in GLA such as evening primrose oil, black currant oil and borage oil. However, GLA represents a relatively small fraction of the total fatty acids in these natural sources. Only approximately 7-10% (evening primrose), 14-19% (black currant oil) and 20-26% (borage oil) of the fatty acids from these sources are available as GLA. Despite GLA's broad health benefits, its use is currently limited by the high cost and low concentrations of existing GLA supplements. An average adult would need to consume 10 or more capsules of existing GLA supplements to receive its optimal health benefits. It would be useful to have a less expensive, readily available source of oil that was higher in GLA than the naturally occurring specialty oils currently used for GLA supplements. Such a source would allow consumers to receive the optimal health benefits of GLA, while spending less money on supplements and ingesting significantly less total oil and fewer calories.

Safflower is a commercially important agricultural crop. Safflower was first cultivated in the Near East thousands of years ago as a source of dye and other products that could be derived from the plant. Safflower in this century has been utilized as a source of edible oils. Safflower was first introduced to agriculture in the United States in the 1930s as a source of edible oils. Since then, varieties with improved oil content have been developed. Safflower oil primarily comprises the fatty acids palmitic, stearic, oleic and LA. Palmitic (C16:0) and stearic acids (C18:0) are saturated fatty acids; oleic (C18:1) and linoleic (C18:2) are unsaturated fatty acids. However, safflower plants naturally produce only negligible amounts of GLA.

As such, transgenic safflower plants with seeds containing higher levels of GLA than occur naturally would have great utility.

BRIEF SUMMARY OF THE PREFERRED EMBODIMENTS OF THE INVENTION

The present invention is directed to safflower plants that produce GLA. In one aspect, safflower plants that produce seeds including at least 1% by weight GLA, the seeds of such plants, and the oil of such plants are described. In preferred embodiments, the oil will have about 1-5, 5-10, 10-15, 15-20, 20-25, 25-30, 30-35, 35-40, 40-45, 45-50, 50-55 or 55-60% or greater by weight GLA.

In one aspect, safflower plants that contain genetic constructs including nucleic acid sequences that direct expression of one or more desaturase enzymes are described. In one aspect, the Δ6-desaturase is used alone to generate GLA in plants that produce primarily LA. In another aspect, the Δ6-desaturase is used in combination with delta-twelve desaturase (Δ12-desaturase) to produce GLA in plants that produce primarily oleic acid (OA) rather than LA. The constructs include coding sequences for these enzymes and generally include promoter and termination sequences. In one advantageous embodiment, the promoter is a seed specific promoter.

In one embodiment, a transgenic safflower plant containing a recombinant promoter functional in a safflower plant, operably linked to a recombinant DNA sequence encoding a Δ6-desaturase, in which the safflower plant produces seeds and the seeds contain at least 1% by weight GLA is described. The Δ6-desaturase encoding sequence can be derived from any plant or fungi. Such plant and fungi include but are not limited to *Mucor, Saprolegnia, Saprolegnia diclina, Mortierella, Mortierella alpina, Conidiobolus, Pythium, Phytophthora, Penicillium, Porphyridium, Coidosporium, Mucor circinelloides, Fusarium, Aspergillus, Candida, Rhodotorula, Entomophthora, Thraustochytrium, Saprolegnia, Borago, Primula*, sunflower, canola, rice, and moss. The promoter used can be a seed specific promoter such as an oleosin promoter or a linin promoter. Also provided by this embodiment is seed derived from these transgenic plants in which the GLA levels in the seed are at least 1% by weight of the total fatty acid content of the seed. Also provided by this embodiment is oil produced from the seeds of these transgenic plants. Such oil can contain 1-60% or greater by weight GLA.

In another embodiment, the invention provides a transgenic safflower plant containing a first recombinant DNA sequence encoding a Δ6-desaturase, and second recombinant DNA sequence encoding a Δ12-desaturase, where the sequences are operably linked to at least one promoter, in which the safflower plant produces seeds and the seeds contain at least 1% by weight GLA. In some embodiments, the first and second DNA sequences are linked to a single promoter. In other embodiments, the first and second DNA sequences are linked to different promoters. The Δ6- and Δ12-desaturase encoding sequences can be derived from any plant or fungi. Such plant and fungi include but are not limited to *Mucor, Saprolegnia, Saprolegnia diclina, Mortierella, Mortierella alpina, Conidiobolus, Pythium, Phytophthora, Penicillium, Porphyridium, Coidosporium, Mucor circinelloides, Fusarium, Aspergillus, Candida, Euphorbia, Dimorphoteca, Rhodotorula, Entomophthora, Thraustochytrium, Saprolegnia, Borago, Primula*, sunflower, canola, rice, and moss. The promoter used can be a seed specific promoter such as an oleosin promoter or a linin promoter. Also provided by this embodiment is seed derived from these transgenic plants in which the GLA levels in the seed are at least 1% by weight of the total fatty acid content of the seed. Also provided by this embodiment is oil produced from the seeds of these transgenic plants. Such oil can contain 1-60% or greater by weight GLA.

In yet another embodiment, a method for producing GLA in a safflower seed is provided. The method includes the steps of growing a safflower plant containing a recombinant promoter functional in a safflower plant, operably linked to a recombinant DNA sequence encoding a Δ6-desaturase, and growing the safflower plant under conditions in which the Δ6-desaturase sequence is expressed. The Δ6-desaturase encoding sequence can be derived from any plant or fungi. Such plant and fungi include but are not limited to *Mucor, Saprolegnia, Saprolegnia diclina, Mortierella, Mortierella alpina, Conidiobolus, Pythium, Phytophthora, Penicillium, Porphyridium, Coidosporium, Mucor circinelloides, Fusarium, Aspergillus, Candida, Rhodotorula, Entomophthora, Thraustochytrium, Saprolegnia, Borago, Primula*, sunflower, canola, rice, and moss. The promoter used can be a seed specific promoter such as an oleosin promoter or a linin promoter. Also provided by this embodiment is seed derived from these transgenic plants in which the GLA levels in the seed are at least 1% by weight of the total fatty acid content of the seed. Also provided by this embodiment is oil produced from the seeds of these transgenic plants. Such oil can contain 1-60% or greater by weight GLA.

In a further embodiment, a method for producing GLA in a safflower seed is provided. The method includes the steps of growing a safflower plant containing a first recombinant DNA sequence encoding a Δ6-desaturase, and a second recombinant DNA sequence encoding a Δ12-desaturase, where the sequences are operably linked to at least one promoter, and growing the safflower plant under conditions under which the Δ6-desaturase and Δ12-desaturase sequences are expressed. In this embodiment, the Δ6- and Δ12-desaturase encoding sequences can be derived from any plant or fungi. Such plant and fungi include but are not limited to *Mucor, Saprolegnia, Saprolegnia diclina, Mortierella, Mortierella alpina, Conidiobolus, Pythium, Phytophthora, Penicillium, Porphyridium, Coidosporium, Mucor circinelloides, Fusarium, Aspergillus, Candida, Euphorbia, Dimorphoteca, Rhodotorula, Entomophthora, Thraustochytrium, Saprolegnia, Borago, Primula*, sunflower, canola, rice, and moss. The promoter used can be a seed specific promoter such as an oleosin promoter or a linin promoter. Also provided by this embodiment is seed derived from these transgenic plants in which the GLA levels in the seed are at least 1% by weight of the total fatty acid content of the seed. Also provided by this embodiment is oil produced from the seeds of these transgenic plants. Such oil can contain 1-60% or greater by weight GLA.

In yet a further embodiment, safflower oil derived from a transgenic safflower plant in which the safflower oil has a content of GLA 1-5, 5-10, 10-15, 15-20, 20-25, 25-30, 30-35, 35-40, 40-45, 45-50, 50-55 or 55-60% or greater by weight is provided.

In yet a further embodiment, nutritional and personal care products including safflower oil with a content of GLA 1-5, 5-10, 10-15, 15-20, 20-25, 25-30, 30-35, 35-40, 40-45, 45-50, 50-55 or 55-60% or greater by weight is provided.

In an additional embodiment, a method of treating or preventing a psychiatric, neurological or other central or peripheral nervous system condition or disease by administering to a subject prone to or afflicted with such condition or diseases an effective amount of the oils described herein is provided.

In another additional embodiment, a method of treating or preventing an immunological condition or disease by administering to a subject prone to or afflicted with such condition or diseases an effective amount of the oils described herein is provided.

In a further additional embodiment, a method of treating or preventing an inflammatory condition or disease by administering to a subject prone to or afflicted with such condition or diseases an effective amount of the oils described herein is provided.

In a yet further additional embodiment, a method of treating or preventing cancer by administering to a subject prone to or afflicted with such diseases an effective amount of the oils described herein is provided.

In other embodiments, a method of treating or preventing a skin condition or disease by administering to a subject prone to or afflicted with such condition or diseases an effective amount of the oils described herein is provided.

In further other embodiments, a method of treating or preventing a cardiovascular condition or disease by administering to a subject prone to or afflicted with such diseases an effective amount of the oils described herein is provided.

In yet further other embodiments, a method of providing nutrition to an infant by administering to an infant an effective amount of the oils of this invention is provided.

BRIEF DESCRIPTION OF THE DRAWINGS

FIG. 2 shows the sequence alignments of various plant Δ6-desaturases (SEQ ID NO: 4-6) including a consensus sequence.

FIG. 3 shows the sequence alignments of various fungal Δ6-desaturases (SEQ ID NO: 7-11) including a consensus sequence.

FIG. 5 shows the sequence alignments of various plant Δ12-desaturases (SEQ ID NO: 12-15) including a consensus sequence.

FIG. 6 shows the sequence alignments of various fungal Δ12-desaturases (SEQ ID NO: 16-19) including a consensus sequence.

DETAILED DESCRIPTION OF THE INVENTION

In order to ensure a complete understanding of the invention, the following non-limiting definitions are provided.

Δ6-desaturase is an enzyme that introduces a double bond between carbons 6 and 7 from the carboxyl end of a fatty acid molecule.

Δ12-desaturase is an enzyme that introduces a double bond between carbons 12 and 13 from the carboxyl end of a fatty acid molecule.

As used herein, the abbreviation "GLA" is used to refer to gamma-linolenic acid.

Percentage by weight is meant to indicate the content of a particular fatty acid in a seed and/or oil from the seed based on weight. Thus, the percentage by weight of GLA or "by weight GLA" is calculated based on the weight of GLA divided by weight of total fatty acids multiplied by 100%. For example, "GLA levels at 5% by weight" or "5% by weight GLA" refers to seeds or oil from seeds that contains 5 grams of GLA and 100 grams of total fatty acid.

Introduction

Figure 1:
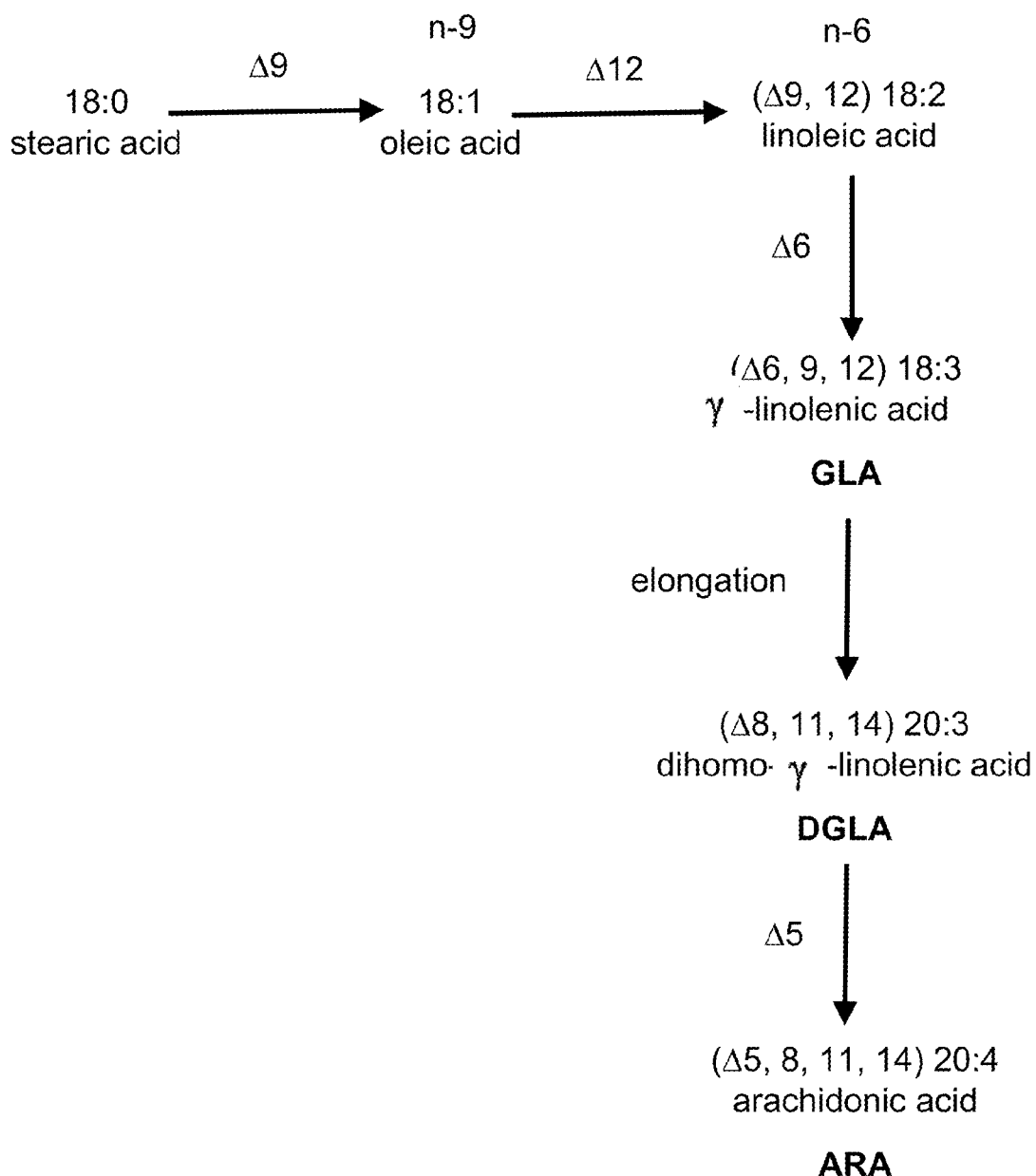
FIG. 1 shows the pathway for biosynthesis of GLA from the conversion of OA into LA, which is in turn converted into GLA through the consecutive action of the enzymes Δ6- and Δ12-desaturase as shown in the figure. GLA can be converted into arachidonic acid, which is a precursor for a number of prostaglandins, leukotrienes and other physiologically active molecules.

As shown in FIG. 1, GLA is produced in a biochemical pathway wherein OA is converted to LA. LA in turn is converted into GLA through the action of fatty acid desaturases, enzymes that introduce double bonds at specific locations in the fatty acid carbon chain. When these enzymes are transferred into cells that produce OA or LA, GLA is produced.

Safflower is a commercially important crop plant and is a valuable source of vegetable oil. Because safflower plants do not naturally produce GLA in any significant quantity, it would not be an obvious candidate for the production of this fatty acid. For example, because safflower plants do not normally produce GLA, one might expect that the expression of high levels of this non-endogenous fatty acid might be detrimental to the plant because the exogenously introduced GLA would interfere with the function of endogenous fatty acids. It has been surprisingly found that GLA can be expressed in safflower seeds and that this expression occurs at unexpectedly high levels, even when compared with other plants that express transgenes that are free of the concerns discussed above.

Characteristics of Desaturase Enzymes

The reaction catalyzed by desaturases is:

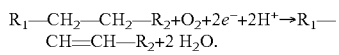

$$R_1-CH_2-CH_2-R_2+O_2+2e^-+2H^+ \rightarrow R_1-CH=CH-R_2+2\,H_2O.$$

Figure 4:
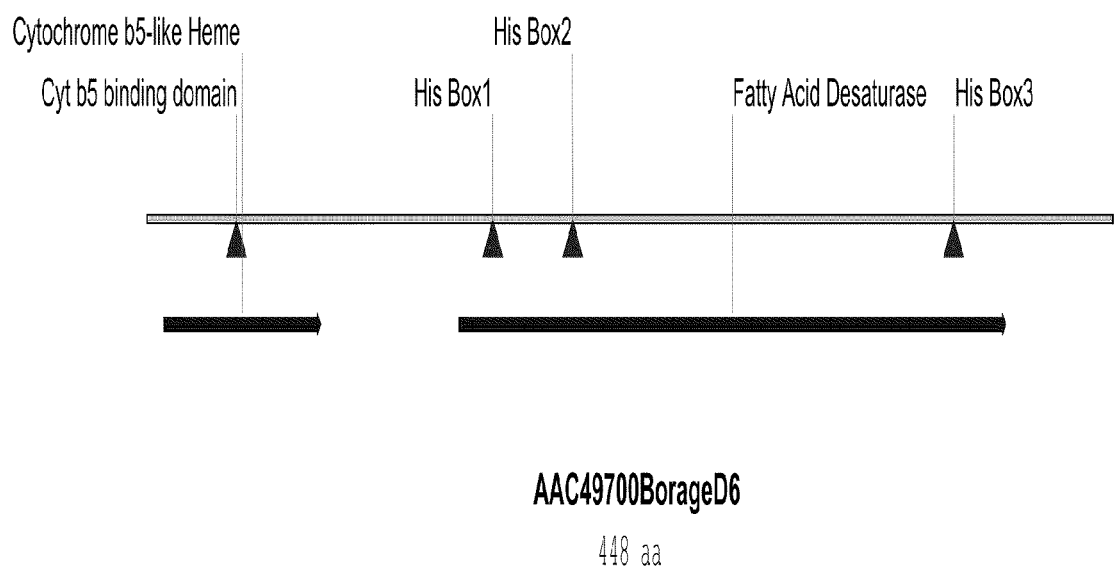
FIG. 4 shows a linear representation of conserved regions in Δ6-desaturases.
Figure 7:
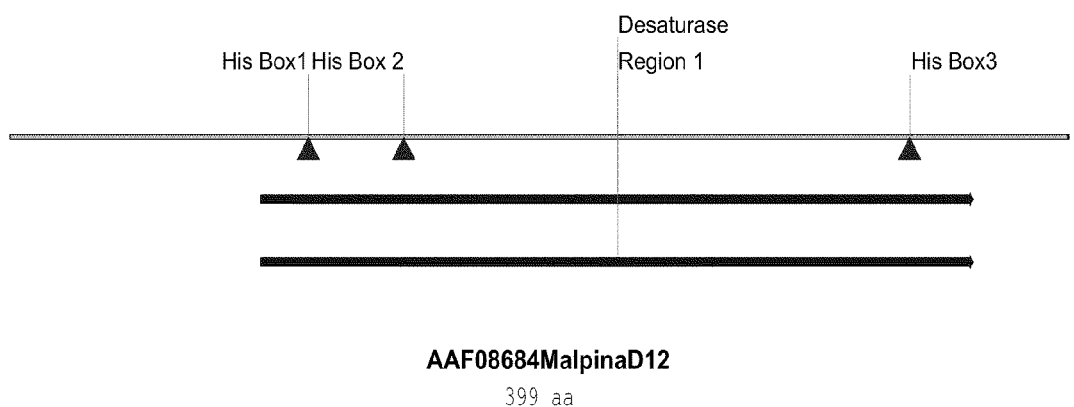
FIG. 7 shows a linear representation of conserved regions in Δ12-desaturases.

Many fatty acid desaturases are membrane bound metalloenzymes. Most are believed to contain two iron atoms at their active site. As shown in FIGS. 2, 3, 5 and 6, the Δ6- and Δ12-desaturases share a degree of sequence identity and similarity within each respective class of enzymes. As shown in FIGS. 4 and 7 among the regions of conservation within the desaturase family are three strongly conserved histidine-rich sequences (His-boxes) with the general motifs HXXXH, HXXHH and HXXHH or QXXHH. These boxes are required for enzyme activity and are separated by membrane-spanning domains that are required for their correct orientation in the active site. Many enzymes including the Δ5- and Δ6-desaturases contain a cytochrome b5-like N-terminal extension. This is often accompanied by a change in the sequence of the third His box to QXXHH. Electrons acquired from NADH cytochrome b5 reductase are transferred to cytochrome b5 or the cytochrome b5 domain of the desaturase and then to the active site of the desaturase. The mixed oxidation/reduction reaction proceeds through two iron atoms that are stabilized by interaction with the conserved histidine boxes. As discussed below, these structural features and, in particular, the conserved residues that make up the metal binding site, are conserved across species and are responsible for the enzymatic function of this class of enzymes.

Sources of Desaturase Enzymes

For the production of GLA, one or more desaturase enzymes will be required depending upon the host cell and the availability of substrates. For instance, in a plant that naturally has abundant amounts of LA, Δ6-desaturase is required to catalyze the conversion of LA into GLA. In plants that naturally have abundant amounts of OA, but not LA, a combination of Δ12- and Δ6-desaturase enzymes are required to generate GLA.

Considerations for choosing a specific desaturase polypeptide to use include correct localization and functioning of the polypeptide in the microsomal/endoplasmic reticulum compartment of the cell (these enzymes are membrane bound and must function in conjunction with the existing triglyceride biosynthetic machinery of the cell), whether the polypeptide is a rate limiting enzyme or a component thereof, whether the desaturase used is essential for synthesis of a desired polyunsaturated fatty acid and/or co-factors required by the polypeptide. The expressed polypeptide preferably has parameters compatible with the biochemical environment of its location in the host cell. For example, the polypeptide may have to compete for substrate with other enzymes in the host cell. Analyses of the $K_m$ and specific activity of the polypeptide in question therefore are considered in determining the suitability of a given polypeptide for modifying GLA production in a given host cell. The polypeptide used in a particular situation therefore is one which can function under the conditions present in the intended host cell but otherwise can be any polypeptide having desaturase activity that has the desired characteristic of being capable of modifying the relative production of GLA.

A number of Δ6- and Δ12-desaturases are known including those described in U.S. Pat. No. 6,635,451, WO02/081668, U.S. Pat. No. 6,635,451, U.S. Patent App. No. 2003/0167525, U.S. Pat. Nos. 6,459,018, 5,972,644, 6,432,684, 5,968,809, 5,972,664, 6,051,754, 6,075,183, 6,136,574, 5,552,306, 5,614,393, 5,663,068, 5,689,050, 5,789,220, 6,355,861 and 6,492,108, which are hereby incorporated by reference in their entirety and for the specific sequences disclosed therein. Among the sources of Δ6- and Δ12-desaturases useful for the practice of this invention are those from plants and fungi. For example, Δ6- and Δ12-desaturases from the genera *Mucor, Saprolegnia diclina, Mortierella, Mortierella alpina, Conidiobolus, Pythium, Phytophthora, Penicillium, Porphyridium, Coidosporium, Mucor circinelloides, Fusarium, Aspergillus, Candida, Euphorbia, Dimorphoteca, Rhodotorula, Entomophthora, Thraustochytrium, Saprolegnia, Borago* and *Primula* are useful in practice of this invention. Desaturases from sunflower, canola, rice, moss, and *C. elegans* can also be used in the practice of this invention. Such sequences will include histidine-rich boxes. These sequences can be used as well as sequences that have at least 80%, 85%, 90% or 95% identity based on various alignment methods well known in the art. Also useful are sequences that hybridize to the above sequences under high to moderate stringency. Hybridization and washing conditions that allow identification of additional sequences that correspond to desaturase sequences are also well known in the art, some of which are described below.

Among the methods for sequence alignment that are well known in the art are the programs and alignment algorithms described in: Smith and Waterman, J Mol Biol 147:195, 1981; Needleman and Wunsch, J Mol Biol 48:443, 1970; Pearson and Lipman, PNAS 85:2444, 1988; Higgins and Sharp, Gene 73:237, 1988; Higgins and Sharp, Comput Appl Biosci 5:151, 1989; Corpet, Nucl Acids Res 16:10881, 1988; Huang, Genomics 14:18, 1992; and Pearson, Methods Mol Biol 24:307, 1994. Altschul et al., (Nature Genetics 6:119, 1994) present a detailed consideration of sequence alignment methods and homology calculations.

The NCBI Basic Local Alignment Search Tool (BLAST) (Altschul et al., J Mol Biol 215:403, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

The AlignX program from Vector NTI was used to generate FIGS. 2, 3, 5 and 6. FIG. 2 shows an alignment of Δ6-desaturases from a number of different plant species. FIG. 3 shows an alignment of desaturases from a number of fungal species. FIGS. 5 and 6 show alignments of Δ12-desaturases from a number of plant and fungal species, respectively. These figures show the structural and functional relatedness of different Δ6- and Δ12-desaturases within their respective classes of enzymes. Any of the Δ6- or Δ12-desaturases shown in these figures can be used to practice the current invention as well as others that can be identified using the methods of this invention or otherwise available in the art as corresponding to Δ6- or Δ12-desaturases. Also encompassed by this invention are modifications of desaturases that still retain activity or possessed enhanced enzymatic activity that can be obtained through random or site directed mutagenesis.

It is well known to the skilled artisan that any of the sequences disclosed herein, as well as others known in the art, and previously unknown desaturases can be isolated using conventional cloning methods such as nucleic acid hybridization or PCR for use in the present invention.

Examples of hybridization conditions that can be used to isolate desaturase sequences include the following. Stringent conditions are sequence dependent and vary according to the experimental parameters used. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (Molecular Cloning—A Laboratory Manual $2^{nd}$ Edition, Cold Spring Harbor Laboratory Press, New York, 1989) and Tijssen (Hybridization with Nucleic Acid Probes, Elsevier Science Ltd., Amsterdam, 1993). Examples of factors that affect nucleic acid hybridization include: temperature, salt conditions, the presence of organic solvents in the hybridization mixtures, the lengths and base compositions of the sequences to be hybridized and the extent of base mismatching. An example of high stringency conditions for hybridizing a probe to a filter-bound DNA is 5×SSC, 2% sodium dodecyl sulfate (SDS), 100 μg/ml single stranded DNA at 55-65° C. for 20 minutes and washing in 0.1×SSC with 0.1% SDS at 60-65° C. for 20 minutes.

Alternatively, PCR primers can be designed to amplify particular desaturases of interest if the sequence of the desaturase cDNA is known. Further, PCR primers can be designed to conserved regions of the desaturases to isolate additional family members. Protocols for performing PCR reactions are well known in the art and are described in manuals such as PCR Protocols: A Guide to Methods and Applications by M. Innes et al., Academic Press, 1989.

Once sequences have been identified via sequence identity, hybridization, identification of conserved histidine boxes, or other suitable methods, desaturase activity can be tested using several different assays. By way of example is the use of yeast as described in U.S. Pat. No. 5,968,809 in Examples 5 to 7 and Knutzon, et al. J. Biol. Chem. 273 (45): 29360-29366 (1998), both which are hereby incorporated by reference. The yeast may be *Sacharomyces cerevisiae* or an oleaginous species. The sequence of interest is cloned into a yeast expression vector and transformed into yeast. The recombinant yeast strains are grown in media containing various substrates and the fatty acid content of the lipid fraction is analyzed to evaluate desaturase activity. Δ6-desaturase activity can be monitored by using linoleic acid as a substrate and detecting gamma-linolenic acid. Δ12-desaturase activity can be monitored by detecting conversion of endogenous oleic acid to linolenic acid.

Desaturase activity can also be tested using *Arabidopsis*. Sequences of interest are cloned into appropriate vectors, transformed into *Arabidopsis*, and activity detected by evaluating the phenotype of the transgenic plants. Alternatively, the vectors containing putative desaturase sequences can be expressed in leaves or used to generate transgenic crown galls.

The resulting desaturase sequences identified and isolated using methods such as those disclosed above are then cloned into plant expression and transformation vectors such as those disclosed below using well known methods in molecular biology such as those disclosed in Sambrook, Fritsch and Maniatis, Molecular Cloning: A Laboratory Manual, $2^{nd}$ edition (1989) or Current Protocols in Molecular Biology, F. M. Ausubel et al., eds. (1987).

Expression of Desaturase Genes

For expression of a desaturase polypeptide, functional transcriptional and translational initiation and termination regions are operably linked to the DNA encoding the desaturase polypeptide. Transcriptional and translational initiation and termination regions are derived from a variety of sources, including the DNA to be expressed, genes known or suspected to be capable of expression in the desired system, expression vectors, chemical synthesis or from an endogenous locus in a host cell. Expression in a plant tissue and/or plant part provides certain advantages, particularly where the tissue or part is one that is easily harvested, such as seed, leaves, fruits, flowers, roots, etc. Expression can be targeted to that location within the plant by using specific regulatory sequences, such as those of U.S. Pat. Nos. 5,463,174, 4,943,674, 5,106,739, 5,175,095, 5,420,034, 5,188,958 and 5,589,379, which are hereby incorporated by reference in their entirety and for the specific sequences disclosed therein. One particularly useful localization of GLA produced by this invention is in the seed tissue of host plant cells. To direct expression in the seed, seed specific promoters may be used to direct expression of the appropriate desaturases. Examples of such seed specific promoters include those disclosed in U.S. Pat. Nos. 5,623,067, 6,342,657 and 6,642,437, which are hereby incorporated by reference in their entirety and for the specific sequences disclosed therein.

Expression in a host cell can be accomplished in a transient or stable fashion. Transient expression can occur from introduced constructs that contain expression signals functional in the host cell, but where the constructs do not replicate and rarely integrate in the host cell or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Suitable selection markers include resistance to the herbicide Basta provided by the pat (phosphothricin acetyl transferase) gene and resistance to kanamycin provided by the nptII (neomycin phosphotransferase) gene, among other genes known in the art. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

For expression of the desaturase polypeptide in seeds a seed-specific promoter can be employed. Examples of such promoters include the oleosin or linin promoters. The oleosin promoter is disclosed in U.S. Pat. No. 5,792,922 and the linin promoter is disclosed in U.S. Pat. No. 6,777,591.

When it is desirable to express more than one distinct gene, the genes can be contained within a single construct or the genes can be on separate vectors. In either case, one of skill in the art would exercise judicious choice in choosing regulatory regions, selection means and methods of propagation of the introduced construct(s) to provide for optimal expression levels of all enzymes required for the synthesis of the desired products.

Constructs comprising the gene of interest may be introduced into a host cell by standard techniques. These techniques include transfection, infection, biolistic impact, electroporation, microinjection, scraping or any other method that introduces the gene of interest into the host cell (see U.S. Pat. Nos. 4,743,548, 4,795,855, 5,068,193, 5,188,958, 5,463,174, 5,565,346 and 5,565,347). For convenience, a host cell that has been manipulated by any method to take up a DNA sequence or construct will be referred to as "transformed" or "recombinant" herein. The subject host will have at least have one copy of the expression construct and may have two or more, depending upon whether the gene is integrated into more than one site in the genome, with multiple copies at one loci, is amplified and/or is present on an extrachromosomal element having multiple copy numbers.

A variety of plant transformation methods are known. The Δ6- and Δ12-desaturase genes can be introduced into plants through *Agrobacterium* co-cultivation by a leaf disk transformation-regeneration procedure as described by Horsch et al., Science 227: 1229, 1985. Other methods of *Agrobacterium*-mediated transformation, such as co-cultivation of protoplast (Horsch et al., Science 223:496, 1984; DeBlock et al., EMBO J. 2:2143, 1984), suspension culture of transformed cells (Barton et al., Cell 32:1033, 1983) or vacuum infiltration of flowers (Bechtold et al., CR Acad Scie III, Sci Vie 316:1194, 1993; Wang et al., Plant Cell Rep 22:274, 2003), can also be used and are within the scope of this invention. In a preferred aspect, plants are transformed with *Agrobacterium*-derived or *Agrobacterium*-immobilized vectors such as those described in Klee et al., Annu Rev Plant Physiol 38: 467, 1987. However, other methods are available to insert the Δ6- and Δ12-desaturase genes of the present invention into plant cells. Such alternative methods include, but not limited to, biolistic approaches (Klein et al., Nature 327:70, 1987), protoplast approaches (Shillito and Potrykus, Recombinant DNA Methodology 687, 1989; Davey et al., Plant Mol Biol 13:273, 1989) chemically-induced DNA uptake (Töpfer et al., Plant Cell 1:133, 1989) and use of viruses or pollen (Ohta, PNAS 83:715, 1986) as vectors.

When necessary for the transformation method, the Δ6- and Δ12-desaturase genes of the present invention can be inserted into a plant transformation vector, e.g., the binary vector described by Bevan (1984) Nucleic Acids Res. 12, 8111. Plant transformation vectors can be derived by modifying the natural gene transfer system of *Agrobacterium tumefacians*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences. The T-region also contains a selectable marker for antibiotic resistance and a multiple cloning site for inserting sequences for transfer. Such engineered strains are known as "disarmed" *A. tumefaciens* strains and allow the efficient transformation of sequences bordered by the T-region into the nuclear genomes of plants.

Surface-sterilized leaf disks are inoculated with the "disarmed" foreign DNA-containing *A. tumefaciens*, cultured for two days and then transferred to antibiotic-containing medium. Transformed shoots are elected after rooting in medium containing the appropriate antibiotic, transferred to soil and regenerated.

A transformed host cell can be identified by selection for a marker contained on the introduced construct. Alternatively, a separate marker construct may be introduced with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene therefore may confer antibiotic resistance or encode an essential growth factor or enzyme and permit growth on selective media when expressed in the transformed host cell. Desirably, resistance to kanamycin and the amino glycoside G418 are of interest (see U.S. Pat. No. 5,034,322). Selection of a transformed host can also occur when the expressed marker protein can be detected, either directly or indirectly. The marker protein may be expressed alone or as a fusion to another protein. The marker protein can be detected by its enzymatic activity; for example, β-galactosidase can convert the substrate X-gal to a colored product and luciferase can convert luciferin to a light-emitting product. The marker protein can be detected by its light-producing or modifying characteristics, for example, the green fluorescent protein of *Aequorea victoria* fluoresces when illuminated with blue light. Antibodies can be used to detect the marker protein or a molecular tag on, for example, a protein of interest. Cells expressing the marker protein or tag can be selected, for example, visually or by techniques such as FACS or panning using antibodies.

Transformation of Safflower

At least two basic distinct methods exist for the transformation of safflower plants: (1) shoot regeneration from a callus, which is induced from co-cultivated cotyledons and (2) multiple shoot regeneration directly from co-cultivated excised meristems.

Method 1 involves induction of a callus from cotyledonary explants subsequent to co-cultivation with *Agrobacterium* (Ying et al., Plant Cell Rep 11:581, 1992); Orlikowska et al., PCTOC 40:85, 1995). The method consists of co-cultivating excised cotyledons during 3 days on callus induction medium (MS salts with B5 vitamins). Explants are transferred to shoot formation medium (MS salts, B5 vitamins and carbenicillin) and cultured for 2 days and then transferred to the same medium containing kanamycin. After 2 to 3 weeks, regenerating leafy structures are transferred together with underlying explant tissue to shoot elongation medium (½MS salts and MS vitamins) containing Geneticin®. After an additional 2 to 3 weeks, elongating shoots are detached from the original explant tissue and transferred to the same medium, at which point the cut ends of non-transformed or chimeric shoots rapidly turn brown while transgenic shoots remain healthy. Healthy shoots are transferred to rooting medium (½MS salts and MS vitamins) when at least 10 mm in length. An average of 2-3 shoots regenerate from one explant.

With method 2, multiple shoots are briefly induced from excised meristems prior to cocultivation with *Agrobacterium* (Rao and Rohini, Plant Biotechnol 16:201, 1999); Rohini and Rao, Annals Bot 86:1043, 2000). It involves using a needle to prick the embryo axis of germinating seeds that have had one of the cotyledons removed at the cotyledonary node. The embryo is then immersed and gently agitated at 28-30° C. in a suspension of *Agrobacterium* in Winans's AB medium for 10 minutes. Following co-cultivation on semi-solid MS basal medium for 24 hours, embryo axes are washed thoroughly with 500 μg/ml of cefotaxime in liquid MS basal medium with gentle agitation (80 rpm) for 1 hour and placed on autoclaved Soilrite (vermiculite equivalent) (Chowgule Industries Ltd. Bangalore, India) moistened with water for germination under aseptic conditions in a growth room. After 5 to 6 days, the germlings are transferred to Soilrite in pots and allowed to grow under growth room conditions for at least 10 days before they are transferred to the greenhouse. The pots are initially covered with polythene bags to maintain humidity. The growth chamber is maintained at 26-28° C. under a 14-hour photoperiod with a fluorescent light. In contrast to method 1, the majority of shoots produced with this method generally do not show vitrification. The developing plantlets might be chimeric and, in that case, successful transformation depends on whether T-DNA is integrated in the meristematic cell layer that generates the future reproductive organs. This method requires substantially more starting material (mature seed) and growth chamber space than method 1.

A preferred aspect of the present disclosure provides transgenic safflower plants or progeny of these plants expressing DNA encoding desaturases that overproduce GLA. Safflower is an advantageous host plant because it is widely used as a source of vegetable oils. Safflower plant cells are transformed with the isolated DNA encoding Δ6-desaturase or Δ6-desaturase and Δ12-desaturases by any of the plant transformation methods described above. The transformed safflower plant cell, usually in a callus culture or leaf disk, is regenerated into a complete transgenic plant by methods well known to one of ordinary skill in the art (e.g., Horsch et al., Science 227:1129, 1985). Since progeny of transformed safflower plants inherit the DNA encoding desaturase genes, seeds or cuttings from transformed plants are used to maintain the transgenic plant line.

In one specific aspect, the method comprises introducing DNA encoding Δ6-desaturase into safflower plants that lack GLA or have low levels of GLA but produce LA. In another aspect, the method comprises introducing one or more expression vectors that comprise DNA encoding Δ12-desaturase and Δ6-desaturase safflower plants that are deficient in both GLA and LA. Accordingly, safflower plants deficient in both LA and GLA are induced to produce LA by the expression of Δ12-desaturase and GLA is then generated due to the expression of Δ6-desaturase. Expression vectors comprising DNA encoding Δ12-desaturase or Δ12-desaturase and Δ6-desaturase can be constructed by methods of recombinant technology known to one of ordinary skill in the art (Sambrook et al., 1989) and the published sequence of Δ12-desaturase (Wada et al., Nature (London) 347:200, 1990). Examples of such vectors are disclosed herein.

Oil Containing GLA

The resulting GLA in safflower plants can be extracted from various safflower plant parts, particularly seeds, utilizing methods well known in the art as described above. In particular, seeds are harvested and the oil from the safflower seed can be extracted, typically by crushing the seed, and then refined using any conventional method. Methods for extracting oil from safflower seeds are well known in the art and are presented in sources such as Smith, J. R., Safflower, AOCS Press, pp. 185-212 (1996).

The GLA produced using the subject methods and compositions may be found in the host plant tissue and/or plant part as free fatty acids or in esterified forms, such as acylglycerols, phospholipids, sulfolipids or glycolipids, and may be extracted from the host cell through a variety of means well known in the art. Such means may include extraction with organic solvents, sonication, supercritical fluid extraction using for example carbon dioxide and physical means such as presses or combinations thereof. Of particular interest is extraction with hexane, propane, acetone or ethanol.

The GLA described herein can be included in nutritional and personal care compositions. Examples of nutritional compositions invention include but are not limited to infant formulas, dietary supplements, dietary substitutes and rehydration compositions. For example, the composition may be added to food of any type including but not limited to margarines, modified butters, cheeses, milk, yogurt, chocolate, candy, snacks, salad oils, cooking oils, cooking fats, meats, fish and beverages. Examples of personal care compositions include skin creams, balms and lotions, moisturizers, tanning and after tanning products, shampoos, hair conditioners and lipsticks. Examples of uses to which the GLA of this invention can be applied are described, for example, in U.S. Pat. Nos. 6,635,451 and 5,709,888, which are hereby incorporated by reference in their entirety and for the specific uses disclosed therein.

The patents cited herein are incorporated by reference in their entirety. The following Examples are provided by way of illustration and are not intended to limit the scope of the invention.

EXAMPLES

Example 1

Plasmid pSBS4766 and Transgenic Plants Expressing this Plasmid

Figure 8:
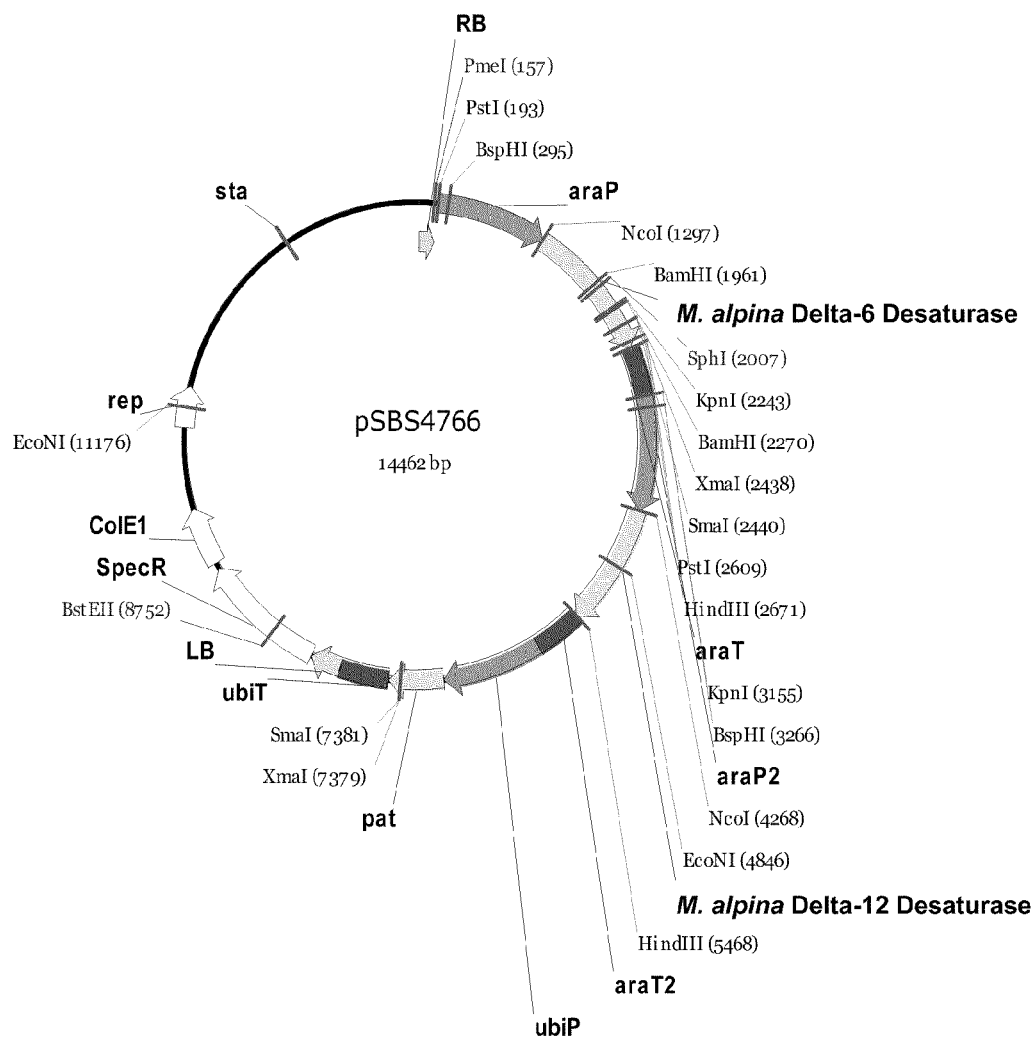
FIG. 8 shows plasmid pSBS4766 for the expression of Δ6- and Δ12-desaturase from the organism *M. alpina*. Shown are various features of the expression construct including promoters, termination sequences and resistance and marker genes. The plant selectable marker on this plasmid is pat, the phosphinothricin acetyl transferase from *Streptomyces viridochromogenes*. The bacterial marker is SpecR.

FIG. 8 shows the map of a construct used to co-express the Δ6-desaturase and Δ12-desaturase from *Mortierella alpina*. The plant selectable marker used in this construct was pat which corresponds to the phosphinothricin acetyl transferase gene from *Streptomyces viridochromogenes*. The bacterial marker used in this construct was SpecR. The base binary vector used to construct this vector is a derivative of pPZP200. See Hajdukiewicz et al. Plant Mol Biol 25: 989, 1994. The sequence of the insert contained within the borders of the pPZP200 plasmid is shown below.

pSBS4766 (*M. alpina* Δ6- and Δ12-desaturase double expression cassette with PAT selection) (SEQ ID NO: 1)

```
ctgcaggaattcgatctctattgattcaaattacgatctgatactgataa
cgtctagatttttagggttaaagcaatcaatcacctgacgattcaaggtg
gttggatcatgacgattccagaaaacatcaagcaagctctcaaagctaca
ctctttgggatcatactgaactctaacaacctcgttatgtcccgtagtgc
cagtacagacatcctcgtaactcggattgtgcacgatgccatgactatac
ccaacctcggtcttggtcacaccaggaactctctggtaagctagctccac
tccccagaaacaaccggcgccaaattgcgcgaattgctgacctgaagacg
gaacatcatcgtcgggtccttgggcgattgcggcggaagatgggtcagct
tgggcttgaggacgagacccgaatccgagtctgttgaaaaggttgttcat
tggggatttgtatacggagattggtcgtcgagaggtttgagggaaaggac
aaatgggtttggctctggagaaagagagtgcggctttagagagagaattg
agaggtttagagagagatgcggcggcgatgagcggaggagagacgacgag
gacctgcattatcaaagcagtgacgtggtgaaatttggaacttttaagag
gcagatagatttattatttgtatccattttcttcattgttctagaatgtc
gcggaacaaattttaaaactaaatcctaaattttctaattttgttgcca
atagtggatatgtgggccgtatagaaggaatctattgaaggcccaaaccc
atactgacgagcccaaaggttcgttttgcgttttatgtttcggttcgatg
ccaacgccacattctgagctaggcaaaaaacaaacgtgtctttgaataga
ctcctctcgttaacacatgcagcggctgcatggtgacgccattaacacgt
ggcctacaattgcatgatgtctccattgacacgtgacttctcgtctcctt
tcttaatatatctaacaaacactcctacctcttccaaaatatatacacat
cttttgatcaatctctcattcaaaatctcattctctctagtaaacaaga
acaaaaaaccatggctgctgctcccagtgtgaggacgtttactcgggccg
aggttttgaatgccgaggctctgaatgagggcaagaaggatgccgaggca
cccttcttgatgatcatcgacaacaaggtgtacgatgtccgcgagttcgt
ccctgatcatcccggtggaagtgtgattctcacgcacgttggcaaggacg
gcactgacgtctttgacactttcacccgcaggctgcttgggagactctt
gccaacttttacgttggtgatattgacgagagcgaccgcgatatcaagaa
tgatgactttgcggccgaggtccgcaagctgcgtaccttgttccagtctc
ttggttactacgattatccaaggcatactacgccttcaaggtctcgttca
acctctgcatctgggtttgtcgacggtcattgtggccaagtggggccag
acctcgaccctcgccaacgtgctctcggctgcgcttttgggtctgttctg
gcagcagtgcggatggttggctcacgacttttttgcatcaccaggtcttcc
aggaccgtttctggggtgatcttttcggcgccttcttgggaggtgtctgc
cagggcttctcgtcctcgtggtggaaggacaagcacaacactcaccacgc
cgccccaacgtccacggcgaggatcccgacattgacacccaccctctgt
tgacctggagtgagcatgcgttggagatgttctcggatgtcccagatgag
gagctgacccgcatgtggtcgcgtttcatggtcctgaaccagacctggtt
ttacttccccattctctcgtttgcccgtctctcctggtgcctccagtcca
ttctctttgtgctgcctaacggtcaggcccacaagccctcgggcgcgcgt
gtgcccatctcgttggtcgagcagctgtcgcttgcgatgcactggacctg
gtacctcgccaccatgttcctgttcatcaaggatcccgtcaacatgctgg
tgtacttttggtgtcgcaggcggtgtgcggaaacttgttggcgatcgtg
ttctcgctcaaccacaacggtatgcctgtgatctcgaaggaggagcggt
cgatatggatttcttcacgaagcagatcatcacgggtcgtgatgtccacc
cgggtctatttgccaactggttcacgggtggattgaactatcagatcgag
caccacttgttccttcgatgcctcgccacaacttttcaaagatccagcc
tgctgtcgagaccctgtgcaaaaagtacaatgtccgataccacaccaccg
gtatgatcgagggaactgcagaggtatttagccgtctgaacgaggtctcc
aaggctgcctccaagatgggtaaggcgcagtaagcttgttaccccactga
tgtcatcgtcatagtccaataactccaatgtcggggagttagtttatgag
```

-continued

```
gaataaagtgtttagaatttgatcaggggagataataaaagccgagttt
gaatcttttgttataagtaatgtttatgtgtgtttctatatgttgtcaa
atggtcccatgttttcttcctctcttttgtaacttgcaagtgttgtgt
tgtactttatttggcttctttgtaagttggtaacggtggtctatatatgg
aaaaggtcttgttttgttaaacttatgttagttaactggattcgtcttta
accacaaaaagttttcaataagctacaaatttagacacgcaagccgatgc
agtcattagtacatatatttattgcaagtgattacatggcaacccaaact
tcaaaaacagtaggttgctccatttagtaacctgaattgcctcctgattc
tagttgatcccggtaccgaattccaggaattcgatctctattgattcaaa
ttacgatctgatactgataacgtctagatttttagggttaaagcaatcaa
tcacctgacgattcaaggtggttggatcatgacgattccagaaaacatca
agcaagctctcaaagctacactattgggatcatactgaactctaacaacc
tcgttatgtcccgtagtgccagtacagacatcctcgtaactcggattgtg
cacgatgccatgactatacccaacctcggtcttggtcacaccaggaactc
tctggtaagctagctccactccccagaaacaaccggcgccaaattgcgcg
aattgctgacctgaagacggaacatcatcgtcgggtccttgggcgattgc
ggcggaagatgggtcagcttgggcttgaggacgagacccgaatccgagtc
tgttgaaaaggttgttcattggggatttgtatacggagattggtcgtcga
gaggtttgagggaaaggacaaatgggtttggctctggagaaagagagtgc
ggctttagagagagaattgagaggtttagagagagatgcggcggcgatga
gcggaggagagacgacgaggacctgcattatcaaagcagtgacgtggtga
aatttggaacttttaagaggcagatagatttattatttgtatccattttc
ttcattgttctagaatgtcgcggaacaaattttaaaactaaatcctaaat
ttttctaattttgttgccaatagtggatatgtgggccgtatagaaggaat
ctattgaaggcccaaacccatactgacgagcccaaaggttcgttttgcgt
tttatgtttcggttcgatgccaacgccacattctgagctaggcaaaaaac
aaacgtgtcttgaatagactcctctcgttaacacatgcagcggctgcat
ggtgacgccattaacacgtggcctacaattgcatgatgtctccattgaca
cgtgacttctcgtctccttcttaatatatctaacaaacactcctacctc
ttccaaaatatatacacatcttttgatcaatctctcattcaaaatctca
ttctctctagtaaacaagaacaaaaaaccatggcacctcccaacactatc
gatgccggtttgacccagcgtcatatcagcacctcggccccaaactcggc
caagcctgccttcgagcgcaactaccagctccccgagttcaccatcaagg
agatccgagagtgcatccctgcccactgctttgagcgctccggtctccgt
ggtctctgccacgttgccatcgatctgacttgggcgtcgctcttgttcct
ggctgcgacccagatcgacaagtttgagaatcccttgatccgctatttgg
cctggcctgtttactggatcatgcagggtattgtctgcaccggtgtctgg
gtgctggctcacgagtgtggtcatcagtccttctcgacctccaagacccct
caacaacacagttggttggatcttgcactcgatgctcttggtcccctacc
actcctggagaatctcgcactcgaagcaccacaaggccactggccatatg
accaaggaccaggtctttgtgcccaagacccgctcccaggttggcttgcc
```

-continued

```
tcccaaggagaacgctgctgctgccgttcaggaggaggacatgtccgtgc
acctggatgaggaggctcccattgtgactttgttctggatggtgatccag
ttcttgttcggatggcccgcgtacctgattatgaacgcctctggccaaga
ctacggccgctggacctcgcacttccacacgtactcgcccatctttgagc
cccgcaacttttttcgacattattatctcggacctcggtgtgttggctgcc
ctcggtgccctgatctatgcctccatgcagttgtcgctcttgaccgtcac
caagtactatattgtccctacctctttgtcaacttttggttggtcctga
tcaccttcttgcagcacaccgatcccaagctgccccattaccgcgagggt
gcctggaatttccagcgtggagctctttgcaccgttgaccgctcgtttgg
caagttcttggaccatatgttccacggcattgtccacacccatgtggccc
atcacttgttctcgcaaatgccgttctaccatgctgaggaagctacctat
catctcaagaaactgctgggagagtactatgtgtacgacccatccccgat
cgtcgttgcggtctggaggtcgttccgtgagtgccgattcgtggaggatc
agggagacgtggtattttttcaagaagtaagcttgttaccccactgatgtc
atcgtcatagtccaataactccaatgtcggggagttagtttatgaggaat
aaagtgtttagaatttgatcaggggagataataaaagccgagtttgaat
cttttgttataagtaatgtttatgtgtgtttctatatgttgtcaaatgg
tcccatgttttcttcctctcttttgtaacttgcaagtgttgtgttgta
ctttatttggcttctttgtaagttggtaacggtggtctatatatggaaaa
ggtcttgttttgttaaacttatgttagttaactggattcgtctttaacca
caaaaagttttcaataagctacaaatttagacacgcaagccgatgcagtc
attagtacatatatttattgcaagtgattacatggcaacccaaacttcaa
aaacagtaggttgctccatttagtaacctgaattgcctcctgattctagt
tgatcccggtgaatccaaaaattacggatatgaatataggcatatccgta
tccgaattatccgtttgacagctagcaacgattgtacaattgcttcttta
aaaaaggaagaaagaaagaaagaaaagaatcaacatcagcgttaacaaac
ggccccgttacggcccaaacggtcatatagagtaacggcgttaagcgttg
aaagactcctatcgaaatacgtaaccgcaaacgtgtcatagtcagatccc
ctcttccttcaccgcctcaaacacaaaaataatcttctacagcctatata
tacaaccccccttctatctctcctttctcacaattcatcatctttctttt
ctctaccccaattttaagaaatcctctcttctcctcttcatttttcaagg
taaatctctctctctctctctctctctgttattccttgtttttaattaggt
atgtattattgctagtttgttaatctgcttatcttatgtatgccttatgt
gaatatctttatcttgttcatctcatccgtttagaagctataaatttgtt
gatttgactgtgtatctacacgtggttatgtttatatctaatcagatatg
aatttcttcatattgttgcgtttgtgtgtaccaatccgaaatcgttgatt
tttttcatttaatcgtgtagctaattgtacgtatacatatggatctacgt
atcaattgttcatctgttttgtgtttgtatgtatacagatctgaaaacatc
acttctctcatctgattgtgttgttacatacatagatatagatctgttat
atcattttttttattaattgtgtatatatatatgtgcatagatctggatta
```

```
catgattgtgattatttacatgattttgttatttacgtatgtatatgt
agatctggacttttggagttgttgacttgattgtatttgtgtgtgtata
tgtgtgttctgatcttgatatgttatgtatgtgcagccaaggctacgggc
gatccaccatgtctccggagaggagaccagttgagattaggccagctaca
gcagctgatatggccgcggtttgtgatatcgttaaccattacattgagac
gtctacagtgaactttaggacagagccacaaacaccacaagagtggattg
atgatctagagaggttgcaagatagatacccttggttggttgctgaggtt
gagggtgttgtggctggtattgcttacgctgggccctggaaggctaggaa
cgcttacgattggacagttgagagtactgtttacgtgtcacataggcatc
aaaggttgggcctaggttccacattgtacacacatttgcttaagtctatg
gaggcgcaaggttttaagtctgtggttgctgttataggccttccaaacga
tccatctgttaggttgcatgaggctttgggatacacagcccggggtacat
tgcgcgcagctggatacaagcatggtggatggcatgatgttggttttttgg
caaagggattttgagttgccagctcctccaaggccagttaggccagttac
ccagatctgagtcgaccgaatgagttccaagatggtttgtgacgaagtta
gttggttgttttatggaactttgtttaagctagcttgtaatgtggaaag
aacgtgtggcttgtggttttttaaatgttggtgaataaagatgtttccttt
tggattaactagtatttttcctattggtttcatggttttagcacacaaca
ttttaaatatgctgttagatgatatgctgcctgctttattatttacttac
ccctcaccttcagtttcaaagttgttgcaatgactctgtgtagtttaaga
tcgagtgaaagtagattttgtctatatttattaggggtatttgatatgct
aatggtaaacatggtttatgacagcgtactttttttggttatggtgttgac
gtttccttttaaacattatagtagcgtccttggtctgtgttcattggttg
``` aacaaaggcacactcacttggagatgccgtctccactgatatttgaacaa
a

Transformation of safflower with this construct was performed by SemBioSys Genetics Inc. (Calgary, Canada). Techniques utilized by SemBioSys Genetics Inc. include those described in WO 2004/111244, which is hereby incorporated by reference in its entirety. Transgenic plants were grown and seed were harvested.

Measurement of fatty acid levels was performed in seeds derived from transgenic plants. Seeds were collected from transgenic plants and fatty acid composition was determined by gas chromatography using a modification of a method described in "Official Methods and Recommended Practices of the AOCS", 5$^{th}$ Ed., Method Ce 1-62, American Oil Chemists Society: Champaign, Ill. (1997). In this method, oil is hexane extracted from the seed, hydrolyzed with hydrochloric acid and reacted with methanol to form methyl esters. The methyl esters are then quantified against an internal standard by gas chromatography.

The fatty acid composition in 10 seed pools of T1 seed of transgenic plants expressing the pSBS4766 construct are shown in Table 1 below. The activity of the Δ6-desaturase gene is clearly evidenced by the presence of GLA in the transgenic lines. While GLA ranges from 0.03% to 0.04% in the S317 controls in Table 1, it ranges form 0.5% to 30.8% in the T1 pooled seeds. This is over a fifty-fold increase in the concentration of GLA. Small but significant increases in the 18:4 are seen in the lines with the highest GLA. This is expected, as the Δ6-desaturase gene can act both on 18:2 to produce GLA and 18:3 (ALA) to produce 18:3. The activity of the Δ12-desaturase is evidenced by the decrease in 18:1 fatty acids. In the S317 controls in Table 1, the OA ranges from 73.76% to 75.8% while in the transgenic lines in ranges from 3.68% to 73.51%. Overall, the data show a wide range of GLA concentrations that can be achieved in safflower via this invention.

TABLE 1

Examples of fatty acid composition (expressed as percentages) in 10 seed pools of T1 seed of pSBS4766 construct expressed in S317

| Table 1 Line number | C16:0 (Palmitic) | C18:0 (Stearic) | C18:1n9 (Oleic) | C18:2 other | C18:2n6 (Linoleic) | C18:3n6 (gamma-Linolenic) | C18:3n3 (alpha-Linolenic) | C18:4n3 (Octadecatetraenoic) |
|---|---|---|---|---|---|---|---|---|
| 4766-24 | 7.40 | 1.87 | 3.68 | | 53.00 | 30.80 | 0.66 | 0.17 |
| 4766-12 | 6.77 | 1.78 | 3.69 | | 54.22 | 30.48 | 0.68 | 0.16 |
| 4766-27 | 6.71 | 1.78 | 18.73 | | 46.82 | 23.18 | 0.60 | 0.13 |
| 4766-1 | 6.52 | 1.64 | 20.06 | | 45.88 | 22.35 | 0.99 | 0.13 |
| 4766-30 | 6.44 | 1.63 | 17.51 | | 56.99 | 15.16 | 0.34 | 0.02 |
| 4766-21 | 5.91 | 1.64 | 17.04 | | 58.00 | 15.11 | 0.52 | 0.03 |
| 4766-11 | 6.06 | 1.56 | 14.38 | | 60.75 | 14.99 | 0.44 | 0.04 |
| 4766-26 | 6.34 | 1.66 | 15.64 | | 61.66 | 12.48 | 0.39 | |
| 4766-13 | 5.83 | 1.67 | 27.48 | | 49.92 | 12.30 | 0.72 | 0.04 |
| 4766-19 | 5.94 | 1.74 | 23.34 | | 55.54 | 11.08 | 0.44 | 0.02 |
| 4766-10 | 5.70 | 1.53 | 24.56 | | 57.28 | 8.68 | 0.40 | 0.01 |
| 4766-5 | 5.31 | 1.73 | 33.82 | | 48.63 | 8.24 | 0.38 | 0.01 |
| 4766-31 | 5.27 | 1.51 | 46.85 | | 36.17 | 7.77 | 0.30 | 0.01 |
| 4766-4 | 4.50 | 1.34 | 73.51 | 1.89 | 11.14 | 5.08 | 0.32 | 0.01 |
| 4766-14 | 5.40 | 1.66 | 11.74 | | 74.16 | 4.93 | 0.37 | 0.01 |
| 4766-41 | 4.74 | 1.58 | 54.76 | 0.66 | 33.36 | 2.66 | 0.16 | |
| 4766-22 | 5.13 | 1.5 | 58.60 | | 31.92 | 0.50 | 0.21 | |
| Centennial | 6.94 | 1.88 | 11.31 | | 76.74 | 0.07 | 0.38 | |
| S317 | 4.92 | 2.25 | 73.76 | | 16.34 | 0.04 | 0.28 | |
| S317 | 4.72 | 2.31 | 74.73 | | 15.76 | 0.04 | 0.07 | |
| S317 | 4.57 | 2.25 | 75.80 | | 14.96 | 0.03 | 0.07 | |

The fatty acid composition in single seed samples from the S317 control line is shown in Table 2 below. Four replicates (S0-1, S0-2, S0-3, S0-4) were run. The single seed data parallel the seed pool data.

TABLE 2

The fatty acid composition in four single seed samples from the control line (S317, denoted S0).

| Table 2 - Fatty Acids | S0-1 | S0-2 | S0-3 | S0-4 |
|---|---|---|---|---|
| C10:0 Capric | 0.7% | 0.3% | 0.5% | 0.5% |
| C11:0 | 0.3% | 0.1% | 0.3% | 0.2% |
| C12:0 Lauric | 0.2% | 0.1% | 0.2% | 0.1% |
| C13:0 Tridecanoic | 0.0% | 0.0% | 0.0% | 0.0% |
| C14:0 Myristic | 0.3% | 0.2% | 0.2% | 0.2% |
| C14:1w5, Myristoleic | 0.2% | 0.0% | 0.1% | 0.1% |
| C15:0 Pentadecanoic | 0.0% | 0.0% | 0.0% | 0.0% |
| C15:1w5cis 10-Pentadecenoid | 0.0% | 0.0% | 0.1% | 0.0% |
| C16:0 Palmitic | 6.0% | 6.2% | 5.7% | 5.7% |
| C16:1w7c Palmitoleic | 0.2% | 0.1% | 0.1% | 0.2% |
| C17:0 Heptadecanoic | 0.1% | 0.1% | 0.1% | 0.1% |
| c17:1w7 | 0.0% | 0.0% | 0.0% | 0.1% |
| C18:0 Stearic | 3.2% | 1.8% | 3.4% | 1.7% |
| C18:1w9t | 0.1% | 0.1% | 0.1% | 0.1% |
| C18:1w9c INTERNAL STANDARD | 73.0% | 74.2% | 74.3% | 75.6% |
| C18:2w6t | 0.1% | 0.0% | 0.1% | 0.0% |
| C18:2w6c Linoleic (LA) | 13.6% | 14.8% | 12.9% | 13.5% |
| C20:0 Arachidic | 0.4% | 0.5% | 0.5% | 0.5% |
| C18:3w6 γ-linolenic (GLA) | 0.0% | 0.0% | 0.0% | 0.0% |
| C20:1w9 | 0.3% | 0.3% | 0.3% | 0.3% |
| C18:3w3, α-linolenic (ALA) | 0.1% | 0.1% | 0.1% | 0.1% |
| C21:0 Heneicosanoic | 0.1% | 0.1% | 0.1% | 0.1% |
| C20:2w6 Eicosadienoic | 0.0% | 0.0% | 0.0% | 0.0% |
| C22:0 Behenic | 0.3% | 0.3% | 0.3% | 0.3% |
| C20:3w6 Dihomo-γ-linolenic (DGLA) | 0.0% | 0.0% | 0.0% | 0.0% |
| C22:1w9 Erucic | 0.0% | 0.0% | 0.0% | 0.0% |
| C20:3w3 | 0.0% | 0.0% | 0.0% | 0.0% |
| C20:4w6 Arachidonic (AA) | 0.0% | 0.0% | 0.0% | 0.0% |
| C23:0 Tricosanoic | 0.0% | 0.0% | 0.0% | 0.0% |
| C22:2w6 | 0.1% | 0.0% | 0.1% | 0.1% |
| C24:0 Lignoceric | 0.2% | 0.2% | 0.2% | 0.2% |
| C20:5w3 Eicosapentaenoic (EPA) | 0.1% | 0.0% | 0.0% | 0.0% |
| C24:1w9c | 0.1% | 0.2% | 0.1% | 0.1% |
| C22:6w3 Docosahexaenoic (DHA) | 0.3% | 0.1% | 0.1% | 0.1% |
| Total fatty acids | 100.0% | 100.0% | 100.0% | 100.0% |
| Saturated fatty acids | 11.8% | 9.8% | 11.5% | 9.6% |
| Total W7's & W5's | 0.4% | 0.3% | 0.4% | 0.4% |
| Total W9's | 73.4% | 74.6% | 74.6% | 76.0% |
| Total W6's | 13.8% | 14.9% | 13.1% | 13.7% |
| Total W3's | 0.5% | 0.2% | 0.2% | 0.2% |
| Total monounsaturated fatty acids | 73.7% | 74.9% | 75.0% | 76.4% |
| Total trans fatty acids | 0.2% | 0.1% | 0.2% | 0.1% |
| Polyunsaturated fatty acids | 14.2% | 15.1% | 13.3% | 13.9% |
| Ratios: | | | | |
| Polyunsaturated/saturated | 1.2 | 1.5 | 1.2 | 1.5 |
| Omega 6/Omega 3 | 30.1 | 72.5 | 61.6 | 60.8 |
| AA/EPA | 0.2 | 0.1 | 1.0 | 0.8 |
| AA/DHA | 0.0 | 0.1 | 0.4 | 0.4 |

The fatty acid composition in single seeds from 5 lines (S1, S4, S5, S24, S27) of transgenic plants expressing the pSBS4766 construct are shown in Tables 3-7 below. Data from 8 to 9 replicate seeds are provided. When available, values for single seeds of a NULL control line for each transgenic line are provided for comparison.

TABLE 3

Individual Seed Samples of Transgenic Line S1

| Fatty Acids | NULL | S1-1 | S1-2 | S1-3 | S1-4 | S1-5 | S1-6 | S1-7 | S1-8 |
|---|---|---|---|---|---|---|---|---|---|
| C10:0 Capric | 0.6% | 0.6% | 0.4% | 0.6% | 0.5% | 0.4% | 0.4% | 0.1% | 0.6% |
| C11:0 | 0.2% | 0.2% | 0.2% | 0.3% | 0.1% | 0.1% | 0.1% | 0.1% | 0.2% |
| C12:0 Lauric | 0.1% | 0.1% | 0.1% | 0.1% | 0.1% | 0.1% | 0.1% | 0.1% | 0.1% |
| C13:0 Tridecanoic | 0.0% | 0.0% | 0.0% | 0.0% | 0.0% | 0.0% | 0.0% | 0.0% | 0.0% |
| C14:0 Myristic | 0.1% | 0.3% | 0.3% | 0.3% | 0.2% | 0.3% | 0.2% | 0.2% | 0.2% |
| C14:1w5, Myristoleic | 0.1% | 0.1% | 0.1% | 0.2% | 0.1% | 0.1% | 0.1% | 0.1% | 0.1% |
| C15:0 Pentadecanoic | 0.0% | 0.0% | 0.1% | 0.1% | 0.1% | 0.1% | 0.1% | 0.1% | 0.1% |
| C15:1w5cis 10-Pentadecenoid | 0.0% | 0.0% | 0.0% | 0.0% | 0.0% | 0.0% | 0.0% | 0.0% | 0.0% |
| C16:0 Palmitic | 5.4% | 6.1% | 8.7% | 8.9% | 8.5% | 8.0% | 8.6% | 8.9% | 8.2% |
| C16:1w7c Palmitoleic | 0.2% | 0.3% | 0.1% | 0.1% | 0.1% | 0.2% | 0.2% | 0.1% | 0.2% |
| C17:0 Heptadecanoic | 0.1% | 0.2% | 0.2% | 0.2% | 0.2% | 0.2% | 0.2% | 0.1% | 0.1% |
| c17:1w7 | 0.1% | 0.1% | 0.0% | 0.0% | 0.0% | 0.0% | 0.0% | 0.0% | 0.0% |
| C18:0 Stearic | 2.2% | 1.6% | 3.2% | 2.5% | 1.4% | 3.6% | 2.9% | 1.4% | 2.1% |
| C18:1w9t | 0.1% | 0.1% | 0.0% | 0.1% | 0.0% | 0.0% | 0.0% | 0.0% | 0.0% |
| C18:1w9c INTERNAL STANDARD | 74.9% | 59.8% | 0.7% | 0.8% | 0.8% | 0.7% | 0.7% | 0.7% | 0.7% |
| C18:2w6t | 0.0% | 0.0% | 0.0% | 0.1% | 0.0% | 0.0% | 0.0% | 0.0% | 0.0% |
| C18:2w6c Linoleic (LA) | 14.0% | 27.3% | 37.8% | 33.7% | 48.9% | 47.7% | 41.4% | 39.3% | 41.0% |
| C20:0 Arachidic | 0.3% | 0.3% | 0.3% | 0.4% | 0.3% | 0.3% | 0.3% | 0.3% | 0.3% |
| C18:3w6 γ-linolenic (GLA) | 0.0% | 1.4% | 46.1% | 49.7% | 37.0% | 36.7% | 43.4% | 46.8% | 44.5% |
| C20:1w9 | 0.3% | 0.2% | 0.1% | 0.1% | 0.1% | 0.1% | 0.1% | 0.1% | 0.1% |
| C18:3w3, α-linolenic (ALA) | 0.1% | 0.1% | 0.5% | 0.6% | 0.5% | 0.6% | 0.5% | 0.8% | 0.6% |
| C21:0 Heneicosanoic | 0.1% | 0.1% | 0.1% | 0.1% | 0.1% | 0.1% | 0.0% | 0.0% | 0.1% |
| C20:2w6 Eicosadienoic | 0.0% | 0.0% | 0.1% | 0.1% | 0.1% | 0.1% | 0.1% | 0.1% | 0.1% |
| C22:0 Behenic | 0.2% | 0.2% | 0.2% | 0.3% | 0.2% | 0.1% | 0.2% | 0.2% | 0.1% |
| C20:3w6 Dihomo-γ-linolenic (DGLA) | 0.0% | 0.0% | 0.0% | 0.0% | 0.0% | 0.0% | 0.0% | 0.0% | 0.0% |
| C22:1w9 Erucic | 0.0% | 0.0% | 0.0% | 0.0% | 0.0% | 0.0% | 0.0% | 0.0% | 0.0% |
| C20:3w3 | 0.0% | 0.0% | 0.0% | 0.0% | 0.0% | 0.0% | 0.0% | 0.0% | 0.0% |
| C20:4w6 Arachidonic (AA) | 0.0% | 0.0% | 0.1% | 0.1% | 0.1% | 0.1% | 0.1% | 0.1% | 0.1% |
| C23:0 Tricosanoic | 0.0% | 0.0% | 0.0% | 0.0% | 0.0% | 0.0% | 0.0% | 0.0% | 0.0% |

TABLE 3-continued

|  | Individual Seed Samples of Transgenic Line S1 | | | | | | | | |
|---|---|---|---|---|---|---|---|---|---|
| Fatty Acids | NULL | S1-1 | S1-2 | S1-3 | S1-4 | S1-5 | S1-6 | S1-7 | S1-8 |
| C22:2w6 | 0.0% | 0.1% | 0.1% | 0.1% | 0.0% | 0.0% | 0.0% | 0.0% | 0.0% |
| C24:0 Lignoceric | 0.2% | 0.2% | 0.1% | 0.1% | 0.1% | 0.1% | 0.1% | 0.1% | 0.1% |
| C20:5w3 Eicosapentaenoic (EPA) | 0.0% | 0.0% | 0.1% | 0.1% | 0.1% | 0.1% | 0.1% | 0.1% | 0.1% |
| C24:1w9c | 0.2% | 0.2% | 0.1% | 0.2% | 0.1% | 0.1% | 0.1% | 0.1% | 0.1% |
| C22:6w3 Docosahexaenoic (DHA) | 0.2% | 0.2% | 0.2% | 0.1% | 0.1% | 0.2% | 0.2% | 0.2% | 0.0% |
| Total fatty acids | 100.0% | 100.0% | 100.0% | 100.0% | 100.0% | 100.0% | 100.0% | 100.0% | 100.0% |
| Saturated fatty acids | 9.6% | 9.9% | 13.9% | 13.9% | 11.8% | 13.3% | 13.1% | 11.6% | 12.3% |
| Total W7's & W5's | 0.3% | 0.5% | 0.3% | 0.3% | 0.3% | 0.3% | 0.3% | 0.2% | 0.4% |
| Total W9's | 75.4% | 60.3% | 0.9% | 1.1% | 1.0% | 0.9% | 0.9% | 0.9% | 0.9% |
| Total W6's | 14.1% | 28.8% | 84.1% | 83.7% | 86.0% | 84.6% | 84.9% | 86.3% | 85.7% |
| Total W3's | 0.4% | 0.4% | 0.8% | 0.8% | 0.8% | 0.8% | 0.8% | 1.0% | 0.7% |
| Total monounsaturated fatty acids | 75.7% | 60.7% | 1.2% | 1.4% | 1.3% | 1.1% | 1.2% | 1.1% | 1.3% |
| Total trans fatty acids | 0.1% | 0.2% | 0.0% | 0.2% | 0.0% | 0.1% | 0.0% | 0.0% | 0.0% |
| Polyunsaturated fatty acids | 14.5% | 29.2% | 84.9% | 84.5% | 86.8% | 85.5% | 85.7% | 87.3% | 86.4% |
| Ratios: | | | | | | | | | |
| Polyunsaturated/saturated | 1.5 | 3.0 | 6.1 | 6.1 | 7.3 | 6.4 | 6.6 | 7.5 | 7.0 |
| Omega 6/Omega 3 | 35.3 | 75.7 | 109.0 | 99.3 | 108.2 | 100.1 | 105.3 | 83.6 | 127.4 |
| AA/EPA | 0.4 | 0.4 | 0.6 | 0.5 | 0.4 | 0.7 | 0.7 | 1.2 | 0.6 |
| AA/DHA | 0.1 | 0.1 | 0.3 | 0.5 | 0.3 | 0.3 | 0.3 | 0.4 | 4.2 |

TABLE 4

|  | Individual Seed Samples of Transgenie Line S4 | | | | | | | | | |
|---|---|---|---|---|---|---|---|---|---|---|
| Fatty Acids | NULL | S4-1 | S4-2 | S4-3 | S4-4 | S4-5 | S4-6 | S4-7 | S4-8 | S4-9 |
| C10:0 Capric | 0.6% | 0.7% | 0.7% | 0.6% | 0.5% | 0.8% | 0.4% | 0.5% | 1.0% | 0.6% |
| C11:0 | 0.1% | 0.2% | 0.2% | 0.2% | 0.2% | 0.2% | 0.1% | 0.2% | 0.3% | 0.2% |
| C12:0 Lauric | 0.1% | 0.1% | 0.1% | 0.1% | 0.1% | 0.1% | 0.1% | 0.1% | 0.2% | 0.1% |
| C13:0 Tridecanoic | 0.0% | 0.1% | 0.1% | 0.0% | 0.0% | 0.0% | 0.0% | 0.0% | 0.1% | 0.0% |
| C14:0 Myristic | 0.3% | 0.2% | 0.2% | 0.2% | 0.4% | 0.3% | 0.2% | 0.2% | 0.2% | 0.3% |
| C14:1w5, Myristoleic | 0.1% | 0.2% | 0.1% | 0.0% | 0.0% | 0.1% | 0.1% | 0.1% | 0.1% | 0.0% |
| C15:0 Pentadecanoic | 0.1% | 0.0% | 0.1% | 0.1% | 0.1% | 0.1% | 0.1% | 0.1% | 0.1% | 0.1% |
| C15:1w5cis 10-Pentadecenoid | 0.0% | 0.1% | 0.1% | 0.0% | 0.0% | 0.0% | 0.0% | 0.0% | 0.0% | 0.0% |
| C16:0 Palmitic | 5.8% | 5.4% | 5.3% | 6.0% | 6.4% | 6.5% | 5.2% | 5.5% | 5.7% | 5.9% |
| C16:1w7c Palmitoleic | 0.3% | 0.3% | 0.3% | 0.2% | 0.2% | 0.2% | 0.3% | 0.2% | 0.3% | 0.3% |
| C17:0 Heptadecanoic | 0.2% | 0.1% | 0.1% | 0.2% | 0.2% | 0.2% | 0.2% | 0.2% | 0.1% | 0.2% |
| c17:1w7 | 0.1% | 0.1% | 0.0% | 0.1% | 0.0% | 0.1% | 0.0% | 0.0% | 0.1% | 0.1% |
| C18:0 Stearic | 2.6% | 1.2% | 1.5% | 1.7% | 4.9% | 2.4% | 1.5% | 1.5% | 1.1% | 2.5% |
| C18:1w9t | 0.0% | 0.2% | 0.0% | 0.0% | 0.1% | 0.0% | 0.0% | 0.0% | 0.0% | 0.1% |
| C18:1w9c | 75.0% | 76.8% | 63.0% | 75.4% | 72.2% | 71.0% | 74.5% | 74.7% | 73.7% | 73.6% |
| INTERNAL STANDARD | | | | | | | | | | |
| C18:2w6t | 0.0% | 0.1% | 0.1% | 0.1% | 0.1% | 0.1% | 0.0% | 0.1% | 0.0% | 0.1% |
| C18:2w6c Linoleic (LA) | 12.8% | 6.0% | 12.5% | 4.2% | 3.6% | 7.7% | 5.4% | 4.7% | 7.4% | 4.3% |
| C20:0 Arachidic | 0.3% | 0.3% | 0.3% | 0.4% | 0.4% | 0.4% | 0.3% | 0.4% | 0.3% | 0.4% |
| C18:3w6 γ-linolenic (GLA) | 0.0% | 6.9% | 13.7% | 9.5% | 8.9% | 8.2% | 10.4% | 10.3% | 8.0% | 9.9% |
| C20:1w9 | 0.3% | 0.3% | 0.4% | 0.3% | 0.3% | 0.3% | 0.3% | 0.3% | 0.3% | 0.3% |
| C18:3w3, α-linolenic (ALA) | 0.1% | 0.1% | 0.2% | 0.1% | 0.0% | 0.1% | 0.1% | 0.1% | 0.1% | 0.1% |
| C21:0 Heneicosanoic | 0.1% | 0.1% | 0.1% | 0.1% | 0.1% | 0.1% | 0.0% | 0.1% | 0.1% | 0.0% |
| C20:2w6 Eicosadienoic | 0.0% | 0.0% | 0.0% | 0.0% | 0.1% | 0.1% | 0.0% | 0.0% | 0.1% | 0.1% |
| C22:0 Behenic | 0.2% | 0.2% | 0.3% | 0.2% | 0.2% | 0.3% | 0.2% | 0.3% | 0.3% | 0.3% |
| C20:3w6 Dihomo-γ-linolenic (DGLA) | 0.0% | 0.0% | 0.0% | 0.0% | 0.0% | 0.0% | 0.0% | 0.0% | 0.0% | 0.0% |
| C22:1w9 Erucic | 0.0% | 0.0% | 0.0% | 0.0% | 0.0% | 0.0% | 0.0% | 0.0% | 0.0% | 0.0% |
| C20:3w3 | 0.0% | 0.0% | 0.0% | 0.0% | 0.0% | 0.0% | 0.0% | 0.0% | 0.0% | 0.0% |
| C20:4w6 Arachidonic (AA) | 0.0% | 0.0% | 0.0% | 0.0% | 0.0% | 0.0% | 0.0% | 0.0% | 0.0% | 0.0% |
| C23:0 Tricosanoic | 0.0% | 0.0% | 0.0% | 0.0% | 0.0% | 0.0% | 0.0% | 0.0% | 0.0% | 0.0% |
| C22:2w6 | 0.0% | 0.1% | 0.1% | 0.0% | 0.1% | 0.0% | 0.0% | 0.0% | 0.1% | 0.0% |
| C24:0 Lignoceric | 0.2% | 0.1% | 0.2% | 0.2% | 0.2% | 0.2% | 0.1% | 0.2% | 0.2% | 0.2% |
| C20:5w3 Eicosapentaenoic (EPA) | 0.0% | 0.1% | 0.0% | 0.0% | 0.0% | 0.1% | 0.0% | 0.0% | 0.1% | 0.0% |
| C24:1w9c | 0.2% | 0.2% | 0.3% | 0.2% | 0.1% | 0.2% | 0.2% | 0.2% | 0.2% | 0.2% |
| C22:6w3 Docosahexaenoic (DHA) | 0.2% | 0.0% | 0.1% | 0.2% | 0.4% | 0.2% | 0.1% | 0.1% | 0.0% | 0.2% |
| Total fatty acids | 100.0% | 100.0% | 100.0% | 100.0% | 100.0% | 100.0% | 100.0% | 100.0% | 100.0% | 100.0% |
| Saturated fatty acids | 10.7% | 8.8% | 9.1% | 9.7% | 13.8% | 11.6% | 8.5% | 9.1% | 9.6% | 10.8% |
| Total W7's & W5's | 0.5% | 0.6% | 0.5% | 0.3% | 0.3% | 0.4% | 0.4% | 0.3% | 0.5% | 0.4% |
| Total W9's | 75.5% | 77.2% | 63.7% | 75.9% | 72.6% | 71.5% | 74.9% | 75.2% | 74.2% | 74.1% |
| Total W6's | 12.9% | 13.0% | 26.2% | 13.8% | 12.7% | 16.0% | 15.9% | 15.1% | 15.5% | 14.3% |
| Total W3's | 0.4% | 0.2% | 0.4% | 0.3% | 0.5% | 0.4% | 0.2% | 0.1% | 0.2% | 0.3% |
| Total monounsaturated fatty acids | 75.9% | 77.8% | 64.2% | 76.1% | 72.9% | 71.9% | 75.3% | 75.6% | 74.7% | 74.5% |

TABLE 4-continued

| | Individual Seed Samples of Transgenic Line S4 | | | | | | | | | |
|---|---|---|---|---|---|---|---|---|---|---|
| Fatty Acids | NULL | S4-1 | S4-2 | S4-3 | S4-4 | S4-5 | S4-6 | S4-7 | S4-8 | S4-9 |
| Total trans fatty acids | 0.1% | 0.2% | 0.1% | 0.1% | 0.1% | 0.1% | 0.1% | 0.1% | 0.0% | 0.1% |
| Polyunsaturated fatty acids | 13.3% | 13.1% | 26.6% | 14.0% | 13.1% | 16.4% | 16.1% | 15.2% | 15.7% | 14.5% |
| Ratios: | | | | | | | | | | |
| Polyunsaturated/saturated | 1.2 | 1.5 | 2.9 | 1.4 | 1.0 | 1.4 | 1.9 | 1.7 | 1.6 | 1.3 |
| Omega 6/Omega 3 | 35.3 | 76.9 | 69.1 | 50.9 | 27.1 | 42.6 | 85.3 | 104.7 | 79.0 | 55.2 |
| AA/EPA | 0.3 | 0.3 | 0.3 | 0.5 | 0.6 | 0.3 | 0.5 | 0.1 | 0.1 | 0.1 |
| AA/DHA | 0.1 | 0.4 | 0.1 | 0.1 | 0.0 | 0.1 | 0.1 | 0.0 | 0.2 | 0.0 |

TABLE 5

| | Individual Seed Samples of Transgenic Line S5 | | | | | | | | | |
|---|---|---|---|---|---|---|---|---|---|---|
| Fatty Acids | NULL | S5-1 | S5-2 | S5-3 | S5-4 | S5-5 | S5-6 | S5-7 | S5-8 | S5-9 |
| C10:0 Capric | 0.5% | 0.3% | 2.6% | 0.6% | 0.6% | 0.4% | 0.4% | 0.5% | 0.2% | 0.6% |
| C11:0 | 0.1% | 0.1% | 0.1% | 0.2% | 0.2% | 0.1% | 0.1% | 0.2% | 0.6% | 0.2% |
| C12:0 Lauric | 0.2% | 0.1% | 0.6% | 0.2% | 0.2% | 0.1% | 0.1% | 0.2% | 0.3% | 0.2% |
| C13:0 Tridecanoic | 0.0% | 0.0% | 0.1% | 0.1% | 0.1% | 0.0% | 0.0% | 0.0% | 0.1% | 0.1% |
| C14:0 Myristic | 0.3% | 0.2% | 0.2% | 0.2% | 0.2% | 0.3% | 0.2% | 0.3% | 1.0% | 0.2% |
| C14:1w5, Myristoleic | 0.1% | 0.0% | 0.2% | 0.1% | 0.1% | 0.0% | 0.0% | 0.0% | 0.2% | 0.1% |
| C15:0 Pentadecanoic | 0.1% | 0.1% | 0.3% | 0.1% | 0.1% | 0.1% | 0.1% | 0.1% | 0.3% | 0.1% |
| C15:1w5cis 10-Pentadecenoid | 0.0% | 0.0% | 0.3% | 0.0% | 0.0% | 0.0% | 0.0% | 0.0% | 0.2% | 0.0% |
| C16:0 Palmitic | 5.5% | 7.4% | 8.3% | 6.8% | 7.4% | 7.9% | 7.2% | 7.7% | 12.9% | 8.0% |
| C16:1w7c Palmitoleic | 0.2% | 0.2% | 0.1% | 0.1% | 0.2% | 0.2% | 0.1% | 0.2% | 0.4% | 0.3% |
| C17:0 Heptadecanoic | 0.1% | 0.1% | 0.3% | 0.1% | 0.2% | 0.2% | 0.1% | 0.2% | 0.7% | 0.2% |
| c17:1w7 | 0.1% | 0.0% | 0.0% | 0.0% | 0.0% | 0.0% | 0.0% | 0.0% | 0.0% | 0.1% |
| C18:0 Stearic | 1.6% | 1.7% | 2.8% | 1.6% | 1.6% | 4.4% | 1.5% | 2.2% | 10.5% | 1.5% |
| C18:1w9t | 0.0% | 0.0% | 0.0% | 0.0% | 0.0% | 0.0% | 0.0% | 0.0% | 0.0% | 0.0% |
| C18:1w9c INTERNAL STANDARD | 75.9% | 0.7% | 1.0% | 0.7% | 0.7% | 0.8% | 0.7% | 0.7% | 0.8% | 0.9% |
| C18:2w6t | 0.1% | 0.0% | 0.6% | 0.1% | 0.0% | 0.0% | 0.0% | 0.0% | 0.1% | 0.0% |
| C18:2w6c Linoleic (LA) | 13.5% | 67.2% | 69.9% | 76.5% | 67.2% | 70.9% | 67.1% | 64.7% | 52.0% | 74.2% |
| C20:0 Arachidic | 0.4% | 0.3% | 0.4% | 0.2% | 0.3% | 0.3% | 0.2% | 0.2% | 0.5% | 0.3% |
| C18:3w6 γ-linolenic (GLA) | 0.0% | 20.4% | 10.6% | 11.2% | 19.9% | 12.9% | 21.1% | 21.4% | 16.3% | 11.7% |
| C20:1w9 | 0.2% | 0.1% | 0.1% | 0.1% | 0.1% | 0.1% | 0.0% | 0.1% | 0.0% | 0.1% |
| C18:3w3, α-linolenic (ALA) | 0.1% | 0.2% | 0.2% | 0.2% | 0.2% | 0.1% | 0.2% | 0.2% | 0.7% | 0.3% |
| C21:0 Heneicosanoic | 0.0% | 0.0% | 0.0% | 0.1% | 0.0% | 0.1% | 0.0% | 0.1% | 0.1% | 0.0% |
| C20:2w6 Eicosadienoic | 0.1% | 0.1% | 0.1% | 0.1% | 0.1% | 0.0% | 0.1% | 0.1% | 0.1% | 0.1% |
| C22:0 Behenic | 0.3% | 0.2% | 0.2% | 0.2% | 0.1% | 0.2% | 0.1% | 0.2% | 0.2% | 0.2% |
| C20:3w6 Dihomo-γ-linolenic (DGLA) | 0.0% | 0.0% | 0.0% | 0.0% | 0.0% | 0.0% | 0.0% | 0.0% | 0.0% | 0.0% |
| C22:1w9 Erucic | 0.0% | 0.0% | 0.0% | 0.0% | 0.0% | 0.0% | 0.0% | 0.0% | 0.0% | 0.0% |
| C20:3w3 | 0.0% | 0.0% | 0.0% | 0.0% | 0.0% | 0.0% | 0.0% | 0.0% | 0.0% | 0.0% |
| C20:4w6 Arachidonic (AA) | 0.0% | 0.0% | 0.0% | 0.0% | 0.0% | 0.0% | 0.0% | 0.0% | 0.0% | 0.0% |
| C23:0 Tricosanoic | 0.0% | 0.0% | 0.0% | 0.0% | 0.0% | 0.0% | 0.0% | 0.0% | 0.0% | 0.0% |
| C22:2w6 | 0.0% | 0.0% | 0.2% | 0.1% | 0.0% | 0.0% | 0.0% | 0.1% | 0.1% | 0.0% |
| C24:0 Lignoceric | 0.2% | 0.1% | 0.1% | 0.1% | 0.1% | 0.1% | 0.1% | 0.1% | 0.2% | 0.2% |
| C20:5w3 Eicosapentaenoic (EPA) | 0.0% | 0.1% | 0.2% | 0.1% | 0.1% | 0.0% | 0.0% | 0.0% | 0.1% | 0.1% |
| C24:1w9c | 0.2% | 0.2% | 0.1% | 0.2% | 0.1% | 0.1% | 0.2% | 0.2% | 0.3% | 0.2% |
| C22:6w3 Docosahexaenoic (DHA) | 0.2% | 0.1% | 0.1% | 0.0% | 0.0% | 0.3% | 0.1% | 0.1% | 0.7% | 0.1% |
| Total fatty acids | 100.0% | 100.0% | 100.0% | 100.0% | 100.0% | 100.0% | 100.0% | 100.0% | 100.0% | 100.0% |
| Saturated fatty acids | 9.3% | 10.6% | 16.0% | 10.4% | 11.1% | 14.1% | 10.2% | 12.0% | 27.8% | 11.8% |
| Total W7's & W5's | 0.3% | 0.3% | 0.7% | 0.3% | 0.3% | 0.3% | 0.2% | 0.3% | 0.8% | 0.5% |
| Total W9's | 76.3% | 1.0% | 1.3% | 1.1% | 1.0% | 1.1% | 0.9% | 1.0% | 1.2% | 1.3% |
| Total W6's | 13.6% | 87.7% | 81.0% | 87.9% | 87.2% | 84.0% | 88.3% | 86.3% | 68.6% | 86.0% |
| Total W3's | 0.3% | 0.3% | 0.4% | 0.3% | 0.3% | 0.5% | 0.3% | 0.3% | 1.5% | 0.4% |
| Total monounsaturated fatty acids | 76.7% | 1.3% | 1.9% | 1.3% | 1.3% | 1.4% | 1.1% | 1.3% | 1.9% | 1.7% |
| Total trans fatty acids | 0.1% | 0.0% | 0.6% | 0.1% | 0.1% | 0.0% | 0.0% | 0.1% | 0.1% | 0.1% |
| Polyunsaturated fatty acids | 13.9% | 88.1% | 81.4% | 88.2% | 87.5% | 84.4% | 88.6% | 86.6% | 70.2% | 86.4% |
| Ratios: | | | | | | | | | | |
| Polyunsaturated/saturated | 1.5 | 8.3 | 5.1 | 8.5 | 7.9 | 6.0 | 8.7 | 7.2 | 2.5 | 7.3 |
| Omega 6/Omega 3 | 44.5 | 260.6 | 180.6 | 293.7 | 299.0 | 183.9 | 258.7 | 276.3 | 44.4 | 207.7 |
| AA/EPA | 0.1 | 0.1 | 0.2 | 0.3 | 0.3 | 0.1 | 0.1 | 0.2 | 0.1 | 0.4 |
| AA/DHA | 0.0 | 0.1 | 0.3 | 0.6 | 0.4 | 0.0 | 0.1 | 0.1 | 0.0 | 0.4 |

TABLE 6

| | Individual Seed Samples of Transgenic Line S24 | | | | | | | | | |
|---|---|---|---|---|---|---|---|---|---|---|
| Fatty Acids | S24-1 | S24-2 | S24-3 | S24-4 | S24-5 | S24-6 | S24-7 | S24-8 | S24-9 | S24-10 |
| C10:0 Capric | 0.3% | 0.5% | 0.5% | 0.7% | 0.4% | 0.5% | 0.3% | 0.4% | 0.3% | 0.5% |
| C11:0 | 0.0% | 0.0% | 0.0% | 0.0% | 0.0% | 0.0% | 0.0% | 0.0% | 0.0% | 0.0% |
| C12:0 Lauric | 0.1% | 0.1% | 0.1% | 0.1% | 0.1% | 0.2% | 0.1% | 0.1% | 0.1% | 0.1% |
| C13:0 Tridecanoic | 0.0% | 0.0% | 0.0% | 0.0% | 0.0% | 0.0% | 0.0% | 0.0% | 0.0% | 0.0% |
| C14:0 Myristic | 0.3% | 0.3% | 0.2% | 0.5% | 0.3% | 0.5% | 0.3% | 0.2% | 0.3% | 0.2% |
| C14:1w5, Myristoleic | 0.0% | 0.0% | 0.0% | 0.1% | 0.0% | 0.0% | 0.0% | 0.0% | 0.0% | 0.1% |
| C15:0 Pentadecanoic | 0.1% | 0.1% | 0.0% | 0.1% | 0.1% | 0.1% | 0.1% | 0.1% | 0.0% | 0.1% |
| C15:1w5cis 10-Pentadecenoid | 0.0% | 0.0% | 0.0% | 0.0% | 0.0% | 0.0% | 0.0% | 0.0% | 0.0% | 0.0% |
| C16:0 Palmitic | 7.3% | 6.7% | 7.1% | 8.4% | 8.2% | 9.8% | 7.3% | 6.5% | 7.9% | 5.4% |
| C16:1w7c Palmitoleic | 0.1% | 0.1% | 0.2% | 0.3% | 0.1% | 0.2% | 0.1% | 0.1% | 0.1% | 0.2% |
| C17:0 Heptadecanoic | 0.2% | 0.2% | 0.1% | 0.3% | 0.2% | 0.3% | 0.1% | 0.2% | 0.2% | 0.2% |
| c17:1w7 | 0.0% | 0.0% | 0.1% | 0.0% | 0.1% | 0.0% | 0.1% | 0.1% | 0.5% | 0.5% |
| C18:0 Stearic | 3.0% | 2.7% | 2.9% | 4.9% | 3.9% | 5.3% | 3.4% | 1.7% | 3.6% | 2.1% |
| C18:1w9t | 0.0% | 0.0% | 0.0% | 0.0% | 0.0% | 0.0% | 0.0% | 0.0% | 0.0% | 0.0% |
| C18:1w9c INTERNAL STANDARD | 3.7% | 4.2% | 4.7% | 2.5% | 3.7% | 2.0% | 5.3% | 3.3% | 3.4% | 73.9% |
| C18:2w6t | 0.0% | 0.0% | 0.0% | 0.1% | 0.0% | 0.1% | 0.1% | 0.1% | 0.1% | 0.1% |
| C18:2w6c Linoleic (LA) | 50.8% | 53.1% | 57.3% | 35.3% | 47.1% | 35.6% | 51.8% | 54.9% | 50.0% | 8.4% |
| C20:0 Arachidic | 0.2% | 0.2% | 0.2% | 0.3% | 0.3% | 0.3% | 0.3% | 0.2% | 0.2% | 0.3% |
| C18:3w6 γ-linolenic (GLA) | 32.1% | 30.4% | 25.3% | 43.7% | 34.0% | 43.3% | 29.3% | 30.7% | 31.7% | 6.4% |
| C20:1w9 | 0.1% | 0.1% | 0.1% | 0.1% | 0.1% | 0.1% | 0.1% | 0.1% | 0.1% | 0.3% |
| C18:3w3, α-linolenic (ALA) | 0.3% | 0.3% | 0.3% | 0.5% | 0.3% | 0.5% | 0.3% | 0.4% | 0.4% | 0.1% |
| C21:0 Heneicosanoic | 0.1% | 0.1% | 0.1% | 0.2% | 0.1% | 0.1% | 0.1% | 0.1% | 0.1% | 0.1% |
| C20:2w6 Eicosadienoic | 0.1% | 0.1% | 0.1% | 0.2% | 0.1% | 0.1% | 0.1% | 0.1% | 0.1% | 0.1% |
| C22:0 Behenic | 0.2% | 0.2% | 0.1% | 0.3% | 0.2% | 0.2% | 0.2% | 0.1% | 0.1% | 0.3% |
| C20:3w6 Dihomo-γ-linolenic (DGLA) | 0.0% | 0.0% | 0.0% | 0.1% | 0.0% | 0.0% | 0.0% | 0.0% | 0.0% | 0.0% |
| C22:1w9 Erucic | 0.0% | 0.0% | 0.0% | 0.1% | 0.0% | 0.0% | 0.0% | 0.0% | 0.0% | 0.0% |
| C20:3w3 | 0.0% | 0.0% | 0.0% | 0.0% | 0.0% | 0.0% | 0.0% | 0.0% | 0.0% | 0.0% |
| C20:4w6 Arachidonic (AA) | 0.1% | 0.0% | 0.0% | 0.1% | 0.0% | 0.1% | 0.0% | 0.0% | 0.0% | 0.0% |
| C23:0 Tricosanoic | 0.0% | 0.0% | 0.0% | 0.1% | 0.0% | 0.0% | 0.0% | 0.0% | 0.0% | 0.0% |
| C22:2w6 | 0.1% | 0.0% | 0.0% | 0.1% | 0.0% | 0.1% | 0.0% | 0.0% | 0.0% | 0.0% |
| C24:0 Lignoceric | 0.1% | 0.1% | 0.1% | 0.2% | 0.1% | 0.1% | 0.1% | 0.1% | 0.1% | 0.2% |
| C20:5w3 Eicosapentaenoic (EPA) | 0.1% | 0.1% | 0.1% | 0.1% | 0.1% | 0.1% | 0.1% | 0.1% | 0.1% | 0.0% |
| C24:1w9c | 0.1% | 0.1% | 0.1% | 0.3% | 0.1% | 0.2% | 0.2% | 0.1% | 0.2% | 0.2% |
| C22:6w3 Docosahexaenoic (DHA) | 0.3% | 0.1% | 0.2% | 0.4% | 0.2% | 0.2% | 0.2% | 0.0% | 0.2% | 0.3% |
| Total fatty acids | 100.0% | 100.0% | 100.0% | 100.0% | 100.0% | 100.0% | 100.0% | 100.0% | 100.0% | 100.0% |
| Saturated fatty acids | 11.9% | 11.1% | 11.5% | 16.0% | 13.9% | 17.5% | 12.1% | 9.7% | 13.0% | 9.5% |
| Total W7's & W5's | 0.1% | 0.2% | 0.2% | 0.4% | 0.3% | 0.2% | 0.3% | 0.2% | 0.6% | 0.8% |
| Total W9's | 4.0% | 4.5% | 4.9% | 3.0% | 4.0% | 2.2% | 5.6% | 3.6% | 3.6% | 74.3% |
| Total W6's | 83.2% | 83.7% | 82.8% | 79.4% | 81.2% | 79.2% | 81.3% | 85.8% | 81.9% | 14.9% |
| Total W3's | 0.7% | 0.5% | 0.5% | 1.1% | 0.6% | 0.8% | 0.5% | 0.6% | 0.7% | 0.4% |
| Total monounsaturated fatty acids | 4.2% | 4.6% | 5.2% | 3.4% | 4.2% | 2.5% | 6.0% | 3.8% | 4.3% | 75.1% |
| Total trans fatty acids | 0.1% | 0.1% | 0.1% | 0.1% | 0.1% | 0.1% | 0.1% | 0.1% | 0.1% | 0.1% |
| Polyunsaturated fatty acids | 83.9% | 84.2% | 83.3% | 80.5% | 81.9% | 79.9% | 81.8% | 86.4% | 82.6% | 15.3% |
| Ratios: | | | | | | | | | | |
| Polyunsaturated/saturated | 7.1 | 7.6 | 7.2 | 5.0 | 5.9 | 4.6 | 6.7 | 8.9 | 6.4 | 1.6 |
| Omega 6/Omega 3 | 111.6 | 162.9 | 162.1 | 73.1 | 128.9 | 102.1 | 169.0 | 149.7 | 112.7 | 37.8 |
| AA/EPA | 0.5 | 0.4 | 0.6 | 0.6 | 0.7 | 1.0 | 0.7 | 0.4 | 0.4 | 0.3 |
| AA/DHA | 0.2 | 0.2 | 0.2 | 0.2 | 0.2 | 0.2 | 0.3 | 0.8 | 0.2 | 0.0 |

TABLE 7

| | Individual Seed Samples of Transgenie Line S27 | | | | | | | | |
|---|---|---|---|---|---|---|---|---|---|
| | NULL | S27-1 | S27-2 | S27-3 | S27-4 | S27-5 | S27-6 | S27-7 | S27-8 |
| C10:0 Capric | 0.6% | 0.6% | 0.4% | 0.4% | 0.6% | 0.4% | 0.5% | 0.3% | 0.4% |
| C11:0 | 0.0% | 0.0% | 0.0% | 0.0% | 0.0% | 0.0% | 0.0% | 0.0% | 0.0% |
| C12:0 Lauric | 0.2% | 0.2% | 0.1% | 0.1% | 0.1% | 0.1% | 0.1% | 0.1% | 0.1% |
| C13:0 Tridecanoic | 0.1% | 0.0% | 0.0% | 0.1% | 0.1% | 0.0% | 0.1% | 0.0% | 0.0% |
| C14:0 Myristic | 0.4% | 0.4% | 0.3% | 0.3% | 0.4% | 0.2% | 0.3% | 0.3% | 0.3% |
| C14:1w5, Myristoleic | 0.1% | 0.1% | 0.1% | 0.1% | 0.1% | 0.0% | 0.2% | 0.1% | 0.1% |
| C15:0 Pentadecanoic | 0.1% | 0.1% | 0.1% | 0.1% | 0.1% | 0.1% | 0.1% | 0.1% | 0.1% |
| C15:1w5cis 10-Pentadecenoid | 0.0% | 0.0% | 0.0% | 0.0% | 0.0% | 0.0% | 0.0% | 0.0% | 0.0% |
| C16:0 Palmitic | 7.4% | 8.0% | 8.7% | 10.6% | 8.6% | 7.6% | 9.0% | 8.9% | 8.1% |
| C16:1w7c Palmitoleic | 0.3% | 0.3% | 0.2% | 0.2% | 0.2% | 0.1% | 0.2% | 0.2% | 0.2% |
| C17:0 Heptadecanoic | 0.3% | 0.2% | 0.2% | 0.2% | 0.2% | 0.2% | 0.1% | 0.1% | 0.3% |
| c17:1w7 | 0.0% | 0.0% | 0.0% | 0.0% | 0.4% | 0.4% | 0.6% | 0.3% | 0.1% |
| C18:0 Stearic | 5.0% | 3.6% | 3.6% | 3.7% | 5.1% | 3.0% | 4.1% | 2.7% | 3.7% |

TABLE 7-continued

| | Individual Seed Samples of Transgenic Line S27 | | | | | | | | |
|---|---|---|---|---|---|---|---|---|---|
| | NULL | S27-1 | S27-2 | S27-3 | S27-4 | S27-5 | S27-6 | S27-7 | S27-8 |
| C18:1w9t | 0.0% | 0.0% | 0.0% | 0.0% | 0.0% | 0.0% | 0.0% | 0.0% | 0.0% |
| C18:1w9c | 66.9% | 2.8% | 1.8% | 3.2% | 3.4% | 3.7% | 3.4% | 1.6% | 3.4% |
| INTERNAL STANDARD | | | | | | | | | |
| C18:2w6t | 0.1% | 0.1% | 0.0% | 0.0% | 0.1% | 0.0% | 0.0% | 0.0% | 0.2% |
| C18:2w6c Linoleic (LA) | 16.2% | 46.6% | 31.5% | 48.8% | 45.4% | 55.7% | 50.8% | 35.7% | 53.3% |
| C20:0 Arachidic | 0.5% | 0.3% | 0.4% | 0.5% | 0.4% | 0.2% | 0.5% | 0.3% | 0.3% |
| C18:3w6 γ-linolenic (GLA) | 0.0% | 34.4% | 50.7% | 29.8% | 33.1% | 26.8% | 28.1% | 47.7% | 27.8% |
| C20:1w9 | 0.3% | 0.1% | 0.1% | 0.1% | 0.1% | 0.1% | 0.1% | 0.1% | 0.1% |
| C18:3w3, α-linolenic (ALA) | 0.2% | 0.6% | 0.6% | 0.5% | 0.5% | 0.5% | 0.7% | 0.7% | 0.4% |
| C21:0 Heneicosanoic | 0.1% | 0.1% | 0.1% | 0.1% | 0.1% | 0.0% | 0.1% | 0.1% | 0.1% |
| C20:2w6 Eicosadienoic | 0.1% | 0.1% | 0.1% | 0.1% | 0.1% | 0.1% | 0.1% | 0.1% | 0.1% |
| C22:0 Behenic | 0.2% | 0.2% | 0.2% | 0.3% | 0.2% | 0.1% | 0.2% | 0.2% | 0.2% |
| C20:3w6 Dihomo-γ-linolenic (DGLA) | 0.0% | 0.0% | 0.0% | 0.0% | 0.0% | 0.0% | 0.0% | 0.0% | 0.0% |
| C22:1w9 Erucic | 0.0% | 0.0% | 0.0% | 0.0% | 0.0% | 0.0% | 0.0% | 0.0% | 0.0% |
| C20:3w3 | 0.0% | 0.0% | 0.0% | 0.0% | 0.0% | 0.0% | 0.0% | 0.0% | 0.0% |
| C20:4w6 Arachidonic (AA) | 0.0% | 0.0% | 0.1% | 0.0% | 0.1% | 0.1% | 0.0% | 0.1% | 0.1% |
| C23:0 Tricosanoic | 0.0% | 0.0% | 0.0% | 0.0% | 0.0% | 0.0% | 0.0% | 0.0% | 0.0% |
| C22:2w6 | 0.0% | 0.1% | 0.0% | 0.0% | 0.0% | 0.0% | 0.0% | 0.0% | 0.0% |
| C24:0 Lignoceric | 0.2% | 0.2% | 0.1% | 0.3% | 0.1% | 0.1% | 0.2% | 0.1% | 0.1% |
| C20:5w3 Eicosapentaenoic (EPA) | 0.1% | 0.1% | 0.1% | 0.1% | 0.1% | 0.0% | 0.1% | 0.1% | 0.1% |
| C24:1w9c | 0.3% | 0.2% | 0.1% | 0.2% | 0.1% | 0.1% | 0.2% | 0.1% | 0.2% |
| C22:6w3 Docosahexaenoic (DHA) | 0.3% | 0.3% | 0.1% | 0.3% | 0.4% | 0.1% | 0.0% | 0.0% | 0.3% |
| Total Fatty acids | 100.0% | 100.0% | 100.0% | 100.0% | 100.0% | 100.0% | 100.0% | 100.0% | 100.0% |
| Saturated Fatty acids | 15.1% | 14.0% | 14.4% | 16.6% | 15.9% | 12.2% | 15.4% | 13.2% | 13.7% |
| Total W7's & W5's | 0.4% | 0.5% | 0.3% | 0.3% | 0.7% | 0.6% | 1.0% | 0.5% | 0.3% |
| Total W9's | 67.4% | 3.1% | 2.1% | 3.4% | 3.6% | 3.9% | 3.7% | 1.8% | 3.7% |
| Total W6's | 16.4% | 81.2% | 82.5% | 78.8% | 78.7% | 82.7% | 79.0% | 83.6% | 81.3% |
| Total W3's | 0.6% | 1.0% | 0.7% | 0.8% | 0.9% | 0.6% | 0.8% | 0.8% | 0.8% |
| Total Monounsaturated Fatty acids | 67.9% | 3.6% | 2.4% | 3.7% | 4.3% | 4.5% | 4.7% | 2.3% | 4.0% |
| Total Trans Fatty Acids | 0.1% | 0.1% | 0.1% | 0.0% | 0.1% | 0.0% | 0.1% | 0.1% | 0.2% |
| Polyunsaturated Fatty acids | 17.0% | 82.2% | 83.2% | 79.6% | 79.6% | 83.3% | 79.8% | 84.4% | 82.1% |
| Ratios: | | | | | | | | | |
| Polyunsaturated/Saturated | 1.1 | 5.9 | 5.8 | 4.8 | 5.0 | 6.8 | 5.2 | 6.4 | 6.0 |
| Omega 6/Omega 3 | 29.3 | 78.7 | 113.9 | 95.8 | 83.3 | 139.2 | 102.0 | 109.9 | 107.0 |
| AA/EPA | 0.3 | 0.3 | 1.1 | 0.5 | 0.9 | 1.2 | 0.6 | 1.0 | 1.0 |
| AA/DHA | 0.1 | 0.1 | 0.8 | 0.2 | 0.1 | 0.7 | 2.6 | 1.3 | 0.2 |

The single seed data follow the trend seen in the pooled seed data. Since T1 lines are still segregating, some variability can be present in single seed samples due to null, heterozygous and homozygous insertions. Observed are GLA concentrations ranging from 1.4% (Table 3: seed 1 in line 1, S1-1) to 50.8% (Table 7: seed 2 line 27, S27-2). Lines with seed oil profiles similar to those from either the single seed data or pooled seed data may be obtained. Certain lines did not set seed. Those that set seed were selected for the study.

Fatty acid composition of seed from T1 and T2 generations of lines expressing the pSBS4766 construct is shown below in Table 8.

TABLE 8

Examples of single seed fatty acid composition (expressed as percentages) in T1 and T2 individual lines of pSBS4766 construct expressed in S317

| Table 8 Line Number | Generation: | C18:3n6 (gamma Linolenic) | C16:0 (Palmitic) | C18:0 (Stearic) | C18:1n9 (Oleic) | C18:2n6 (Linoleic) |
|---|---|---|---|---|---|---|
| 4766-12-4 | T1 | 25.60 | 6.78 | 1.90 | 5.38 | 59.12 |
| 4766-12-4-6 | T2 | 23.38 | 8.54 | 3.57 | 7.66 | 56.27 |
| 4766-21-25 | T1 | 26.10 | 7.83 | 1.91 | 5.36 | 58.53 |
| 4766-21-25-2 | T2 | 24.41 | 8.45 | 3.56 | 9.92 | 53.67 |
| 4766-21-10 | T1 | 15.35 | 7.15 | 1.71 | 9.37 | 65.53 |
| 4766-21-10-7 | T2 | 25.31 | 7.00 | 2.73 | 7.94 | 55.17 |
| 4766-70-43 | T1 | 17.68 | 4.87 | 2.05 | 10.88 | 64.52 |
| 4766-70-43-9 | T2 | 16.75 | 4.80 | 2.33 | 10.58 | 64.80 |
| 4766-110-10 | T1 | 23.37 | 6.65 | 2.00 | 5.77 | 61.26 |
| 4766-110-10-25 | T2 | 29.84 | 8.27 | 3.66 | 6.51 | 50.59 |
| 4766-110-11 | T1 | 19.65 | 6.66 | 2.06 | 7.48 | 63.85 |
| 4766-110-11-32 | T2 | 29.89 | 8.43 | 2.25 | 5.11 | 52.26 |
| 4766-95-4 | T1 | 10.22 | 6.20 | 2.00 | 15.52 | 65.06 |
| 4766-95-4-1 | T2 | 18.05 | 6.72 | 2.24 | 11.13 | 61.12 |
| S317 | VAR | 0.00 | 5.29 | 2.72 | 74.81 | 16.10 |
| S317 | VAR | 0.00 | 5.44 | 1.64 | 74.61 | 17.82 |

Fatty acid composition of T2 seed is consistent with that measured in T1 seed. These data show that the transgene is stable and heritable, producing consistent elevations in GLA across generations.

Example 2

Plasmid pSBS4119 and Transgenic Plants Expressing this Plasmid

Figure 9:
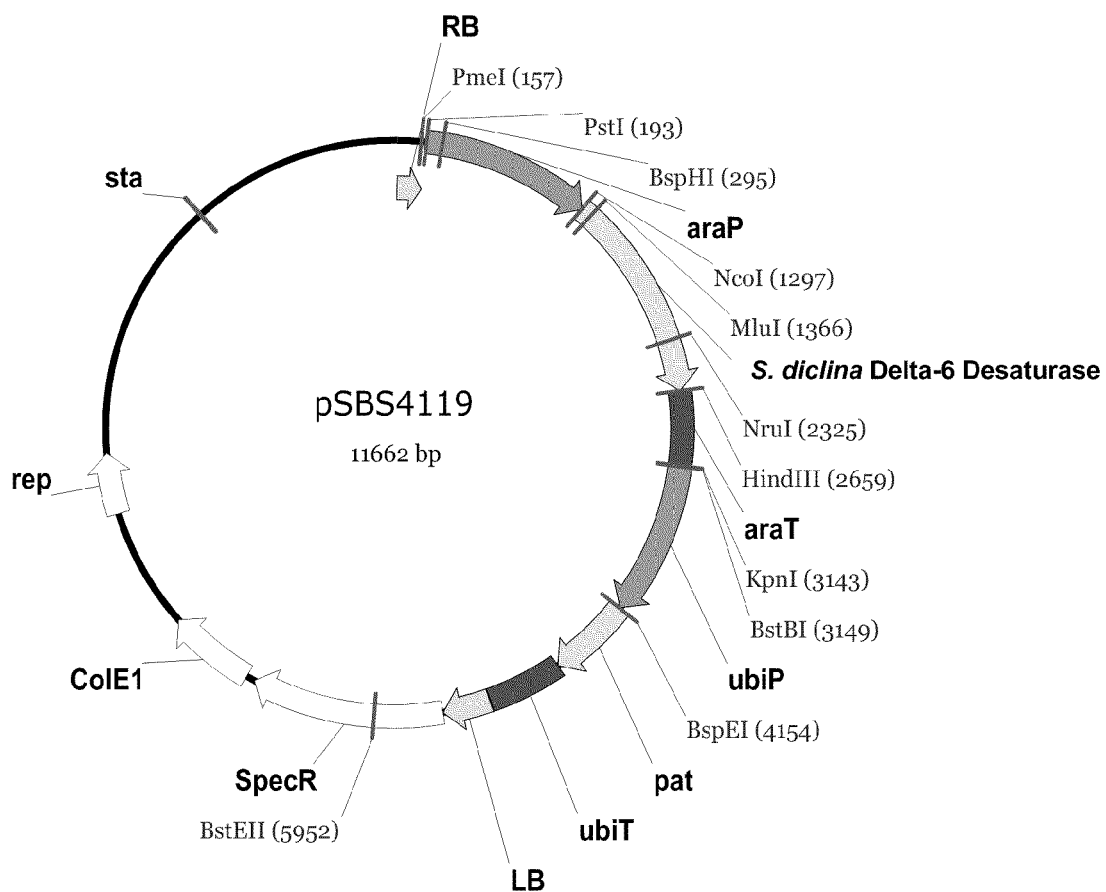
FIG. 9 shows plasmid pSBS4119 for the expression of Δ6-desaturase from the organism *S. diclina*. Shown are various features of the expression construct including promoters, termination sequences and resistance and marker genes. The plant selectable marker on this plasmid is pat, the phosphinothricin acetyl transferase from *Streptomyces viridochromogenes*. The bacterial marker is SpecR.

FIG. 9 shows the map of a construct used to express the Δ6-desaturase from *Saprolegnia Diclina*. The plant selectable marker used in this construct was pat which corresponds to the phosphinothricin acetyl transferase gene from *Streptomyces viridochromogenes*. The bacterial marker used in this construct was SpecR. The base binary vector used to construct this vector is a derivative of pPZP200. See Hajdukiewicz et al., Plant Mol Biol 25: 989, 1994. The sequence of the insert contained within the borders of the pPZP200 plasmid is shown below.

pSBS4119 (*S. diclina* Δ6-desaturase expression cassette with PAT selection) (SEQ ID NO: 2)

```
ctgcaggaattcgatctctattgattcaaattacgatctgatactgataa
cgtctagattttaggggttaaagcaatcaatcacctgacgattcaaggtg
gttggatcatgacgattccagaaaacatcaagcaagctctcaaagctaca
ctctttgggatcatactgaactctaacaacctcgttatgtcccgtagtgc
cagtacagacatcctcgtaactcggattgtgcacgatgccatgactatac
ccaacctcggtcttggtcacaccaggaactctctggtaagctagctccac
tccccagaaacaaccggcgccaaattgcgcgaattgctgacctgaagacg
gaacatcatcgtcgggtccttgggcgattgcggcggaagatgggtcagct
tgggcttgaggacgagacccgaatccgagtctgttgaaaaggttgttcat
tggggatttgtatacggagattggtcgtcgagaggtttgagggaaaggac
aaatgggtttggctctggagaaagagagtgcggctttagagagagaattg
agaggtttagagagagatgcggcggcgatgagcggaggagagacgacgag
gacctgcattatcaaagcagtgacgtggtgaaatttggaacttttaagag
gcagatagatttattatttgtatccattttcttcattgttctagaatgtc
gcggaacaaattttaaaactaaatcctaaattttttctaattttgttgcca
atagtggatatgtgggccgtatagaaggaatctattgaaggcccaaaccc
atactgacgagcccaaaggttcgttttgcgttttatgtttcggttcgatg
ccaacgccacattctgagctaggcaaaaaacaaacgtgtctttgaataga
ctcctctcgttaacacatgcagcggctgcatggtgacgccattaacacgt
ggcctacaattgcatgatgtctccattgacacgtgacttctcgtctcctt
tcttaatatatctaacaaacactcctacctcttccaaaatatatacacat
cttttgatcaatctctcattcaaaatctcattctctctagtaaacaaga
acaaaaaccatggtccaggggcaaaaggccgagaagatctcgtgggcga
ccatccgtgagcacaaccgccaagacaacgcgtggatcgtgatccaccac
aaggtgtacgacatctcggcctttgaggaccaccgggcggcgtcgtcat
gttcacgcaggccggcgaagacgcgaccgatgcgttcgctgtatccaccc
```

-continued

```
gagctcggcgctcaagctcctcgagcagtactacgtcggcgacgtcgacc
agtcgacggcggccgtcgacacgtcgatctcggacgaggtcaagaagagc
cagtcggacttcattgcgtcgtaccgcaagctgcgccttgaagtcaagcg
cctcggcttgtacgactcgagcaagctctactacctctacaagtgcgcct
cgacgctgagcattgcgcttgtgtcggcggccatttgcctccactttgac
tcgacggccatgtacatggtcgcggctgtcatccttggcctcttttacca
gcagtgcggctggctcgcccatgactttctgcaccaccaagtgtttgaga
accacttgtttggcgacctcgtcggcgtcatggtcggcaacctctggcag
ggcttctcggtgcagtggtggaagaacaagcacaacacgcaccatgcgat
ccccaacctccacgcgacgcccgagatcgccttccacgcgacccggaca
ttgacacgatgccgattctcgcgtggtcgctcaagatggcgcagcacgcg
gtcgactcgcccgtcgggctcttcttcatgcgctaccaagcgtacctgta
ctttcccatcttgctctttgcgcgtatctcgtgggtgatccagtcggcca
tgtacgccttctacaacgttgggcccggcggcacctttgacaaggtccag
tacccgctgctcgagcgcgccggcctcctcctctactacggctggaacct
cggccttgtgtacgcagccaacatgtcgctgctccaagcggctgcgttcc
tctttgtgagccaggcgtcgtgcggcctcttcctcgcgatggtctttagc
gtcggccacaacggcatggaggtctttgacaaggacagcaagcccgattt
ttggaagctgcaagtgctctcgacgcgcaacgtgacgtcgtcgctctgga
tcgactggttcatgggcggcctcaactaccagatcgaccaccacttgttc
ccgatggtgccccggcacaacctcccggcgctcaacgtgctcgtcaagtc
gctctgcaagcagtacgacatcccataccacgagacgggcttcatcgcgg
gcatggccgaggtcgtcgtgcacctcgagcgcatctcgatcgagttcttc
aaggagtttcccgccatgtaagcttgttaccccactgatgtcatcgtcat
agtccaataactccaatgtcggggagttagtttatgaggaataaagtgtt
tagaatttgatcaggggggagataataaaagccgagtttgaatcttttttgt
tataagtaatgtttatgtgtgtttctatatgttgtcaaatggtcccatgt
ttttcttcctctatttttgtaacttgcaagtgttgtgttgtactttatttg
gcttctttgtaagttggtaacggtggtctatatatggaaaaggtcttgtt
ttgttaaacttatgttagttaactggattcgtctttaaccacaaaaagtt
ttcaataagctacaaatttagacacgcaagccgatgcagtcattagtaca
tatatttattgcaagtgattacatggcaacccaaacttcaaaaacagtag
gttgctccatttagtaacctgaattgcctcctgattctagttgatcccgg
taccgaattcgaatccaaaaattacggatatgaatataggcatatccgta
tccgaattatccgtttgacagctagcaacgattgtacaattgcttcttta
aaaaaggaagaaagaaagaaagaaaagaatcaacatcagcgttaacaaac
ggccccgttacggcccaaacggtcatatagagtaacggcgttaagcgttg
aaagactcctatcgaaatacgtaaccgcaaacgtgtcatagtcagatccc
ctcttccttcaccgcctcaaacacaaaaataatcttctacagcctatata
tacaaccccccttctatctctccttctcacaattcatcatctttcttt
ctctaccccaattttaagaaatcctctcttctcctcttcattttcaagg
```

-continued

```
taaatctctctctctctctctctctgttattccttgttttaattaggt
atgtattattgctagtttgttaatctgcttatcttatgtatgccttatgt
gaatatctttatcttgttcatctcatccgtttagaagctataaatttgtt
gatttgactgtgtatctacacgtggttatgtttatatctaatcagatatg
aatttcttcatattgttgcgtttgtgtgtaccaatccgaaatcgttgatt
tttttcatttaatcgtgtagctaattgtacgtatacatatggatctacgt
atcaattgttcatctgtttgtgtttgtatgtatacagatctgaaaacatc
acttctctcatctgattgtgttgttacatacatagatatagatctgttat
atcatttttttattaattgtgtatatatatatgtgcatagatctggatta
catgattgtgattatttacatgattttgttatttacgtatgtatatatgt
agatctggacttttttggagttgttgacttgattgtatttgtgtgtgtata
tgtgtgttctgatcttgatatgttatgtatgtgcagccaaggctacgggc
gatccaccatgtctccggagaggagaccagttgagattaggccagctaca
gcagctgatatggccgcggtttgtgatatcgttaaccattacattgagac
gtctacagtgaactttaggacagagccacaaacaccacaagagtggattg
atgatctagagaggttgcaagatagatacccttggttggttgctgaggtt
gagggtgttgtggctggtattgcttacgctgggccctggaaggctaggaa
cgcttacgattggacagttgagagtactgtttacgtgtcacataggcatc
aaaggttgggcctaggttccacattgtacacacatttgcttaagtctatg
gaggcgcaaggttttaagtctgtggttgctgttataggccttccaaacga
tccatctgttaggttgcatgaggctttgggatacacagcccggggtacat
tgcgcgcagctggatacaagcatggtggatggcatgatgttggttttgg
caaagggatttttgagttgccagctcctccaaggccagttaggccagttac
ccagatctgagtcgaccgaatgagttccaagatggtttgtgacgaagtta
gttggttgttttatggaactttgtttaagctagcttgtaatgtggaaag
aacgtgtggctttgtggttttttaaatgttggtgaataaagatgtttcctt
tggattaactagtattttcctattggtttcatggttttagcacacaaca
ttttaaatatgctgttagatgatatgctgcctgctttattatttacttac
ccctcaccttcagtttcaaagttgttgcaatgactctgtgtagtttaaga
tcgagtgaaagtagattttgtctatattattaggggtatttgatatgct
aatggtaaacatggtttatgacagcgtacttttttggttatggtgttgac
gtttccttttaaacattatagtagcgtccttggtctgtgttcattggttg
aacaaaggcacactcacttggagatgccgtctccactgatatttgaacaa
a
```

Transformation of safflower with this construct was performed by SemBioSys Genetics Inc. (Calgary, Canada). Techniques utilized by SemBioSys Genetics Inc. include those described in WO 2004/111244, which is hereby incorporated by reference in its entirety. Transgenic plants will be grown and seed will be harvested.

Seeds were collected from transgenic plants and fatty acid composition was performed using a modification of a gas chromatographic method described in "Official Methods and Recommended Practices of the AOCS", 5th Ed., Method Ce 1-62, American Oil Chemists Society: Champaign, Ill. (1997).

As shown below in Table 9, GLA levels ranged from 11.41% (line 4119-23-1) to 72.89% (line 4119-21-3) in T1 seed from transgenic lines expressing Δ6-desaturase from *S. diclina* in the pSBS4119 construct. GLA levels over 60% were obtained in several transgenic lines. Since T1 lines are still segregating, measurements of single seed samples can vary due to null, heterozygous or homozygous insertions. GLA levels in Centennial controls and Null control lines were not detectable. The Centennial variety is naturally high in LA and transgenic expression of Δ6-desaturase alone is sufficient to increase GLA levels.

TABLE 9

Examples of single seed fatty acid composition (expressed as percentages) in T1 seed of pSBS4119 construct expressed in Centennial

| Table 9 Line Number | Type | C18:3n6 (gamma Linolenic) | C16:0 (Palmitic) | C18:0 (Stearic) | C18:1n9 (Oleic) | C18:2n6 (Linoleic) |
|---|---|---|---|---|---|---|
| 4119-13-1 | Transgenic | 46.47 | 7.11 | 1.55 | 7.98 | 35.87 |
| 4119-13-11 | Transgenic | 51.73 | 7.07 | 1.57 | 6.66 | 32.00 |
| 4119-15-10 | Transgenic | 61.93 | 8.02 | 1.69 | 6.38 | 19.68 |
| 4119-15-7 | Transgenic | 69.59 | 8.03 | 1.43 | 5.70 | 13.33 |
| 4119-17-1 | Transgenic | 69.13 | 9.58 | 1.35 | 5.37 | 12.06 |
| 4119-17-3 | Transgenic | 67.13 | 9.33 | 1.54 | 6.76 | 12.29 |
| 4119-19-1 | NULL | 0.00 | 6.54 | 1.35 | 10.23 | 80.86 |
| 4119-19-10 | Transgenic | 69.85 | 8.13 | 1.35 | 5.42 | 13.70 |
| 4119-20-10 | Transgenic | 63.22 | 7.69 | 1.53 | 5.88 | 20.24 |
| 4119-21-1 | Transgenic | 71.06 | 8.94 | 1.43 | 5.02 | 11.44 |
| 4119-21-3 | Transgenic | 72.89 | 9.68 | 1.21 | 4.12 | 8.59 |
| 4119-2-29 | Transgenic | 52.33 | 7.46 | 1.59 | 7.00 | 30.46 |
| 4119-2-31 | Transgenic | 61.23 | 8.52 | 1.48 | 7.38 | 19.40 |
| 4119-23-1 | Transgenic | 11.41 | 6.34 | 1.41 | 9.28 | 71.57 |
| 4119-23-2 | Transgenic | 11.99 | 6.51 | 1.48 | 9.07 | 70.95 |
| 4119-24-1 | NULL | 0.00 | 6.62 | 1.35 | 10.12 | 80.69 |
| 4119-24-2 | Transgenic | 65.39 | 8.04 | 1.46 | 6.47 | 16.90 |
| 4119-29-2 | Transgenic | 62.91 | 7.68 | 1.30 | 6.82 | 19.44 |
| 4119-29-4 | Transgenic | 62.72 | 7.42 | 1.31 | 6.95 | 19.74 |
| 4119-30-1 | Transgenic | 66.46 | 7.75 | 1.41 | 6.53 | 16.16 |
| 4119-30-10 | Transgenic | 28.28 | 5.97 | 1.59 | 6.46 | 56.93 |

TABLE 9-continued

Examples of single seed fatty acid composition (expressed as percentages) in T1 seed of pSBS4119 construct expressed in Centennial

| Table 9 Line Number | Type | C18:3n6 (gamma Linolenic) | C16:0 (Palmitic) | C18:0 (Stearic) | C18:1n9 (Oleic) | C18:2n6 (Linoleic) |
|---|---|---|---|---|---|---|
| 4119-33-15 | Transgenic | 72.85 | 8.33 | 1.32 | 4.92 | 10.17 |
| 4119-33-18 | Transgenic | 69.73 | 7.53 | 1.33 | 5.90 | 13.29 |
| 4119-35-1 | Transgenic | 59.55 | 7.63 | 1.56 | 10.82 | 17.91 |
| 4119-35-3 | Transgenic | 63.11 | 7.27 | 1.29 | 5.93 | 20.63 |
| 4119-36-14 | Transgenic | 64.90 | 8.19 | 1.41 | 5.85 | 17.98 |
| 4119-36-15 | Transgenic | 61.10 | 8.30 | 1.39 | 8.22 | 19.07 |
| 4119-39-17 | Transgenic | 63.54 | 7.72 | 1.65 | 5.79 | 19.38 |
| 4119-39-18 | Transgenic | 64.79 | 7.66 | 1.57 | 5.11 | 18.68 |
| Centennial-4 | Control | 0.00 | 6.63 | 2.22 | 25.36 | 65.80 |
| Centennial-6 | Control | 0.00 | 6.59 | 2.03 | 13.53 | 76.87 |

Example 3

Plasmid pSBS4763 and Transgenic Plants Expressing this Plasmid

Figure 10:
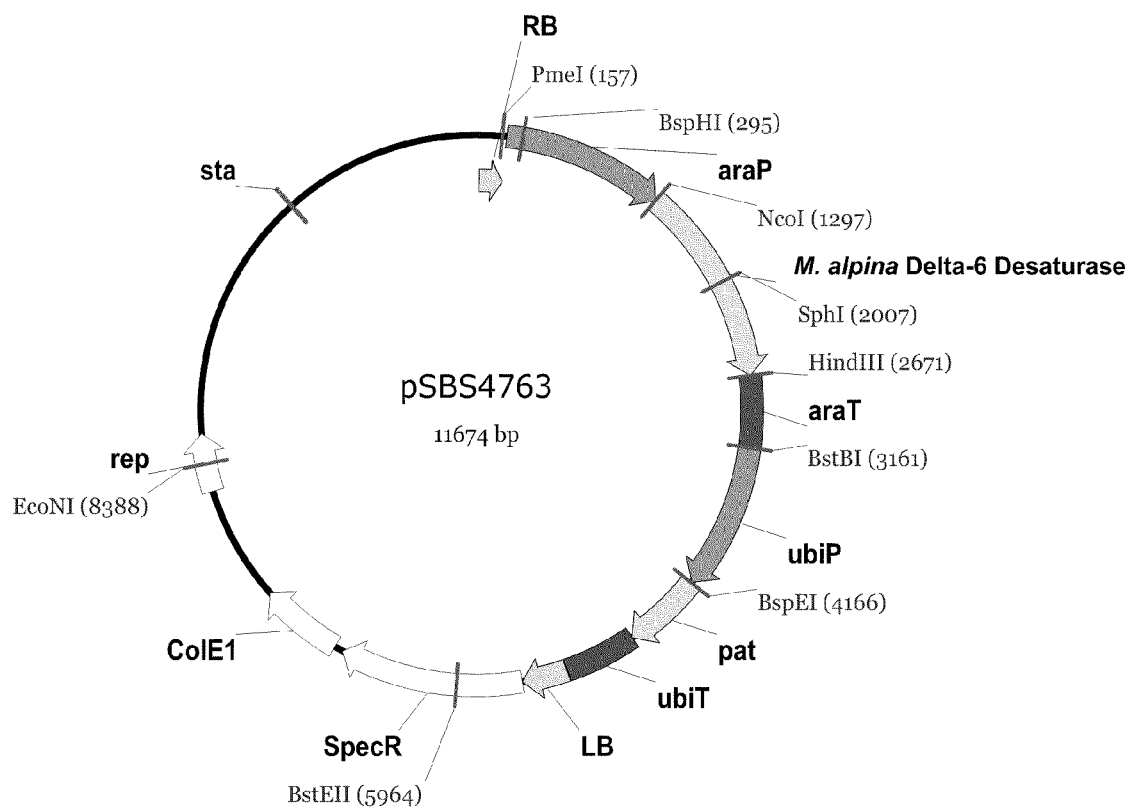
FIG. 10 shows plasmid pSBS4763 for the expression of Δ6-desaturase from the organism *M. alpina*. Shown are various features of the expression construct including promoters, termination sequences and resistance and marker genes. The plant selectable marker on this plasmid is pat, the phosphinothricin acetyl transferase from *Streptomyces viridochromogenes*. The bacterial marker is SpecR.

FIG. 10 shows the map of a construct used to express the Δ6-desaturase from *Mortierella alpina*. The plant selectable marker used in this construct was pat which corresponds to the phosphinothricin acetyl transferase gene from *Streptomyces viridochromogenes*. The bacterial marker used in this construct was SpecR. The base binary vector used to construct this vector is a derivative of pPZP200. See Hajdukiewicz et al., Plant Mol Biol 25: 989 (1994). The sequence of the insert contained within the borders of the pPZP200 plasmid is shown below.

pSBS4763 (*M. alpina* Δ6-desaturase expression cassette with PAT selection) (SEQ ID NO: 3)

```
ctgcaggaattcgatctctattgattcaaattacgatctgatactgataa
cgtctagattttagggttaaagcaatcaatcacctgacgattcaaggtg
gttggatcatgacgattccagaaaacatcaagcaagctctcaaagctaca
ctctttgggatcatactgaactctaacaacctcgttatgtcccgtagtgc
cagtacagacatcctcgtaactcggattgtgcacgatgccatgactatac
ccaacctcggtcttggtcacaccaggaactctctggtaagctagctccac
tccccagaaacaaccggcgccaaattgcgcgaattgctgacctgaagacg
gaacatcatcgtcgggtccttgggcgattgcggcggaagatgggtcagct
tgggcttgaggacgagacccgaatccgagtctgttgaaaaggttgttcat
tggggatttgtatacggagattggtcgtcgagaggtttgagggaaaggac
aaatgggtttggctctggagaaagagagtgcggctttagagagagaattg
agaggtttagagagagatgcggcggcgatgagcggaggagagacgacgag
gacctgcattatcaaagcagtgacgtggtgaaatttggaacttttaagag
gcagatagatttattatttgtatccattttcttcattgttctagaatgtc
gcggaacaaattttaaaactaaatcctaaattttttctaattttgttgcca
atagtggatatgtgggccgtatagaaggaatctattgaaggcccaaaccc
atactgacgagcccaaaggttcgttttgcgttttatgtttcggttcgatg
ccaacgccacattctgagctaggcaaaaaacaaacgtgtctttgaataga
ctcctctcgttaacacatgcagcggctgcatggtgacgccattaacacgt
ggcctacaattgcatgatgtctccattgacacgtgacttctcgtctcctt
tcttaatatatctaacaaacactcctacctcttccaaaatatatacacat
cttttgatcaatctctcattcaaaatctcattctctctagtaaacaaga
acaaaaaccatggctgctgctcccagtgtgaggacgtttactcgggccg
aggttttgaatgccgaggctctgaatgagggcaagaaggatgccgaggca
cccttcttgatgatcatcgacaacaaggtgtacgatgtccgcgagttcgt
ccctgatcatcccggtggaagtgtgattctcacgcacgttggcaaggacg
gcactgacgtctttgacacttttcaccccgaggctgcttgggagactctt
gccaacttttacgttggtgatattgacgagagcgaccgcgatatcaagaa
tgatgactttgcggccgaggtccgcaagctgcgtaccttgttccagtctc
ttggttactacgattcttccaaggcatactacgccttcaaggtctcgttc
aacctctgcatctgggggtttgtcgacggtcattgtggccaagtggggcca
gacctcgaccctcgccaacgtgctctcggctgcgcttttgggtctgttct
ggcagcagtgcggatggttggctcacgacttttttgcatcaccaggtcttc
caggaccgtttctggggtgatctttttcggcgccttcttgggaggtgtctg
ccagggcttctcgtcctcgtggtggaaggacaagcacaacactcaccacg
ccgcccccaacgtccacggcgaggatcccgacattgacacccaccctctg
ttgacctggagtgagcatgcgttggagatgttctcggatgtcccagatga
ggagctgacccgcatgtggtcgcgtttcatggtcctgaaccagacctggt
tttacttccccattctctcgtttgcccgtctctcctggtgcctccagtcc
attctctttgtgctgcctaacggtcaggcccacaagccctcgggcgcgcg
tgtgcccatctcgttggtcgagcagctgtcgcttgcgatgcactggacct
ggtacctcgccaccatgttcctgttcatcaaggatcccgtcaacatgctg
gtgtacttttggtgtcgcaggcggtgtgcggaaacttgttggcgatcgt
gttctcgctcaaccacaacggtatgcctgtgatctcgaaggaggaggcgg
tcgatatggatttcttcacgaagcagatcatcacgggtcgtgatgtccac
ccgggtctatttgccaactggttcacgggtggattgaactatcagatcga
gcaccacttgttcccttcgatgcctcgccacaacttttcaaagatccagc
```

```
ctgctgtcgagaccctgtgcaaaaagtacaatgtccgataccacaccacc
ggtatgatcgagggaactgcagaggtctttagccgtctgaacgaggtctc
caaggctgcctccaagatgggtaaggcgcagtaagcttgttaccccactg
atgtcatcgtcatagtccaataactccaatgtcggggagttagtttatga
ggaataaagtgtttagaatttgatcaggggagataataaaagccgagtt
tgaatcttttgttataagtaatgtttatgtgtgtttctatatgttgtca
aatggtcccatgttttcttcctctattttgtaacttgcaagtgttgtgt
tgtactttatttggcttctttgtaagttggtaacggtggtctatatatgg
aaaaggtcttgttttgttaaacttatgttagttaactggattcgtcttta
accacaaaaagttttcaataagctacaaatttagacacgcaagccgatgc
agtcattagtacatatatttattgcaagtgattacatggcaacccaaact
tcaaaaacagtaggttgctccatttagtaacctgaattgcctcctgattc
tagttgatcccggtaccgaattcgaatccaaaaattacggatatgaatat
aggcatatccgtatccgaattatccgtttgacagctagcaacgattgtac
aattgcttctttaaaaaaggaagaaagaaagaaagaaaagaatcaacatc
agcgttaacaaacggccccgttacggcccaaacggtcatatagagtaacg
gcgttaagcgttgaaagactcctatcgaaatacgtaaccgcaaacgtgtc
atagtcagatcccctcttccttcaccgcctcaaacacaaaaataatcttc
tacagcctatatataacccccccttctatctctcctttctcacaattc
atcatctttctttctctaccccaatttttaagaaatcctctcttctcctc
ttcattttcaaggtaaatctctctctctctctctctctctgttattcctt
gttttaattaggtatgtattattgctagtttgttaatctgcttatcttat
gtatgccttatgtgaatatctttatcttgttcatctcatccgtttagaag
ctataaatttgttgatttgactgtgtatctacacgtggttatgtttatat
ctaatcagatatgaatttcttcatattgttgcgtttgtgtgtaccaatcc
gaaatcgttgatttttttcatttaatcgtgtagctaattgtacgtataca
tatggatctacgtatcaattgttcatctgtttgtgtttgtatgtatacag
atctgaaaacatcacttctctcatctgattgtgttgttacatacatagat
atagatctgttatatcattttttttattaattgtgtatatatatatgtgca
tagatctggattacatgattgtgattatttacatgatttttgttatttacg
tatgtatatatgtagatctggacttttttggagttgttgacttgattgtat
ttgtgtgtgtatatgtgtgttctgatcttgatatgttatgtatgtgcagc
caaggctacgggcgatccaccatgtctccggagaggagaccagttgagat
taggccagctacagcagctgatatggccgcggtttgtgatatcgttaacc attacattgagacgtctacagtgaactttaggacagagccacaaacacca
caagagtggattgatgatctagagaggttgcaagatagataccatggttg
gttgctgaggttgagggtgttgtggctggtattgatacgctgggccctgg
aaggctaggaacgcttacgattggacagttgagagtactgtttacgtgtc
acataggcatcaaaggtgggcctaggttccacattgtacacacatttgc
ttaagtctatggaggcgcaaggttttaagtctgtggttgctgttataggc
cttccaaacgatccatctgttaggttgcatgaggctttgggatacacagc
ccggggtacattgcgcgcagctggatacaagcatggtggatggcatgatg
ttggttttggcaaagggattttgagttgccagctcctccaaggccagtt
aggccagttacccagatctgagtcgaccgaatgagttccaagatggtttg
tgacgaagttagttggttgtttttatggaactttgtttaagctagcttgt
aatgtggaaagaacgtgtggctttgtggtttttaaatgttggtgaataaa
gatgtttcctttggattaactagtattttcctattggtttcatggtttt
agcacacaacattttaaatatgctgttagatgatatgctgcctgctttat
tatttacttacccctcaccttcagtttcaaagttgttgcaatgactctgt
gtagtttaagatcgagtgaaagtagattttgtctatatttattaggggta
tttgatatgctaatggtaaacatggtttatgacagcgtacttttttggtt
atggtgttgacgtttccttttaaacattatagtagcgtccttggtctgtg
ttcattggttgaacaaaggcacactcacttggagatgccgtctccactga
tatttgaaca
```

Transformation of safflower with this construct was performed by SemBioSys Genetics Inc. (Calgary, Canada). Techniques utilized by SemBioSys Genetics Inc. include those described in WO 2004/111244, which is hereby incorporated by reference in its entirety. Transgenic plants will be grown and seed will be harvested.

Seeds were collected from transgenic plants and fatty acid composition was performed using a modification of a gas chromatographic method described in "Official Methods and Recommended Practices of the AOCS", 5$^{th}$ Ed., Method Ce 1-62, American Oil Chemists Society: Champaign, Ill. (1997).

As shown below in Table 10, GLA levels ranged from 7.8% (line 4763-13-2) to 50.19% (line 4763-28-1) in T1 seed from transgenic lines expressing Δ6-desaturase from *M. alpina* in the pSBS4763 construct. Since T1 lines are still segregating, measurements of single seed samples can vary due to null, heterozygous or homozygous insertions. GLA levels in Centennial controls and Null control lines were 0.05 or below. LA levels in Centennial are naturally high and GLA levels in Centennial can be increased with the expression of Δ6-desaturase only.

TABLE 10

Examples of single seed fatty acid composition of T1 seed of pSBS4763 construct expressed in Centennial

| Table 10 Line Number | Type | C18:3n6 (gamma Linolenic) | C16:0 (Palmitic) | C18:0 (Stearic) | C18:1n9 (Oleic) | C18:2n6 (Linoleic) |
|---|---|---|---|---|---|---|
| 4763-1-1 | Transgenic | 8.36 | 6.41 | 1.50 | 7.70 | 74.82 |
| 4763-1-2 | Transgenic | 14.28 | 6.26 | 1.56 | 9.01 | 67.69 |

TABLE 10-continued

Examples of single seed fatty acid composition of T1 seed of pSBS4763 construct expressed in Centennial

| Table 10 Line Number | Type | C18:3n6 (gamma Linolenic) | C16:0 (Palmitic) | C18:0 (Stearic) | C18:1n9 (Oleic) | C18:2n6 (Linoleic) |
|---|---|---|---|---|---|---|
| 4763-2-1 | Transgenic | 16.29 | 6.56 | 1.53 | 8.19 | 66.38 |
| 4763-2-2 | Transgenic | 11.31 | 6.46 | 1.59 | 9.12 | 70.23 |
| 4763-13-2 | Transgenic | 7.80 | 6.54 | 1.53 | 8.69 | 74.06 |
| 4763-13-3 | NULL | 0.05 | 6.27 | 1.33 | 8.16 | 82.98 |
| 4763-15-1 | Transgenic | 11.22 | 6.24 | 1.26 | 7.91 | 70.36 |
| 4763-15-2 | Transgenic | 19.40 | 6.56 | 2.43 | 7.65 | 62.65 |
| 4763-16-1 | Transgenic | 17.94 | 6.22 | 1.42 | 7.29 | 66.36 |
| 4763-16-2 | Transgenic | 11.79 | 6.08 | 1.86 | 7.97 | 70.78 |
| 4763-17-2 | NULL | 0.04 | 6.33 | 1.37 | 9.19 | 81.84 |
| 4763-17-3 | Transgenic | 8.43 | 6.52 | 1.53 | 9.56 | 72.75 |
| 4763-18-2 | Transgenic | 8.73 | 6.81 | 2.00 | 9.33 | 70.68 |
| 4763-18-3 | NULL | 0.00 | 6.68 | 1.88 | 9.38 | 80.91 |
| 4763-19-4 | Transgenic | 12.71 | 6.72 | 1.87 | 7.16 | 68.74 |
| 4763-19-15 | Transgenic | 14.55 | 6.46 | 1.75 | 7.41 | 67.84 |
| 4763-21-2 | Transgenic | 20.62 | 6.89 | 2.37 | 5.51 | 59.73 |
| 4763-21-11 | Transgenic | 20.99 | 6.93 | 1.77 | 6.12 | 61.40 |
| 4763-22-4 | Transgenic | 10.55 | 6.45 | 1.53 | 7.47 | 73.23 |
| 4763-22-5 | Transgenic | 16.32 | 6.71 | 1.47 | 8.05 | 66.28 |
| 4763-23-12 | Transgenic | 34.02 | 6.92 | 2.06 | 5.21 | 49.27 |
| 4763-23-14 | Transgenic | 36.92 | 7.58 | 1.60 | 7.20 | 45.69 |
| 4763-24-6 | Transgenic | 17.67 | 8.80 | 3.89 | 7.22 | 56.08 |
| 4763-24-7 | Transgenic | 14.42 | 8.78 | 5.30 | 9.12 | 57.06 |
| 4763-25-2 | Transgenic | 18.05 | 8.68 | 4.35 | 7.01 | 54.70 |
| 4763-25-3 | Transgenic | 26.62 | 10.06 | 7.29 | 6.10 | 38.93 |
| 4763-27-3 | Transgenic | 40.91 | 8.92 | 3.40 | 5.04 | 24.89 |
| 4763-27-9 | Transgenic | 19.61 | 14.67 | 15.70 | 3.95 | 19.56 |
| 4763-28-1 | Transgenic | 50.19 | 9.71 | 1.88 | 6.14 | 30.45 |
| 4763-28-2 | Transgenic | 37.35 | 7.78 | 1.61 | 6.18 | 46.12 |
| 4763-30-12 | Transgenic | 8.04 | 7.22 | 2.11 | 7.87 | 73.03 |
| 4763-30-13 | Transgenic | 9.08 | 7.55 | 2.17 | 9.44 | 69.75 |
| Centennial-1 | Control | 0.00 | 6.33 | 2.18 | 15.74 | 74.86 |
| Centennial-3 | Control | 0.00 | 6.97 | 2.13 | 13.92 | 76.18 |

These data show that Δ6-desaturases from a variety of sources can be used to increase GLA production in safflower. Transgenic expression of Δ6-desaturase in a plant variety that is naturally high in LA, as is the Centennial variety, is effective at increasing GLA content.

The following statements of the invention are intended to characterize possible elements of the invention according to the foregoing description given in the specification.

We claim:

1. Oil extracted from transgenic safflower seeds comprising gamma-linolenic acid (GLA) at a level of at least 40% by weight of the total fatty acid content of said seeds.

2. The oil of claim 1 wherein said oil is extracted from transgenic safflower seeds comprising GLA at about 40-45, 45-50, 50-55 or 55-60% or greater by weight of the total fatty acid content of said seeds.

3. Oil extracted from the seeds of transgenic safflower plants comprising a recombinant promoter function in said safflower plant wherein said promoter is operably linked to a recombinant DNA sequence encoding a single desaturase, wherein said single desaturase consists of a Δ6-desaturase, wherein said safflower plant is grown under conditions whereby said Δ6-desaturase is expressed, and wherein said safflower plant produces seeds and said seeds comprise GLA at a level of a least 40% by weight of the total fatty acid content of said seeds.

4. The oil of claim 3 wherein said oil is extracted from seeds of transgenic safflower plants comprising a plant or fungal Δ6-desaturase.

5. The oil of claim 4 wherein said plant or fungal desaturase is selected from the group consisting of *Mucor, Saprolegnia, Saprolegnia diclina, Mortierella, Mortierella alpina, Conidiobolus, Pythium, Phytophthora, Penicillium, Porphyridium, Coidosporium, Mucor circinelloides, Fusarium, Aspergillus, Candida, Rhodotorula, Entomophthora, Thraustochytrium, Borago, Primula*, sunflower, canola, rice, and moss Δ6-desaturases.

6. The oil of claim 3 wherein said seeds comprises GLA at about 40-45, 45-50, 50-55 or 55-60% or greater by weight of the total fatty acid content of said seeds.

7. A nutritional product containing the oil of claim 1.

8. The nutritional product of claim 7 wherein said nutritional product is selected from the group consisting of skin creams, balms and lotions, moisturizers, tanning and after tanning products, shampoos, hair conditioners and lipsticks.

9. A personal care product containing the oil of claim 1.

10. The personal care product of claim 9 wherein said personal care product is selected from the group consisting of infant formulas, dietary supplements, dietary substitutes and rehydration compositions.

* * * * *